(12) United States Patent
Boudreaux et al.

(10) Patent No.: US 7,597,229 B2
(45) Date of Patent: Oct. 6, 2009

(54) END EFFECTOR CLOSURE SYSTEM FOR A SURGICAL STAPLING INSTRUMENT

(75) Inventors: Chad P. Boudreaux, Cincinnati, OH (US); Stephen J. Balek, Rome (IT)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 27 days.

(21) Appl. No.: 11/821,425

(22) Filed: Jun. 22, 2007

(65) Prior Publication Data

US 2008/0314961 A1   Dec. 25, 2008

(51) Int. Cl.
*A61B 17/068* (2006.01)

(52) U.S. Cl. .................. 227/175.2; 227/175.1; 227/19; 227/178.1; 227/179.1

(58) Field of Classification Search ............... 227/175.1, 227/19, 175.2, 178.1, 179.1, 180.1, 182.1
See application file for complete search history.

(56) References Cited

U.S. PATENT DOCUMENTS

| | | | |
|---|---|---|---|
| 2,853,074 A | 9/1958 | Olson | |
| 2,959,974 A | 11/1960 | Emrick | |
| 3,490,675 A | 1/1970 | Green et al. | |
| 3,551,987 A | 1/1971 | WIlkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,500,024 A | 2/1985 | DiGiovanni et al. | |
| 4,505,273 A | 3/1985 | Braun et al. | |

(Continued)

FOREIGN PATENT DOCUMENTS

CA   2458946 A1   3/2003

(Continued)

OTHER PUBLICATIONS

U.S. Appl. No. 11/821,426, filed Jun. 22, 2007.

(Continued)

*Primary Examiner*—Brian D Nash

(57) ABSTRACT

A surgical instrument including a closure system configured to move an anvil of an end effector between an open position, a partially closed position, and a closed position. The surgical instrument can further include a lock member configured to selectively engage and lock the closure system when the anvil is positioned in at least one of its partially closed and closed positions. In at least one embodiment, the surgical instrument can include a trigger configured to pivot the anvil, the lock member can include a follower portion, and the closure drive can include a lock spring configured to bias the follower portion against a cam surface of the trigger such that the follower portion can engage a notch in the cam surface when the anvil is pivoted into its partially closed position, or closed position, and prevent the anvil from being pivoted into its open position.

28 Claims, 63 Drawing Sheets

U.S. PATENT DOCUMENTS

| | | | |
|---|---|---|---|
| 4,522,327 A | 6/1985 | Korthoff et al. | |
| 4,530,453 A | 7/1985 | Green | |
| 4,565,109 A | 1/1986 | Tsay | |
| 4,566,620 A | 1/1986 | Green et al. | |
| 4,573,622 A | 3/1986 | Green et al. | |
| 4,580,712 A | 4/1986 | Green | |
| 4,610,383 A | 9/1986 | Rothfuss et al. | |
| 4,629,107 A | 12/1986 | Fedotov et al. | |
| 4,655,222 A | 4/1987 | Florez et al. | |
| 4,664,305 A | 5/1987 | Blake, III et al. | |
| 4,671,445 A | 6/1987 | Barker et al. | |
| 4,715,520 A | 12/1987 | Roehr, Jr. et al. | |
| 4,728,020 A | 3/1988 | Green et al. | |
| 4,754,909 A | 7/1988 | Barker et al. | |
| 4,767,044 A | 8/1988 | Green | |
| 4,809,695 A | 3/1989 | Gwathmey et al. | |
| 4,817,847 A | 4/1989 | Redtenbacher et al. | |
| 4,821,939 A | 4/1989 | Green | |
| 4,869,414 A | 9/1989 | Green et al. | |
| 4,869,415 A | 9/1989 | Fox | |
| 4,880,015 A | 11/1989 | Nierman | |
| 4,941,623 A | 7/1990 | Pruitt | |
| 4,944,443 A | 7/1990 | Oddsen et al. | |
| 4,973,274 A | 11/1990 | Hirukawa | |
| 5,065,929 A | 11/1991 | Schulze et al. | |
| 5,071,430 A | 12/1991 | de Salis et al. | |
| 5,129,570 A | 7/1992 | Schulze et al. | |
| 5,137,198 A | 8/1992 | Nobis et al. | |
| 5,139,513 A | 8/1992 | Segato | |
| 5,158,567 A | 10/1992 | Green | |
| 5,209,747 A | 5/1993 | Knoepfler | |
| 5,211,649 A | 5/1993 | Kohler et al. | |
| 5,221,036 A | 6/1993 | Takase | |
| 5,222,975 A | 6/1993 | Crainich | |
| 5,258,009 A | 11/1993 | Conners | |
| 5,282,806 A | 2/1994 | Haber et al. | |
| 5,282,829 A | 2/1994 | Hermes | |
| 5,304,204 A | 4/1994 | Bregen | |
| 5,318,221 A * | 6/1994 | Green et al. | 227/178.1 |
| 5,342,395 A | 8/1994 | Jarrett et al. | |
| 5,342,396 A | 8/1994 | Cook | |
| 5,350,400 A | 9/1994 | Esposito et al. | |
| 5,366,479 A | 11/1994 | McGarry et al. | |
| 5,383,888 A | 1/1995 | Zvenyatsky et al. | |
| 5,397,324 A | 3/1995 | Carroll et al. | |
| 5,413,268 A * | 5/1995 | Green et al. | 227/176.1 |
| 5,417,203 A | 5/1995 | Tovey et al. | |
| 5,425,745 A | 6/1995 | Green et al. | |
| 5,456,401 A | 10/1995 | Green et al. | |
| 5,474,566 A | 12/1995 | Alesi et al. | |
| 5,478,354 A | 12/1995 | Tovey et al. | |
| 5,480,089 A | 1/1996 | Blewett | |
| 5,482,197 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A * | 1/1996 | Knodel et al. | 227/181.1 |
| 5,489,058 A | 2/1996 | Plyley et al. | |
| 5,497,933 A | 3/1996 | DeFonzo et al. | |
| 5,503,320 A | 4/1996 | Webster et al. | |
| 5,509,596 A | 4/1996 | Green et al. | |
| 5,529,235 A | 6/1996 | Boiarski et al. | |
| 5,535,934 A | 7/1996 | Boiarski et al. | |
| 5,535,935 A | 7/1996 | Vidal et al. | |
| 5,540,375 A | 7/1996 | Bolanos et al. | |
| 5,542,594 A | 8/1996 | McKean et al. | |
| 5,547,117 A | 8/1996 | Hamblin et al. | |
| 5,553,765 A | 9/1996 | Knodel et al. | |
| 5,554,169 A | 9/1996 | Green et al. | |
| 5,560,532 A | 10/1996 | DeFonzo et al. | |
| 5,562,239 A | 10/1996 | Boiarski et al. | |
| 5,562,241 A * | 10/1996 | Knodel et al. | 227/175.1 |
| 5,562,682 A | 10/1996 | Oberlin et al. | |
| 5,564,615 A | 10/1996 | Bishop et al. | |
| 5,571,116 A | 11/1996 | Bolanos et al. | |
| 5,575,799 A | 11/1996 | Bolanos et al. | |
| 5,577,654 A | 11/1996 | Bishop | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,609,285 A | 3/1997 | Grant et al. | |
| 5,624,452 A | 4/1997 | Yates | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,632,433 A | 5/1997 | Grant et al. | |
| 5,634,584 A | 6/1997 | Okorocha et al. | |
| 5,636,779 A | 6/1997 | Palmer | |
| 5,636,780 A | 6/1997 | Green et al. | |
| 5,639,008 A | 6/1997 | Gallagher et al. | |
| 5,645,209 A | 7/1997 | Green et al. | |
| 5,647,526 A | 7/1997 | Green et al. | |
| 5,649,937 A | 7/1997 | Bito et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,667,527 A | 9/1997 | Cook | |
| 5,669,544 A | 9/1997 | Schulze et al. | |
| 5,673,840 A | 10/1997 | Schulze et al. | |
| 5,673,841 A | 10/1997 | Schulze et al. | |
| 5,680,981 A | 10/1997 | Mililli et al. | |
| 5,680,982 A | 10/1997 | Schulze et al. | |
| 5,685,474 A | 11/1997 | Seeber | |
| 5,690,269 A | 11/1997 | Bolanos et al. | |
| 5,692,668 A | 12/1997 | Schulze et al. | |
| 5,697,543 A | 12/1997 | Burdorff | |
| 5,702,408 A | 12/1997 | Wales et al. | |
| 5,704,534 A | 1/1998 | Huitema et al. | |
| 5,706,997 A | 1/1998 | Green et al. | |
| 5,711,472 A | 1/1998 | Bryan | |
| 5,713,505 A | 2/1998 | Huitema | |
| 5,715,987 A | 2/1998 | Kelley et al. | |
| 5,716,366 A | 2/1998 | Yates | |
| 5,718,359 A | 2/1998 | Palmer et al. | |
| 5,725,536 A | 3/1998 | Oberlin et al. | |
| 5,725,554 A | 3/1998 | Simon et al. | |
| 5,732,821 A * | 3/1998 | Stone et al. | 206/370 |
| 5,732,871 A | 3/1998 | Clark et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,255 A * | 6/1998 | Chrisman et al. | 227/175.2 |
| 5,762,256 A | 6/1998 | Mastri et al. | |
| 5,779,130 A | 7/1998 | Alesi et al. | |
| 5,779,132 A | 7/1998 | Knodel et al. | |
| 5,782,397 A | 7/1998 | Koukline | |
| 5,785,232 A | 7/1998 | Vidal et al. | |
| 5,794,834 A | 8/1998 | Hamblin et al. | |
| 5,797,536 A | 8/1998 | Smith et al. | |

| | | | | | | |
|---|---|---|---|---|---|---|
| 5,797,537 | A | 8/1998 | Oberlin et al. | RE38,708 | E | 3/2005 | Bolanos et al. |
| 5,797,538 | A | 8/1998 | Heaton et al. | 6,877,647 | B2 | 4/2005 | Green et al. |
| 5,799,857 | A | 9/1998 | Robertson et al. | 6,905,057 | B2 | 6/2005 | Swayze et al. |
| 5,820,009 | A | 10/1998 | Melling et al. | 6,945,444 | B2 | 9/2005 | Gresham et al. |
| 5,826,776 | A | 10/1998 | Schulze et al. | 6,953,138 | B1 | 10/2005 | Dworak et al. |
| 5,833,695 | A | 11/1998 | Yoon | 6,953,139 | B2 | 10/2005 | Milliman et al. |
| 5,836,503 | A | 11/1998 | Ehrenfels et al. | 6,959,852 | B2 * | 11/2005 | Shelton et al. ............ 227/182.1 |
| 5,839,639 | A | 11/1998 | Sauer et al. | 6,960,107 | B1 | 11/2005 | Schaub et al. |
| 5,855,311 | A | 1/1999 | Hamblin et al. | 6,964,363 | B2 | 11/2005 | Wales et al. |
| 5,865,361 | A | 2/1999 | Milliman et al. | 6,978,921 | B2 | 12/2005 | Shelton, IV et al. |
| 5,868,760 | A | 2/1999 | McGuckin, Jr. | 6,978,922 | B2 | 12/2005 | Bilotti et al. |
| 5,871,135 | A | 2/1999 | Williamson, IV et al. | 6,981,628 | B2 | 1/2006 | Wales |
| 5,878,937 | A | 3/1999 | Green et al. | 6,986,451 | B1 | 1/2006 | Mastri et al. |
| 5,894,979 | A | 4/1999 | Powell | 6,988,649 | B2 | 1/2006 | Shelton, IV et al. |
| 5,897,562 | A | 4/1999 | Bolanos et al. | 6,988,650 | B2 | 1/2006 | Schwemberger et al. |
| 5,901,895 | A | 5/1999 | Heaton et al. | 7,000,818 | B2 | 2/2006 | Shelton, IV et al. |
| 5,911,353 | A | 6/1999 | Bolanos et al. | 7,000,819 | B2 | 2/2006 | Swayze et al. |
| 5,915,616 | A | 6/1999 | Viola et al. | 7,008,435 | B2 | 3/2006 | Cummins |
| 5,941,442 | A | 8/1999 | Geiste et al. | 7,032,798 | B2 | 4/2006 | Whitman et al. |
| 5,954,259 | A | 9/1999 | Viola et al. | 7,032,799 | B2 | 4/2006 | Viola et al. |
| 6,010,054 | A | 1/2000 | Johnson et al. | 7,044,352 | B2 | 5/2006 | Shelton, IV et al. |
| 6,032,849 | A | 3/2000 | Mastri et al. | 7,044,353 | B2 | 5/2006 | Mastri et al. |
| 6,045,560 | A | 4/2000 | McKean et al. | 7,055,731 | B2 | 6/2006 | Shelton, IV et al. |
| 6,047,861 | A | 4/2000 | Vidal et al. | 7,056,330 | B2 | 6/2006 | Gayton |
| 6,050,472 | A | 4/2000 | Shibata | 7,059,508 | B2 | 6/2006 | Shelton, IV et al. |
| 6,062,360 | A | 5/2000 | Shields | 7,070,083 | B2 | 7/2006 | Jankowski |
| 6,079,606 | A | 6/2000 | Milliman et al. | 7,077,856 | B2 | 7/2006 | Whitman |
| 6,083,242 | A | 7/2000 | Cook | 7,083,075 | B2 | 8/2006 | Swayze et al. |
| 6,086,600 | A | 7/2000 | Kortenbach | 7,090,684 | B2 | 8/2006 | McGuckin, Jr. et al. |
| 6,102,271 | A | 8/2000 | Longo et al. | 7,097,089 | B2 | 8/2006 | Marczyk |
| 6,109,500 | A | 8/2000 | Alli et al. | 7,108,709 | B2 | 9/2006 | Cummins |
| 6,119,913 | A | 9/2000 | Adams et al. | 7,111,769 | B2 | 9/2006 | Wales et al. |
| 6,126,058 | A | 10/2000 | Adams et al. | 7,114,642 | B2 | 10/2006 | Whitman |
| 6,155,473 | A | 12/2000 | Tompkins et al. | 7,118,582 | B1 | 10/2006 | Wang et al. |
| 6,171,330 | B1 | 1/2001 | Benchetrit | 7,128,253 | B2 | 10/2006 | Mastri et al. |
| 6,202,914 | B1 | 3/2001 | Geiste et al. | 7,140,527 | B2 | 11/2006 | Ehrenfels et al. |
| 6,241,139 | B1 | 6/2001 | Milliman et al. | 7,143,923 | B2 | 12/2006 | Shelton, IV et al. |
| 6,250,532 | B1 | 6/2001 | Green et al. | 7,143,924 | B2 | 12/2006 | Scirica et al. |
| 6,264,086 | B1 | 7/2001 | McGuckin, Jr. | 7,143,925 | B2 | 12/2006 | Shelton, IV et al. |
| 6,264,087 | B1 | 7/2001 | Whitman | 7,147,138 | B2 | 12/2006 | Shelton, IV |
| 6,273,897 | B1 | 8/2001 | Dalessandro et al. | 7,159,750 | B2 | 1/2007 | Racenet et al. |
| 6,302,311 | B1 | 10/2001 | Adams et al. | 7,168,604 | B2 | 1/2007 | Milliman et al. |
| 6,315,184 | B1 | 11/2001 | Whitman | 7,188,758 | B2 | 3/2007 | Viola et al. |
| 6,330,965 | B1 | 12/2001 | Milliman et al. | 7,210,609 | B2 | 5/2007 | Leiboff et al. |
| 6,387,113 | B1 | 5/2002 | Hawkins et al. | 7,213,736 | B2 | 5/2007 | Wales et al. |
| RE37,814 | E | 8/2002 | Allgeyer | 7,220,272 | B2 | 5/2007 | Weadock |
| 6,439,439 | B1 | 8/2002 | Rickard et al. | 7,225,964 | B2 | 6/2007 | Mastri et al. |
| 6,443,973 | B1 | 9/2002 | Whitman | 7,238,195 | B2 | 7/2007 | Viola |
| 6,488,197 | B1 | 12/2002 | Whitman | 7,246,734 | B2 | 7/2007 | Shelton, IV |
| 6,491,201 | B1 | 12/2002 | Whitman | 7,258,262 | B2 | 8/2007 | Mastri et al. |
| 6,505,768 | B2 | 1/2003 | Whitman | 7,278,563 | B1 | 10/2007 | Green |
| 6,517,565 | B1 | 2/2003 | Whitman et al. | 7,296,724 | B2 | 11/2007 | Green et al. |
| 6,578,751 | B2 | 6/2003 | Hartwick | 7,303,106 | B2 | 12/2007 | Milliman et al. |
| 6,601,749 | B2 | 8/2003 | Sullivan et al. | 7,303,107 | B2 | 12/2007 | Milliman et al. |
| 6,616,686 | B2 | 9/2003 | Coleman et al. | 7,303,108 | B2 | 12/2007 | Shelton, IV |
| 6,619,529 | B2 | 9/2003 | Green et al. | 7,328,828 | B2 | 2/2008 | Ortiz et al. |
| 6,629,988 | B2 | 10/2003 | Weadock | 7,328,829 | B2 | 2/2008 | Arad et al. |
| 6,644,532 | B2 | 11/2003 | Green et al. | 7,343,920 | B2 | 3/2008 | Toby et al. |
| 6,669,073 | B2 | 12/2003 | Milliman et al. | 7,364,061 | B2 | 4/2008 | Swayze et al. |
| 6,681,978 | B2 | 1/2004 | Geiste et al. | 7,380,695 | B2 | 6/2008 | Doll et al. |
| 6,681,979 | B2 | 1/2004 | Whitman | 7,380,696 | B2 | 6/2008 | Shelton, IV et al. |
| 6,695,199 | B2 | 2/2004 | Whitman | 7,396,356 | B2 | 7/2008 | Mollenauer |
| 6,698,643 | B2 | 3/2004 | Whitman | 7,398,908 | B2 | 7/2008 | Holsten et al. |
| 6,716,233 | B1 | 4/2004 | Whitman | 7,404,508 | B2 | 7/2008 | Smith et al. |
| 6,755,338 | B2 | 6/2004 | Hahnen et al. | 7,404,509 | B2 | 7/2008 | Ortiz et al. |
| 6,773,438 | B1 | 8/2004 | Knodel et al. | 7,407,075 | B2 | 8/2008 | Holsten et al. |
| 6,786,382 | B1 | 9/2004 | Hoffman | 7,410,086 | B2 | 8/2008 | Ortiz et al. |
| 6,805,273 | B2 | 10/2004 | Bilotti et al. | 7,422,136 | B1 | 9/2008 | Marczyk |
| 6,817,508 | B1 | 11/2004 | Racenet et al. | 7,424,965 | B2 | 9/2008 | Racenet et al. |
| 6,817,509 | B2 | 11/2004 | Geiste et al. | 7,431,730 | B2 | 10/2008 | Viola |
| 6,817,974 | B2 | 11/2004 | Cooper et al. | 7,434,715 | B2 | 10/2008 | Shelton, IV et al. |
| 6,830,174 | B2 | 12/2004 | Hillstead et al. | 7,434,717 | B2 | 10/2008 | Shelton, IV et al. |
| 6,843,403 | B2 | 1/2005 | Whitman | 7,438,209 | B1 | 10/2008 | Hess et al. |

| | | |
|---|---|---|
| 7,441,685 B1 | 10/2008 | Boudreaux |
| 7,464,847 B2 | 12/2008 | Viola et al. |
| 7,490,749 B2 | 2/2009 | Schall et al. |
| 7,494,039 B2 | 2/2009 | Racenet et al. |
| 7,506,791 B2 | 3/2009 | Omaits et al. |
| 2002/0117534 A1 | 8/2002 | Green et al. |
| 2004/0006372 A1 | 1/2004 | Racenet et al. |
| 2004/0034369 A1 | 2/2004 | Sauer et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0254608 A1 | 12/2004 | Huitema et al. |
| 2005/0059997 A1 | 3/2005 | Bauman et al. |
| 2005/0067459 A1* | 3/2005 | Swayze et al. ........... 227/176.1 |
| 2005/0103819 A1 | 5/2005 | Racenet et al. |
| 2005/0119669 A1 | 6/2005 | Demmy |
| 2005/0125009 A1 | 6/2005 | Perry et al. |
| 2005/0143759 A1 | 6/2005 | Kelly |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0216055 A1 | 9/2005 | Scirica et al. |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0151567 A1 | 7/2006 | Roy |
| 2006/0180634 A1 | 8/2006 | Shelton, IV et al. |
| 2006/0190029 A1 | 8/2006 | Wales |
| 2006/0190031 A1 | 8/2006 | Wales et al. |
| 2006/0226196 A1 | 10/2006 | Hueil et al. |
| 2006/0229665 A1 | 10/2006 | Wales et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023477 A1 | 2/2007 | Whitman et al. |
| 2007/0027469 A1 | 2/2007 | Smith et al. |
| 2007/0034668 A1 | 2/2007 | Holsten et al. |
| 2007/0045379 A1 | 3/2007 | Shelton, IV |
| 2007/0073340 A1 | 3/2007 | Shelton, IV et al. |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102476 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0262116 A1 | 11/2007 | Hueil et al. |
| 2007/0288044 A1 | 12/2007 | Jinno et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0183193 A1 | 7/2008 | Omori et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314956 A1 | 12/2008 | Boudreaux |

| | | | | | | |
|---|---|---|---|---|---|---|
| 2008/0314957 A1 | 12/2008 | Boudreaux | | EP | 1477119 A1 | 11/2004 |
| 2008/0314962 A1 | 12/2008 | Boudreaux | | EP | 1479345 A1 | 11/2004 |
| 2009/0001121 A1 | 1/2009 | Hess et al. | | EP | 1479347 A1 | 11/2004 |
| 2009/0001123 A1 | 1/2009 | Morgan et al. | | EP | 1479348 A1 | 11/2004 |
| 2009/0001124 A1 | 1/2009 | Hess et al. | | EP | 1520521 A1 | 4/2005 |
| 2009/0001125 A1 | 1/2009 | Hess et al. | | EP | 1520523 A1 | 4/2005 |
| 2009/0001126 A1 | 1/2009 | Hess et al. | | EP | 1520525 A1 | 4/2005 |
| 2009/0001128 A1 | 1/2009 | Weisenburgh, II et al. | | EP | 1522264 A1 | 4/2005 |
| 2009/0001130 A1 | 1/2009 | Hess et al. | | EP | 1550408 A1 | 7/2005 |
| 2009/0005807 A1 | 1/2009 | Hess et al. | | EP | 1557129 A1 | 7/2005 |
| 2009/0005808 A1 | 1/2009 | Hess et al. | | EP | 1064883 B1 | 8/2005 |
| 2009/0005809 A1 | 1/2009 | Hess et al. | | EP | 1621138 A2 | 2/2006 |
| 2009/0012556 A1 | 1/2009 | Boudreaux et al. | | EP | 1621141 A2 | 2/2006 |
| 2009/0076534 A1 | 3/2009 | Shelton, IV et al. | | EP | 1652481 A2 | 5/2006 |

FOREIGN PATENT DOCUMENTS

| | | | | | | |
|---|---|---|---|---|---|---|
| | | | | EP | 1382303 B1 | 6/2006 |
| CA | 2512960 A1 | 1/2006 | | EP | 1045672 B1 | 8/2006 |
| CA | 2514274 A1 | 1/2006 | | EP | 1617768 B1 | 8/2006 |
| DE | 273689 C | 5/1914 | | EP | 1702567 A2 | 9/2006 |
| DE | 1775926 A | 1/1972 | | EP | 1129665 B1 | 11/2006 |
| DE | 9412228 U | 9/1994 | | EP | 1256317 B1 | 12/2006 |
| DE | 19924311 A1 | 11/2000 | | EP | 1728473 A1 | 12/2006 |
| DE | 69328576 T2 | 1/2001 | | EP | 1728475 A2 | 12/2006 |
| DE | 20112837 U1 | 10/2001 | | EP | 1479346 B1 | 1/2007 |
| DE | 20121753 U1 | 4/2003 | | EP | 1484024 B1 | 1/2007 |
| DE | 10314072 A1 | 10/2004 | | EP | 1754445 A2 | 2/2007 |
| EP | 0122046 A1 | 10/1984 | | EP | 1759812 A1 | 3/2007 |
| EP | 0033548 B1 | 5/1986 | | EP | 1300117 B1 | 8/2007 |
| EP | 0276104 A2 | 7/1988 | | EP | 1813199 A1 | 8/2007 |
| EP | 0639349 A2 | 2/1994 | | EP | 1813207 A1 | 8/2007 |
| EP | 0593920 A1 | 4/1994 | | EP | 1839596 A2 | 2/2008 |
| EP | 0600182 A2 | 6/1994 | | EP | 1897502 A1 | 3/2008 |
| EP | 0630612 A1 | 12/1994 | | EP | 1749486 B1 | 3/2009 |
| EP | 0634144 A1 | 1/1995 | | FR | 999646 A | 2/1952 |
| EP | 0646356 A2 | 4/1995 | | FR | 1112936 A | 3/1956 |
| EP | 0646357 A1 | 4/1995 | | FR | 2765794 A | 1/1999 |
| EP | 0669104 A1 | 8/1995 | | GB | 939929 A | 10/1963 |
| EP | 0679367 A2 | 11/1995 | | GB | 2336214 A | 10/1999 |
| EP | 0392547 B1 | 12/1995 | | JP | 6007357 A | 1/1994 |
| EP | 0685204 A1 | 12/1995 | | JP | 7051273 A | 2/1995 |
| EP | 0699418 A1 | 3/1996 | | JP | 8033641 A | 2/1996 |
| EP | 0702937 A1 | 3/1996 | | JP | 8229050 A | 9/1996 |
| EP | 0705571 A1 | 4/1996 | | JP | 2000287987 A | 10/2000 |
| EP | 0484677 B2 | 6/1996 | | JP | 2001286477 A | 10/2001 |
| EP | 0541987 B1 | 7/1996 | | JP | 2002369820 A | 12/2002 |
| EP | 0667119 B1 | 7/1996 | | JP | 2005505322 T | 2/2005 |
| EP | 0770355 A1 | 5/1997 | | JP | 2005103293 A | 4/2005 |
| EP | 0503662 B1 | 6/1997 | | RU | 2187249 C2 | 8/2002 |
| EP | 0625335 B1 | 11/1997 | | RU | 2225170 C2 | 3/2004 |
| EP | 0552423 B1 | 1/1998 | | SU | 1377053 A1 | 2/1988 |
| EP | 0592244 B1 | 1/1998 | | SU | 1561964 A1 | 5/1990 |
| EP | 0648476 B1 | 1/1998 | | SU | 1722476 A1 | 3/1992 |
| EP | 0603472 B1 | 11/1998 | | WO | WO 93/08755 A1 | 5/1993 |
| EP | 0605351 B1 | 11/1998 | | WO | WO 95/18572 A1 | 7/1995 |
| EP | 0878169 A1 | 11/1998 | | WO | WO 95/23557 A1 | 9/1995 |
| EP | 0879742 A1 | 11/1998 | | WO | WO 95/29639 A1 | 11/1995 |
| EP | 0760230 B1 | 2/1999 | | WO | WO 96/35464 A1 | 11/1996 |
| EP | 0537572 B1 | 6/1999 | | WO | WO 97/34533 A1 | 9/1997 |
| EP | 0552050 B1 | 5/2000 | | WO | WO 98/30153 A1 | 7/1998 |
| EP | 1090592 A1 | 4/2001 | | WO | WO 99/12483 A1 | 3/1999 |
| EP | 1256318 B1 | 5/2001 | | WO | WO 99/15086 A1 | 4/1999 |
| EP | 0908152 B1 | 1/2002 | | WO | WO 99/34744 A1 | 7/1999 |
| EP | 0872213 B1 | 5/2002 | | WO | WO 99/45849 A1 | 9/1999 |
| EP | 1238634 A2 | 9/2002 | | WO | WO 00/57796 A1 | 10/2000 |
| EP | 0656188 B1 | 1/2003 | | WO | WO 00/64365 A1 | 11/2000 |
| EP | 0829235 B1 | 6/2003 | | WO | WO 00/72762 A1 | 12/2000 |
| EP | 0813843 B1 | 10/2003 | | WO | WO 00/72765 A1 | 12/2000 |
| EP | 0741996 B1 | 2/2004 | | WO | WO 01/05702 A1 | 1/2001 |
| EP | 0705570 B1 | 4/2004 | | WO | WO 01/10482 A1 | 2/2001 |
| EP | 1086713 B1 | 5/2004 | | WO | WO 01/54594 A1 | 8/2001 |
| EP | 1426012 A1 | 6/2004 | | WO | WO 01/62158 A2 | 8/2001 |
| EP | 0888749 B1 | 9/2004 | | WO | WO 01/62162 A1 | 8/2001 |
| | | | | WO | WO 01/62164 A2 | 8/2001 |
| | | | | WO | WO 01/91646 A1 | 12/2001 |

| | | | |
|---|---|---|---|
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/096954 A2 | 10/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |
| WO | WO 2007/121579 A1 | 11/2007 |
| WO | WO 2007/142625 A2 | 12/2007 |
| WO | WO 2008/045383 A2 | 4/2008 |

OTHER PUBLICATIONS

U.S. Appl. No. 11/821,277, filed Jun. 22, 2007.
U.S. Appl. No. 11/821,347, filed Jun. 22, 2007.
U.S. Appl. No. 11/821,455, filed Jun. 22, 2007.
U.S. Appl. No. 11/652,169, filed Jan. 11, 2007.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/ abstract?CRETRY=1&SRETRY=0; [online] accessed: Sep. 22, 2008 (2 pages).
U.S. Appl. No. 12/008,266, filed Jan. 10, 2008.
U.S. Appl. No. 12/008,303, filed Jan. 10, 2008.
U.S. Appl. No. 12/031,610, filed Feb. 14, 2008.
Partial European Search Report, Application No. 08252150.1, dated Feb. 4, 2009 (4 pages).

* cited by examiner

END EFFECTOR CLOSURE SYSTEM FOR A SURGICAL STAPLING INSTRUMENT

BACKGROUND

The present application is related to the following commonly-owned U.S. Patent Applications filed concurrently herewith, and which are hereby incorporated by reference in their entirety:
(1) U.S. patent application Ser. No. 11/821,277, entitled SURGICAL STAPLING INSTRUMENTS,
(2) U.S. patent application Ser. No. 11/821,426, entitled SURGICAL STAPLING INSTRUMENT WITH AN ANTI-BACK UP MECHANISM,
(3) U.S. patent application Ser. No. 11/821,347, entitled SURGICAL STAPLING INSTRUMENT WITH A RETURN MECHANISM,
(4) U.S. patent application Ser. No. 11/821,455, entitled SURGICAL STAPLING INSTRUMENT WITH AN ARTICULATING END EFFECTOR.

1. Field of the Invention

The present invention generally relates to surgical stapling instruments and, more particularly, to surgical staplers having a closing system for closing an end effector and a firing system for deploying staples.

2. Description of the Related Art

As known in the art, surgical staplers are often used to deploy staples into soft tissue in order to reduce or eliminate bleeding from the soft tissue, especially as the tissue is being transected, for example. Surgical staplers, such as an endocutter, for example, can comprise an end effector which can be moved, or articulated, with respect to an elongate shaft assembly. End effectors are often configured to secure soft tissue between first and second jaw members where the first jaw member often includes a staple cartridge which is configured to removably store staples therein and the second jaw member often includes an anvil. Such surgical staplers can include a closing system for pivoting the anvil relative to the staple cartridge. These closing systems, however, do not prevent the end effector from being articulated relative to the shaft assembly after the jaw members have been closed. As a result, when the end effector is articulated, the end effector may apply a shear force to the soft tissue captured between the jaw members.

Surgical staplers, as outlined above, can be configured to pivot the anvil of the end effector relative to the staple cartridge in order to capture soft tissue therebetween. In various circumstances, the anvil can be configured to apply a clamping force to the soft tissue in order to hold the soft tissue tightly between the anvil and the staple cartridge. If a surgeon is unsatisfied with the position of the end effector, however, the surgeon must typically activate a release mechanism on the surgical stapler to pivot the anvil into an open position and then reposition the end effector. Thereafter, staples are typically deployed from the staple cartridge by a driver which traverses a channel in the staple cartridge and causes the staples to be deformed against the anvil and secure layers of the soft tissue together. Often, as known in the art, the staples are deployed in several staple lines, or rows, in order to more reliably secure the layers of tissue together. The end effector may also include a cutting member, such as a knife, for example, which is advanced between two rows of the staples to resect the soft tissue after the layers of the soft tissue have been stapled together.

After the driver and the cutting member have been advanced within the end effector, it is often necessary to retract the driver and/or cutting member to their starting positions. Previous surgical staplers have included a return spring which retracts the cutting member relative to the staple cartridge after a release button or toggle switch on the surgical stapler has been actuated by the surgeon, for example. In various embodiments, a first end of the return spring can be connected to the housing of the surgical instrument and a second end of the spring can be connected to the cutting member. Such staplers, however, are often difficult to use as the force required to extend the return spring as the cutting member is advanced is often significant. Furthermore, such return springs often apply a biasing force to the cutting member as it is advanced which can, in various circumstances, prematurely return the cutting member, especially in embodiments where multiple strokes of a trigger are required to completely advance the cutting member. What is needed is an improvement over the foregoing.

SUMMARY

In at least one form of the invention, a surgical instrument can include a shaft assembly, an end effector movable relative to the shaft assembly, and a locking mechanism configured to engage the shaft assembly and/or the end effector in order to fix, or lock, the relative relationship between the shaft assembly and the end effector. In various embodiments, the end effector can include an anvil and a channel where the channel can be configured to receive a staple cartridge and the anvil can be movably coupled to the channel. In at least one embodiment, the surgical instrument can further include a closure system configured to generate a closing motion where the anvil can be responsive to the closing motion. In various embodiments, the closure system can be further configured to engage the locking mechanism and prevent the locking mechanism from unlocking the relative relationship between the shaft assembly and the end effector.

In at least one form of the invention, a surgical instrument can include a closure system configured to move an anvil of an end effector, for example, between an open position, a partially closed position, and a closed position. In various embodiments, the surgical instrument can further include a lock member configured to selectively engage and lock the closure system when the anvil is positioned in one of its partially closed and closed positions. In at least one embodiment, the surgical instrument can include a trigger configured to pivot the anvil, for example, where the trigger can include a cam surface and a first notch in the cam surface. In various embodiments, the lock member can include a follower portion and the closure drive can include a lock spring configured to bias the follower portion against the cam surface of the trigger such that the follower portion can engage the first notch of the trigger when the anvil is pivoted into its partially closed position. In at least one embodiment, when the follower portion is engaged with the first notch, the first notch can prevent the anvil from being pivoted into its open position. In various embodiments, the cam portion can further include a second notch and the follower portion can be configured to engage the second notch when the anvil is pivoted into its closed position.

In at least one form of the invention, a surgical instrument can include a firing drive comprising a firing member configured to advance a cutting member within an end effector, for example, and a flexible band connected to the firing member configured to retract the firing member. In at least one embodiment, the surgical instrument can include a brake configured to engage the band, for example, and thereby limit the movement of the firing member. In various embodiments, the firing drive can further include a reel configured to wind up at least a portion of the band when the firing member is retracted. In at least one embodiment, the firing drive can further include a trigger selectively engageable with the firing member and the reel such that, when the trigger is operably engaged with the firing member, an actuation of the trigger can be configured to advance the firing member, and, when the trigger is operably engaged with the reel, an actuation of the trigger can be configured to rotate the reel and retract the firing member via the band.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 3:
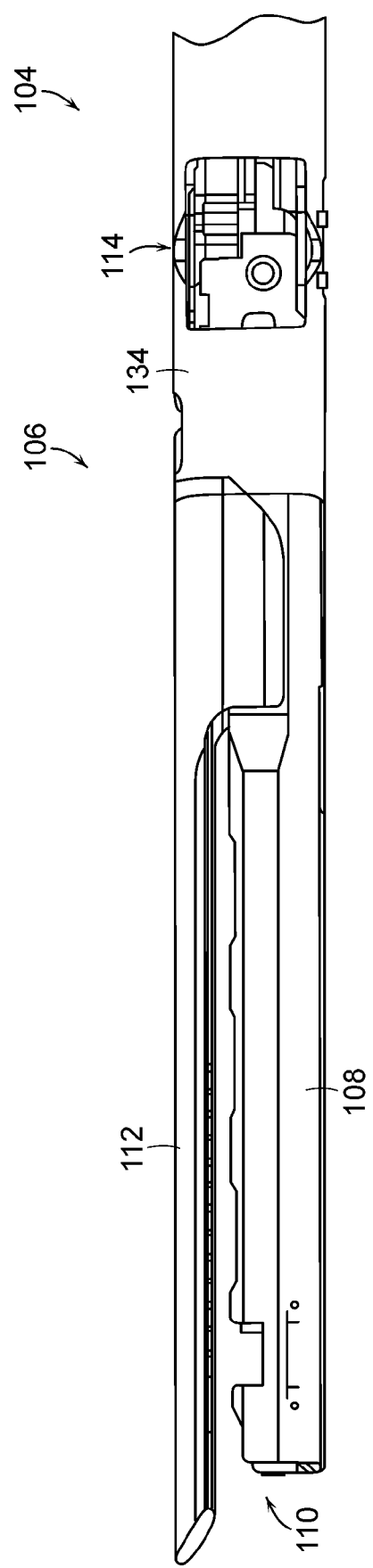
FIG. 3 is an elevational view of an end effector of the surgical instrument of FIG. 1.
Figure 4:
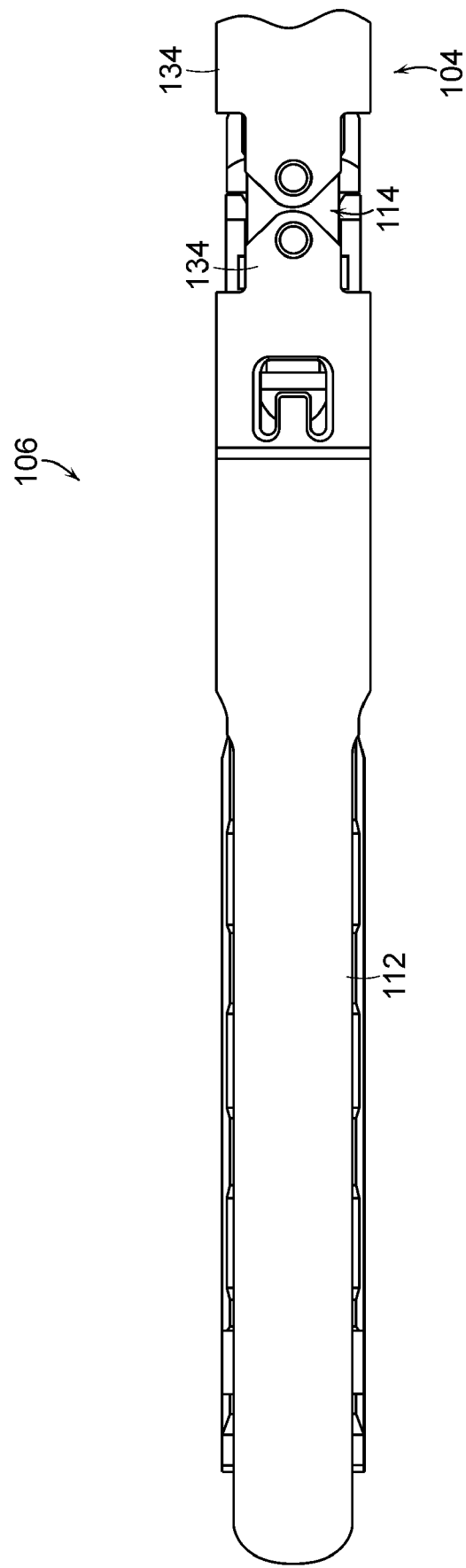
FIG. 4 is a top view of the end effector of FIG. 3.

In various embodiments, a surgical instrument in accordance with the present invention can be configured to insert surgical staples into soft tissue, for example. In at least one embodiment, referring to FIGS. 1-4, surgical instrument 100 can include handle portion 102, elongate shaft assembly 104, and end effector 106. In various embodiments, referring to FIGS. 3 and 4, end effector 106 can include staple cartridge channel 108 and staple cartridge 110, where staple cartridge 110 can be configured to removably store staples therein. In at least one embodiment, end effector 106 can further include anvil 112 which can be pivotably connected to staple cartridge channel 108 and can be pivoted between open and closed positions by an end effector closure system. In order to deploy the staples from staple cartridge 110, surgical instrument 100 can further include a staple driver configured to traverse staple cartridge 110 and a firing drive configured to advance the staple driver within the staple cartridge. In various embodiments, anvil 112 can be configured to deform at least a portion of the staples as they are deployed from the staple cartridge. Although various embodiments of an end effector closure system and a firing drive are described in further detail below, several embodiments of end effector closure systems and firing drives are disclosed in U.S. Pat. No. 6,905,057, entitled SURGICAL STAPLING INSTRUMENT INCORPORATING A FIRING MECHANISM HAVING A LINKED RACK TRANSMISSION, which issued on Jun. 14, 2005, and U.S. Pat. No. 7,044,352, entitled SURGICAL STAPLING INSTRUMENT HAVING A SINGLE LOCKOUT MECHANISM FOR PERVENTION OF FIRING, which issued on May 16, 2006, the entire disclosures of which are hereby incorporated by reference herein.

In various embodiments, a surgical instrument in accordance with the present invention can include a system for moving, or articulating, an end effector relative to an elongate shaft assembly of the surgical instrument. In at least one embodiment, referring to FIGS. 3-7, surgical instrument 100 can include articulation joint 114 which can movably connect end effector 106 and elongate shaft assembly 104. In various embodiments, articulation joint 114 can permit end effector 106 to be moved relative to shaft assembly 104 in a single plane or, alternatively, multiple planes. In either event, articulation joint 114 can include one or more pivot axes 116 (FIG. 5) about which end effector 106 can be articulated. In various embodiments, referring to FIGS. 5 and 6, surgical instrument 100 can further include locking mechanism 118 which can fix, or lock, the relative relationship between end effector 106 and elongate shaft assembly 104. In at least one embodiment, locking mechanism 118 can include lock member 120 which can be slid relative to end effector 106 and engage end effector 106 in order to prevent, or at least partially inhibit, relative movement between end effector 106 and shaft assembly 104. In at least one embodiment, lock member 120 can be configured to engage at least one of teeth 312 (FIGS. 5 and 6) of end effector 106 such that the interaction between lock member 120 and teeth 312 can prevent, or at least partially inhibit, end effector 106 from rotating about axis 116 as described in greater detail further below.

Figure 6:
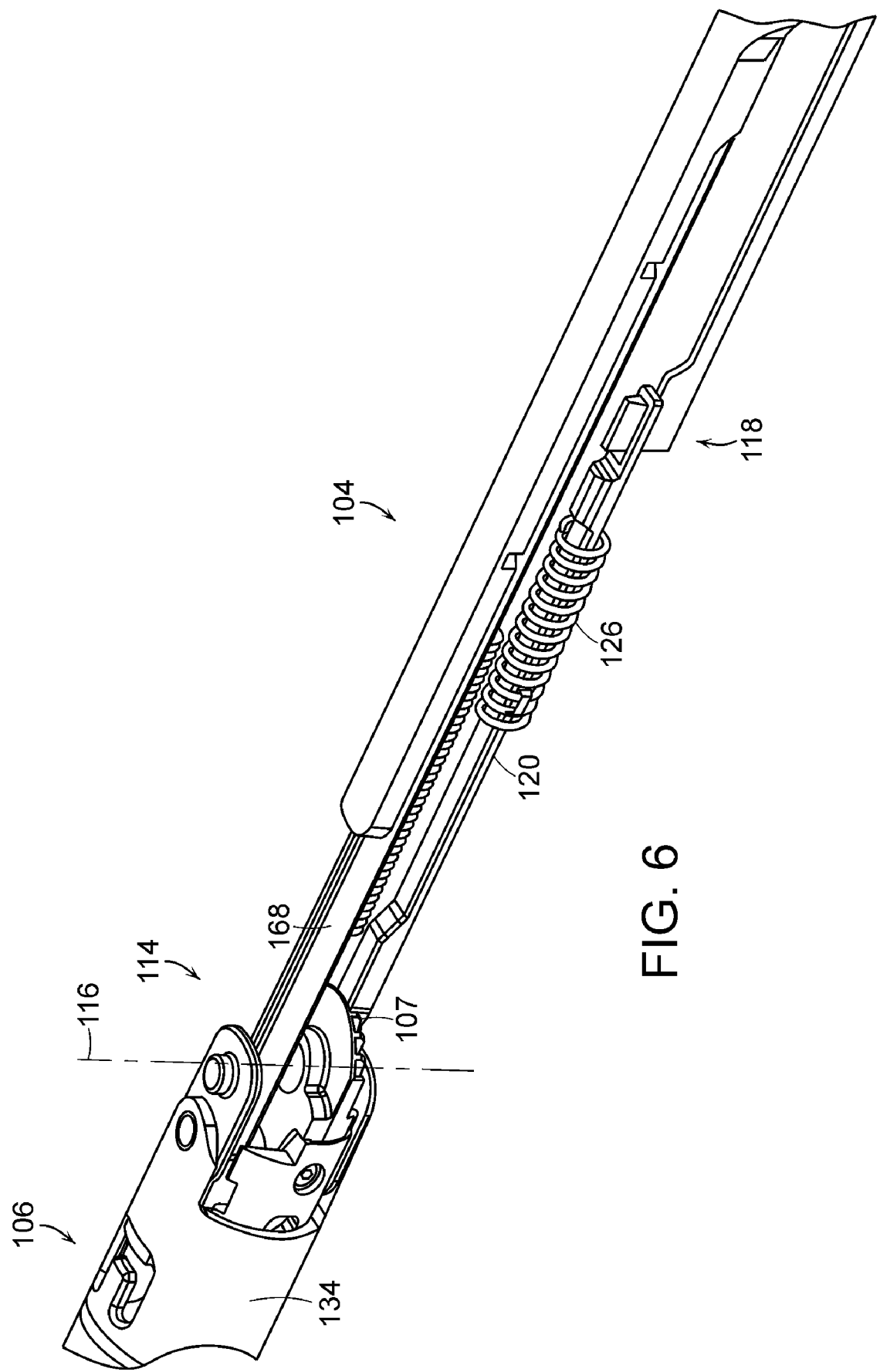
FIG. 6 is a perspective view of an elongate shaft assembly and the articulation joint of the surgical instrument of FIG. 1 with some components of the surgical instrument removed.
Figure 7:
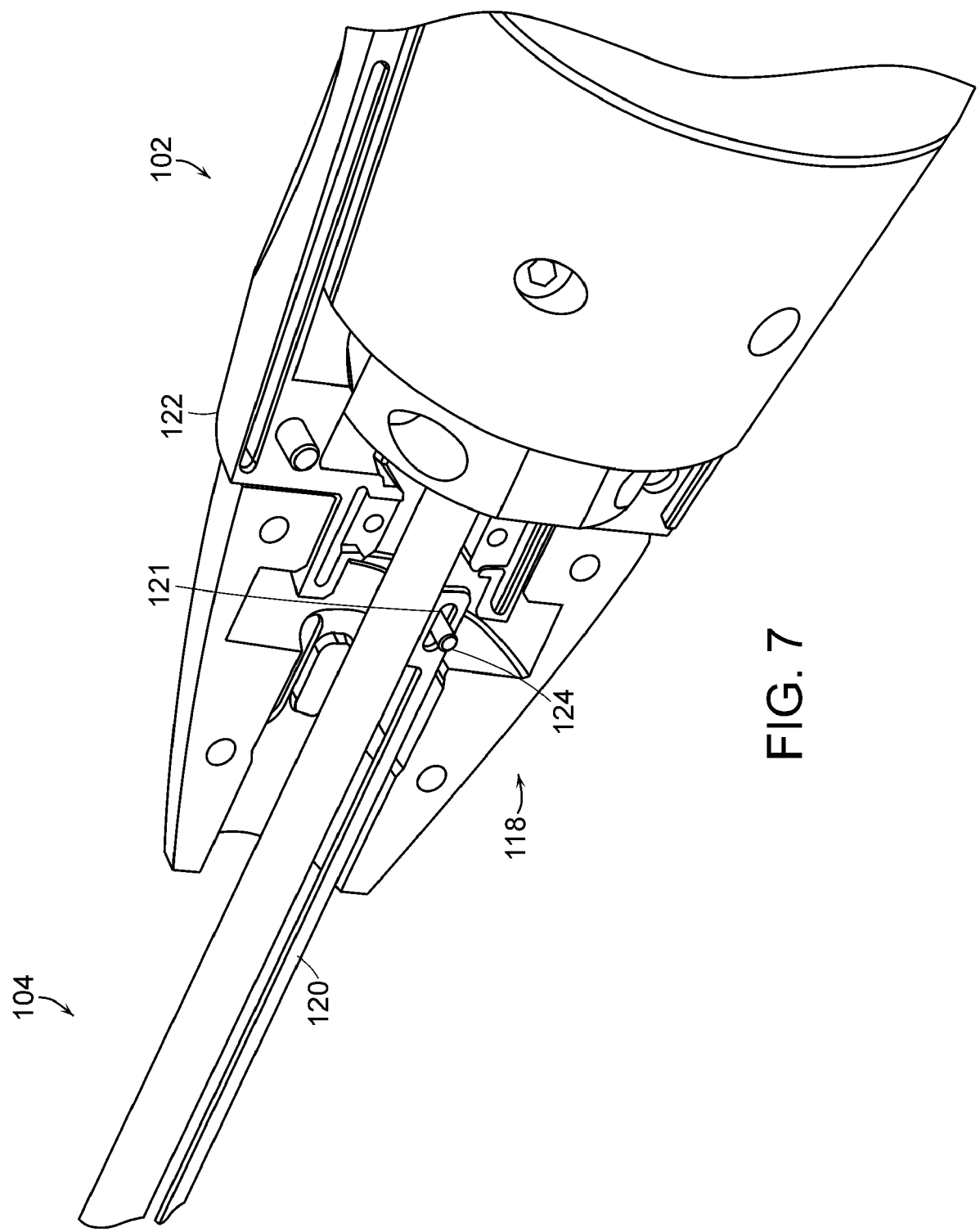
FIG. 7 is a partial perspective view of the handle portion and the elongate shaft assembly of the surgical instrument of FIG. 1 with some components of the surgical instrument removed.
Figure 8:
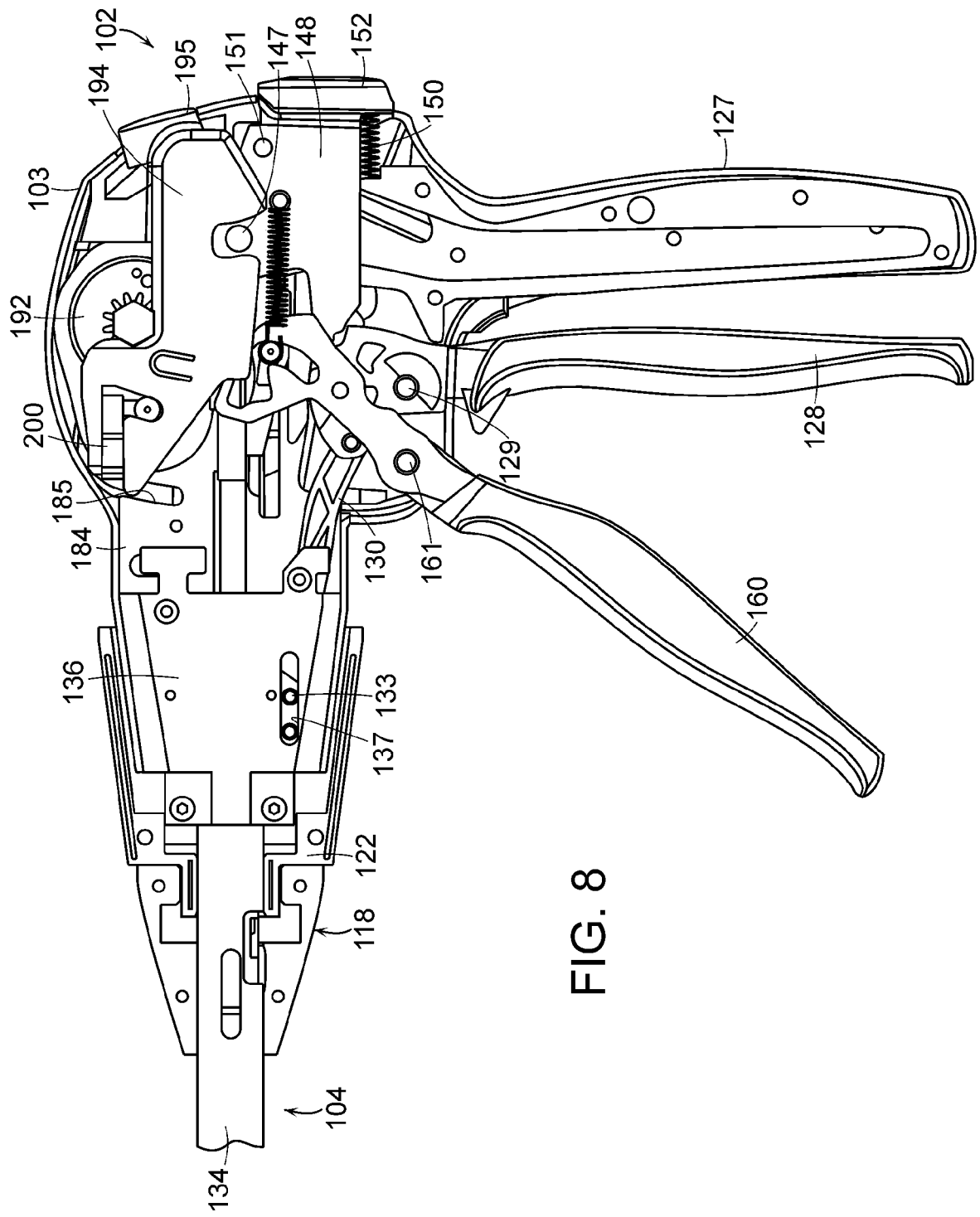
FIG. 8 is an elevational view of the handle portion of FIG. 2 with some components of the surgical instrument removed.
Figure 9:
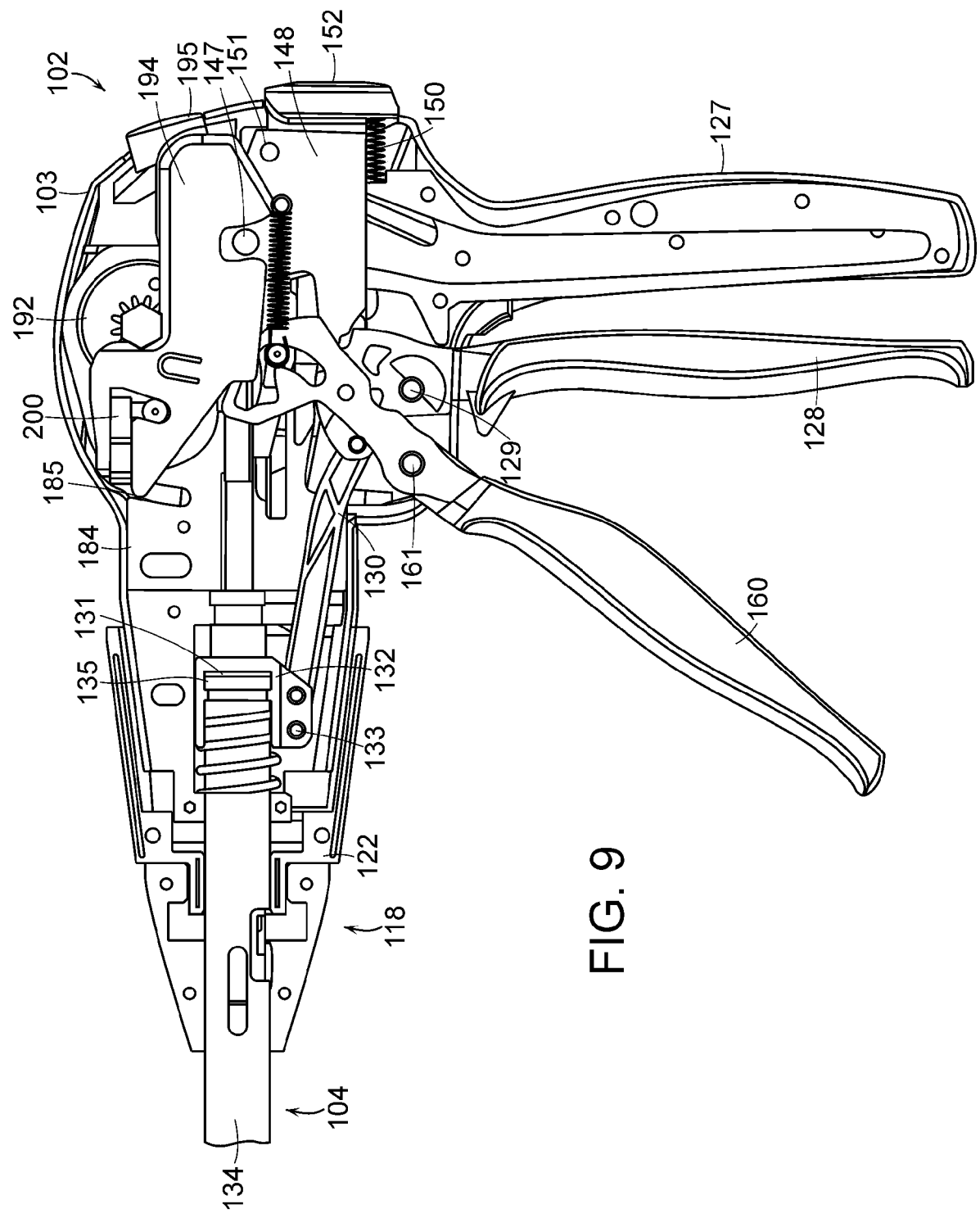
FIG. 9 is an elevational view of the handle portion of FIG. 2 with additional components of the surgical instrument removed.

In various embodiments, referring to FIGS. 7-9, locking mechanism 118 can further include actuator 122 which can be operably connected to lock member 120. In at least one embodiment, actuator 122 can include pin 124 which can be received within slot 121 in lock member 120 such that, when actuator 122 is slid relative to handle portion 102, pin 124 can abut a side wall of slot 121 and motivate lock member 120 relative to end effector 106. In at least one embodiment, actuator 122 can be pulled away from end effector 106, i.e., proximally, to disengage lock member 120 from end effector 106. Although not illustrated, other embodiments are envisioned where actuator 122 can be moved distally, or even rotated, in order to disengage lock member 120 from end effector 106. In either event, locking mechanism 118 can further include return spring 126 (FIG. 6) which can be configured to move lock member 120 toward end effector 106, i.e., distally, to engage lock member 120 with end effector 106 after actuator 122 has been released. Other locking mechanisms are disclosed in U.S. patent application Ser. No. 11/100,772, entitled SURGICAL INSTRUMENT WITH ARTICULATING SHAFT WITH SINGLE PIVOT CLOSURE AND DOUBLE PIVOT FRAME GROUND, which was filed on Apr. 7, 2005, U.S. patent application Ser. No. 11/238,358, entitled SURGICAL INSTRUMENT WITH ARTICULATING SHAFT WITH RIGID FIRING BAR SUPPORTS, which was filed on Sep. 29, 2005, and U.S. patent application Ser. No. 11/491,626, entitled SURGICAL STAPLING AND CUTTING DEVICE AND METHOD FOR USING THE DEVICE, which was filed on Jul. 24, 2006, the entire disclosures of which are hereby incorporated by reference herein.

Figure 1:
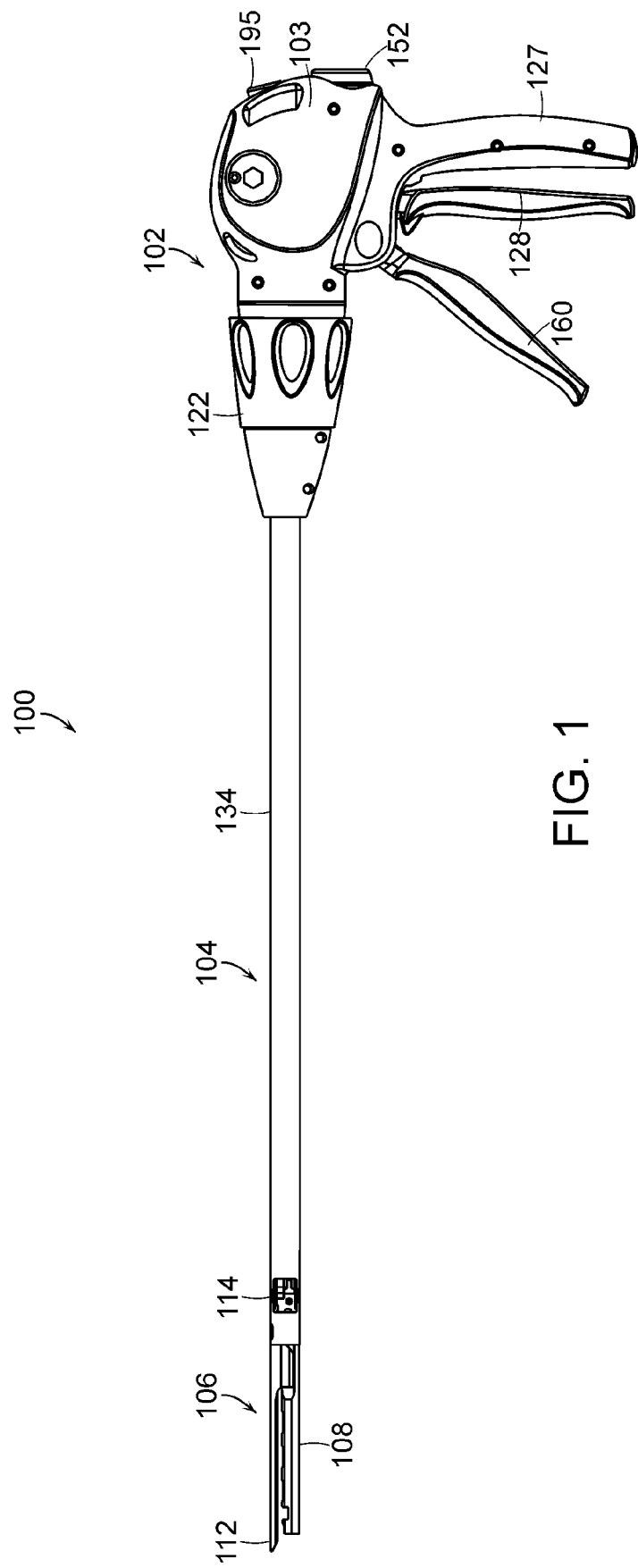
FIG. 1 is an elevational view of a surgical instrument in accordance with an embodiment of the present invention.
Figure 2:
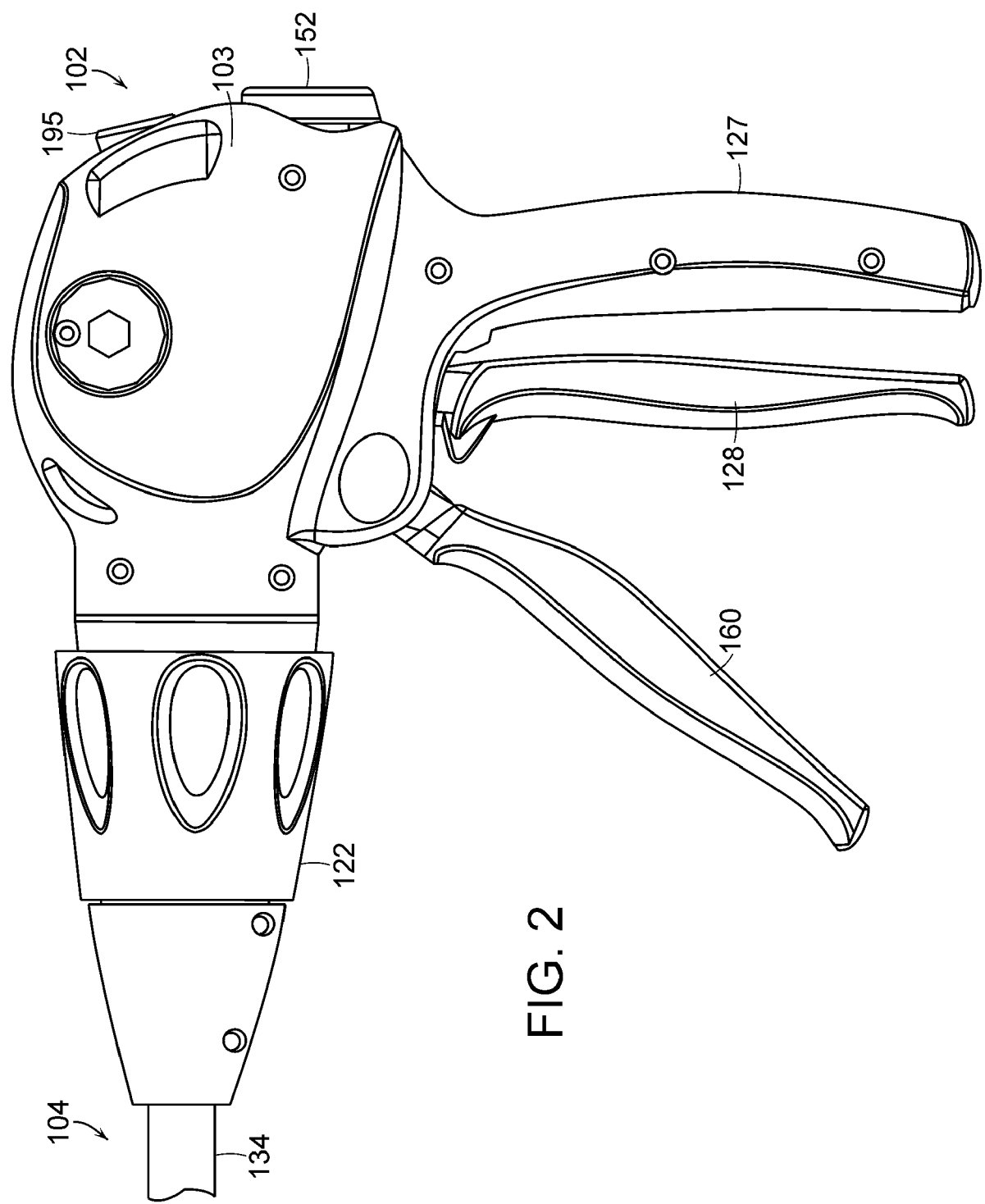
FIG. 2 is an elevational view of a handle portion of the surgical instrument of FIG. 1.

In various embodiments, referring to FIGS. 1 and 2, actuator 122 can be contoured such that a surgeon can grasp the outer surface of actuator 122 and pull actuator 122 proximally as described above. To move actuator 122, in at least one embodiment, a surgeon may place one hand on handle grip 127, for example, and place their other hand on actuator 122 so that the surgeon can move actuator 122 relative to handle grip 127. In other various embodiments, referring to FIGS. 10-13, actuator 122' can be configured such that a surgeon may only need one hand to operate the surgical instrument. More particularly, in at least one embodiment, actuator 122' can include hooks, or projections, 115 extending therefrom which can allow the surgeon to hold handle grip 127 with one hand and extend at least one finger from that hand distally to grip at least one projection 115 and pull actuator 122' proximally as described above. While actuator 122' is described herein as having projections 115, actuator 122, or any other suitable actuator, can also include projections 115 and/or any other suitable features that can assist a surgeon in operating surgical instrument 100 with one hand. In at least one embodiment, projections 115 can be at least partially comprised of and/or coated with an elastic or 'soft-touch' material which can improve the surgeon's grip on projections 115 and can provide other ergonomic benefits to the surgeon. In various embodiments, actuator 122', for example, can be operably engaged with shaft assembly 104 such that end effector 106 and shaft assembly 104 can be rotated about a longitudinal axis by actuator 122'. In such embodiments, a surgeon can orient end effector 106 in a surgical site by articulating end effector 106 as described above and/or rotating end effector 106 into position. In at least one embodiment, the surgeon can rotate actuator 122' by positioning a finger against one of projections 115 and applying a force thereto. In various embodiments, the surgeon can hold actuator 122' in position by placing a finger against a projection 115 and resisting any undesired motion of actuator 122' and, correspondingly, end effector 106.

Figure 5:
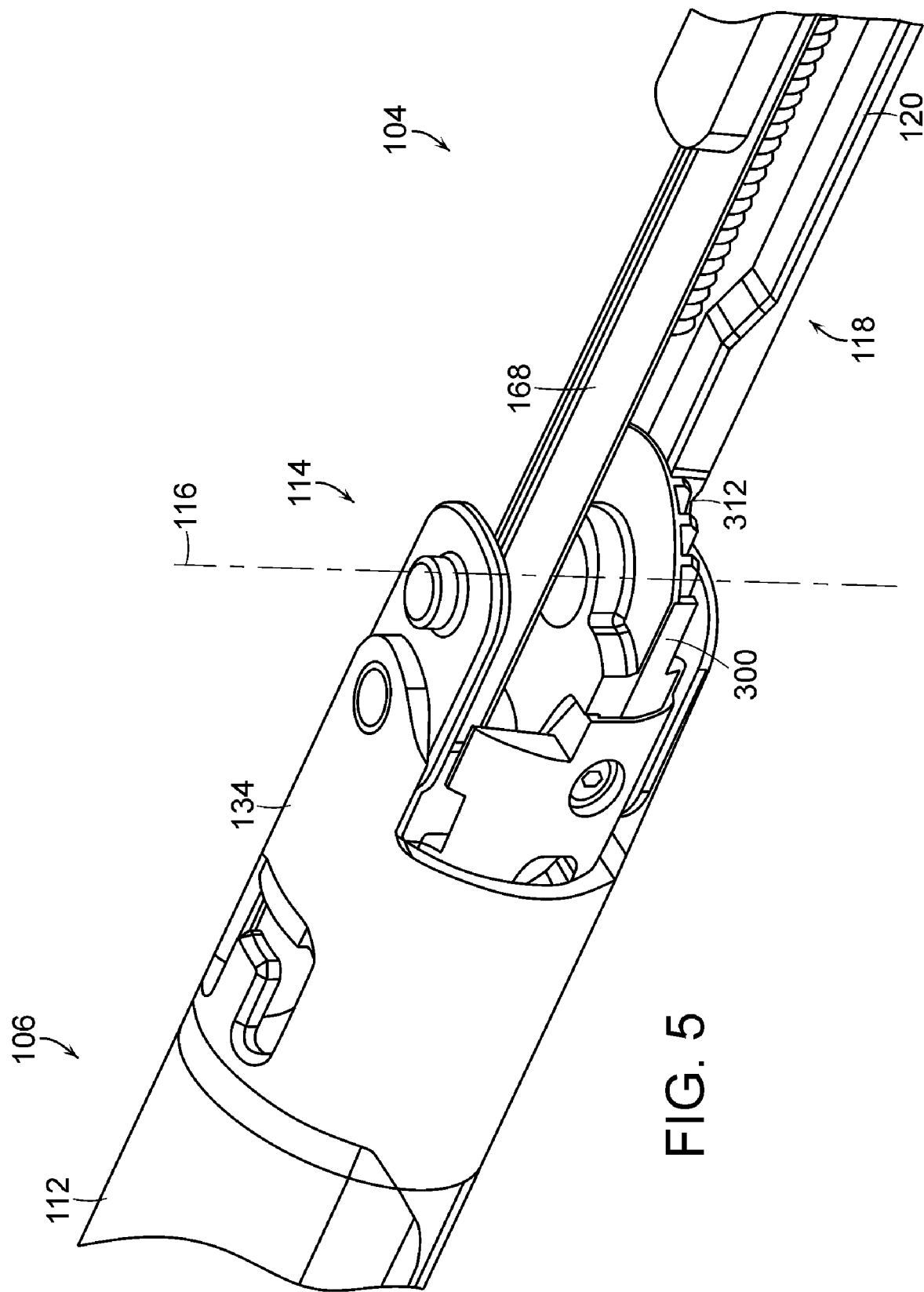
FIG. 5 is a perspective view of an articulation joint of the surgical instrument of FIG. 1 with some components of the surgical instrument removed.

In various embodiments, a surgical instrument in accordance with the present invention can include a system for closing, or clamping, an end effector onto soft tissue, for example. In at least one embodiment, referring to FIGS. 2, 5, 8 and 9, surgical instrument 100 can include closure trigger 128, drive link 130, driver 132, and closure tube 134. In various embodiments, upon an actuation of closure trigger 128, closure trigger 128 can be configured to displace drive link 130, driver 132, and closure tube 134 distally. More particularly, in at least one embodiment, drive link 130 can include a first end pivotably connected to trigger 128 and a second end pivotably connected to driver 132 such that the rotation of trigger 128 toward handle grip 127 can drive link 130 forward and slide driver 132 along an axis defined by driver guide 136 (FIG. 8). In various embodiments, driver 132 can include projections 133 extending therefrom which can be slidably received within slots 135 in driver guide 136 such that slots 135 can define a path for driver 132 as it is moved. In various embodiments, closure tube 134 can be operably engaged with driver 132 such that, when driver 132 is moved distally as described above, closure tube 134 can engage anvil 112 and pivot anvil 112 downwardly. Referring primarily to FIG. 5, closure tube 134 can be configured to slide over articulation joint 114 and pivot anvil 112 relative to staple cartridge 110. In at least one embodiment, as illustrated in FIG. 9, closure tube 134 can include a proximal end having projection 135 extending therefrom which can be received in slot 131 in driver 132 such that the displacement of driver 132 is transmitted to closure tube 134.

Figure 10:
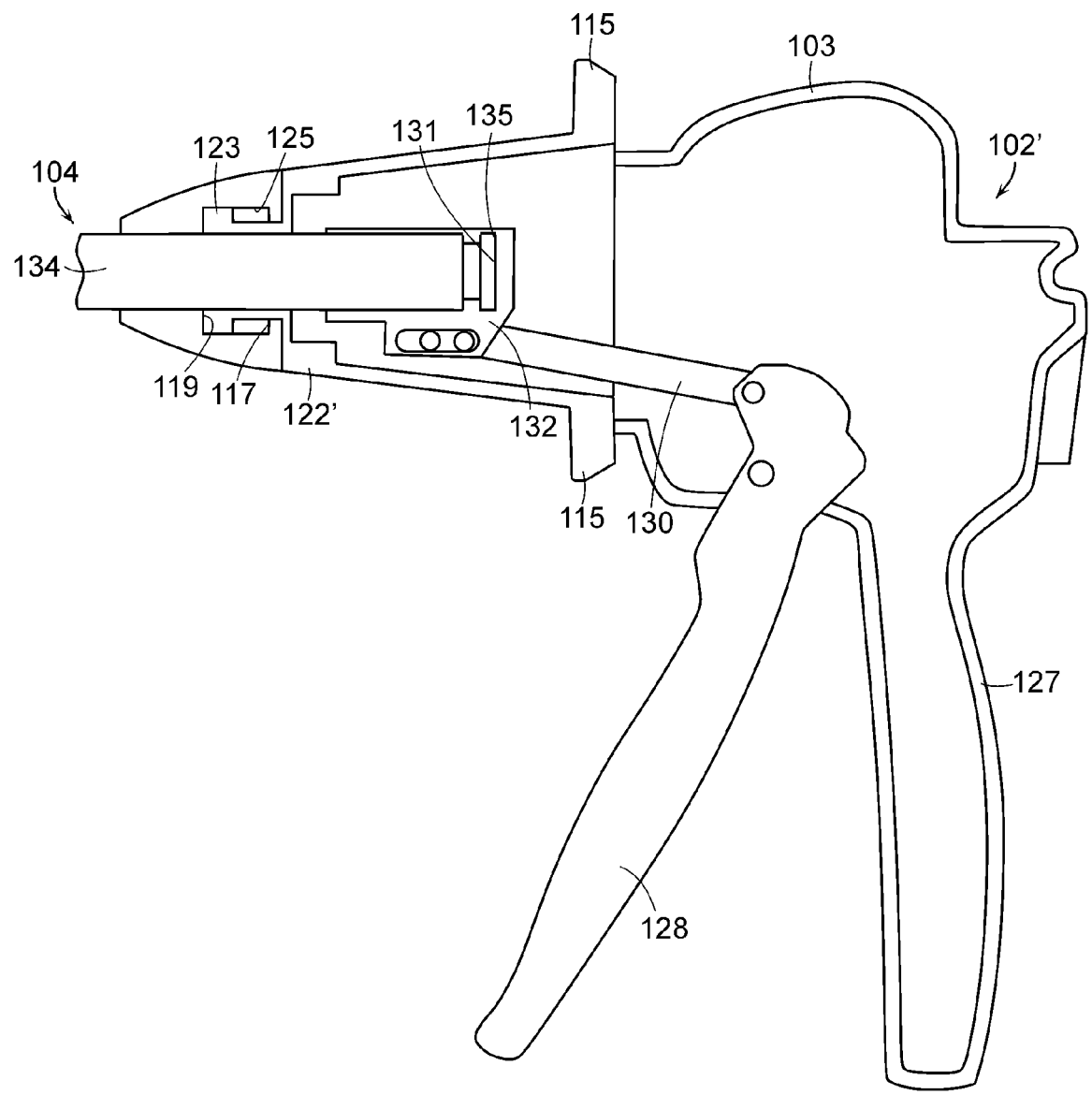
FIG. 10 is an elevational view of an actuator of an articulation locking mechanism and an end effector closure system of a surgical instrument in accordance with an alternative embodiment of the present invention with some components of the surgical instrument removed.
Figure 11:
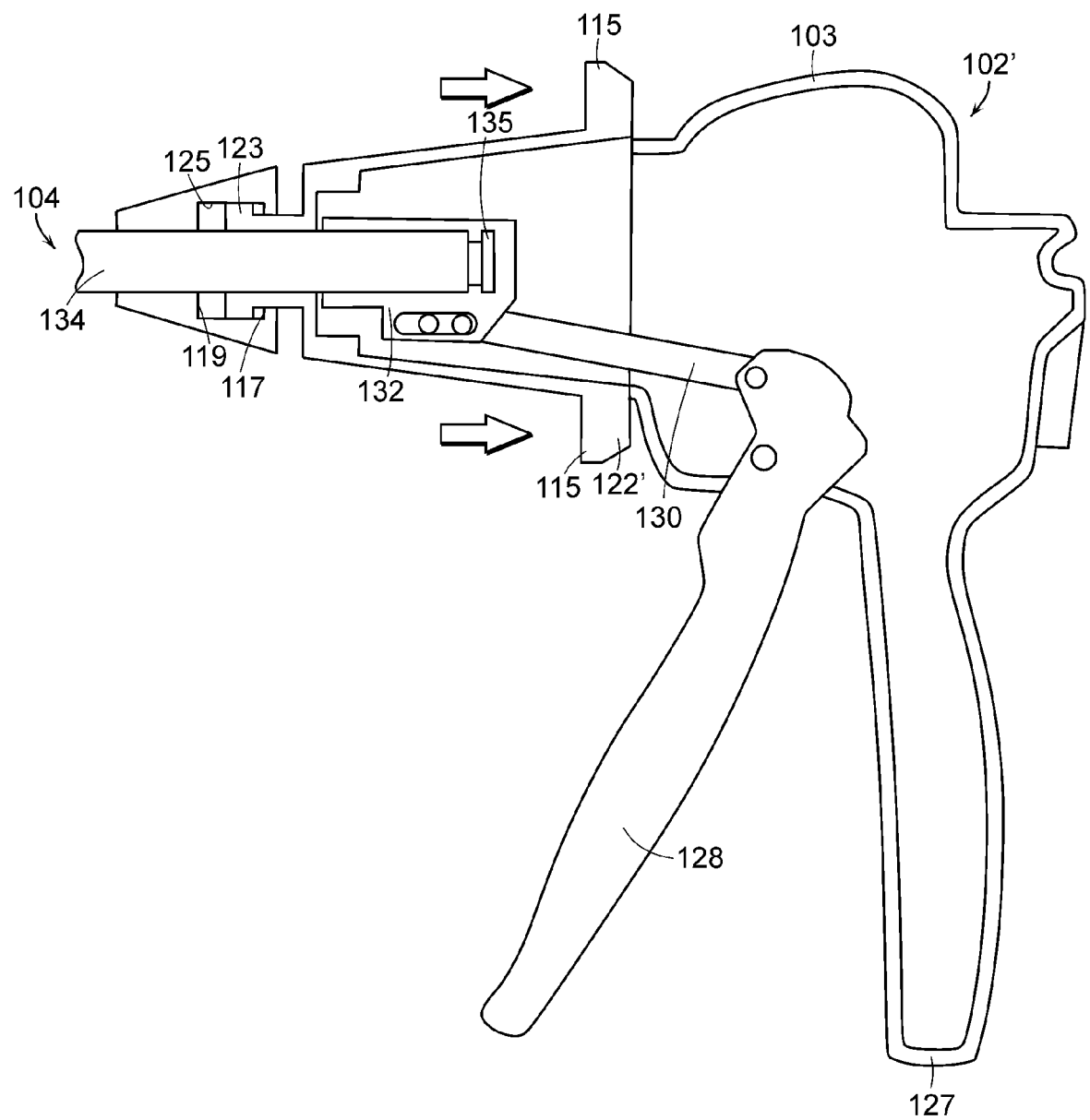
FIG. 11 is an elevational view of the surgical instrument of FIG. 10 illustrating the articulation locking mechanism actuator in an unlocked position and the end effector closure system in an open configuration.
Figure 12:
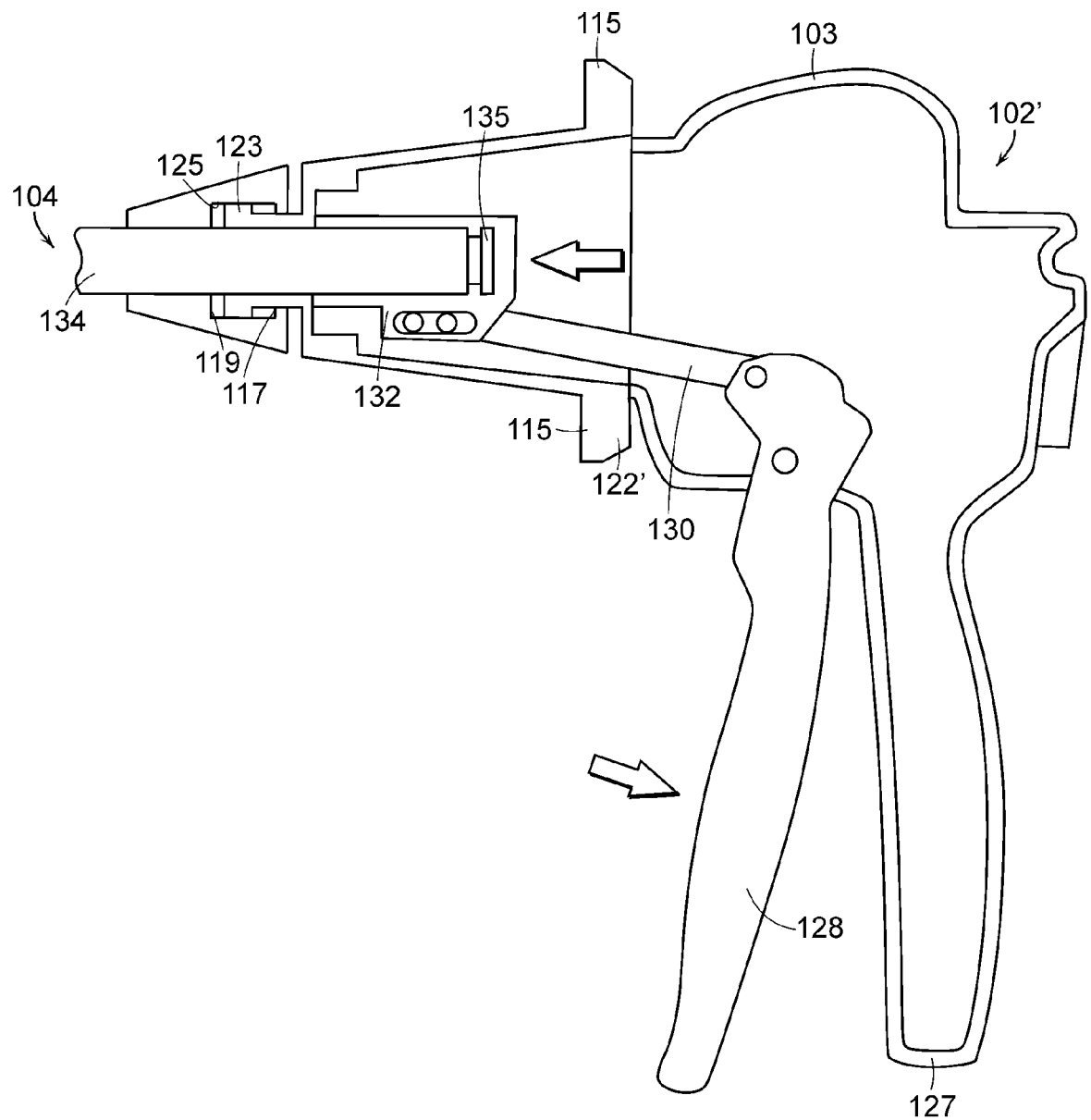
FIG. 12 is an elevational view of the surgical instrument of FIG. 10 illustrating the articulation locking mechanism actuator in an unlocked position and the end effector closure system in a partially closed configuration.

In various embodiments, as described above, locking mechanism 118 can prevent, or at least partially inhibit, relative movement between end effector 106 and shaft assembly 104. In circumstances where soft tissue is clamped between anvil 112 and staple cartridge 110, for example, relative movement between end effector 106 and shaft assembly 104 can apply a shear force to the soft tissue clamped therebetween which may damage it. In various embodiments, referring to FIGS. 10-13, in order to prevent, or at least reduce, relative movement between end effector 106 and shaft assembly 104 when end effector 106 is closed, the end effector closure system can be configured to engage locking mechanism 118 to prevent actuator 122' from being moved into its unlocked position. In effect, in at least one embodiment, the actuation of closure trigger 128 can not only close end effector 106, but it can also prevent locking mechanism 118 from being unlocked. In various embodiments, referring to FIGS. 10-13, surgical instrument 100' can include driver 132 which can be configured to abut, or be positioned closely adjacent to, actuator 122' when driver 132 is moved distally by trigger 128 and thereby prevent actuator 122' from being moved proximally as described above with respect to actuator 122. More particularly, before trigger 132 is actuated, as illustrated in FIGS. 10 and 11, actuator 122' can be slid proximally in order to slide lock member 120 relative to end effector 106 and unlock articulation joint 114. Upon an actuation of trigger of 132, however, referring to FIG. 13, driver 132 can be configured to abut, or be positioned adjacent to, actuator 122' such that actuator 122' cannot be moved proximally to disengage lock member 120 from end effector 106. As a result, the end effector closure system can prevent end effector 106 from being articulated after it has been closed, thereby reducing the possibility that a shear force will be transmitted to the soft tissue clamped therein.

Further to the above, the end effector closure system can provide feedback to the surgeon that the end effector has been closed and, in order for the surgeon to unlock and articulate the end effector, the surgeon must first at least partially re-open the end effector before the end effector can be articulated. More particularly, owing to the interaction between driver 132 and actuator 122' when end effector 106 is closed, when a surgeon attempts to pull actuator 122' proximally to unlock articulation joint 114, driver 132 can substantially prevent actuator 122' from moving thereby signaling to the surgeon that end effector 106 is closed and end effector 106 must first be opened before actuator 122' can be moved and the articulation joint can be unlocked. In various embodiments, such an end effector closure system can prevent the surgeon from damaging the surgical instrument and/or tissue captured within, or surrounding, the end effector. More particularly, in at least one embodiment, when closure tube 134 has been advanced to close anvil 112 as described above, closure tube 134 may apply a force to anvil 112 to maintain anvil 112 in a closed position and, in various circumstances, this force can create friction forces within articulation joint 114 which can inhibit, if not prevent, end effector 106 from rotating about articulation joint 114. In embodiments without the end effector closure system described above, if a surgeon attempts to overcome these friction forces without first at least partially opening the end effector, the surgeon may bend or break one or more components of the surgical instrument, for example. In various embodiments of the present invention, however, driver 132, for example, may prevent the surgeon from releasing articulation lock 120 as described above and, as a result, the surgeon may not be afforded the opportunity to unlock articulation joint 114 let alone articulate end effector 106.

In various embodiments, a surgical instrument in accordance with the present invention can include an end effector closure system which can position anvil 112, for example, in an open position, a closed position, and a partially closed position. In at least one embodiment, a surgeon can move an anvil 112 into a partially closed position and evaluate whether the end effector should be repositioned or articulated before anvil 112 is moved into its closed position. In such embodiments, anvil 112 can be moved relative to soft tissue positioned intermediate anvil 112 and staple cartridge 110 without applying a shear force, or at least a substantial shear force, to the soft tissue before anvil 112 is completely closed. In at least one embodiment, anvil 112 can be configured such that it does not clamp the soft tissue positioned between anvil 112 and staple cartridge 110 when it is in its partially closed position. Alternatively, anvil 112 can be configured to apply a light clamping force to the soft tissue when anvil 112 is in its partially closed position before applying a larger clamping force when it is moved into its closed position. In at least one such embodiment, the surgical instrument can include a trigger which can be moved between a first position (FIG. 11) which corresponds to the open position of anvil 112, a second position (FIG. 12) which corresponds with its partially closed position, and a third position (FIG. 13) which corresponds with its closed position. In various embodiments, referring to FIGS. 8 and 9, trigger 128 can be pivotably mounted to housing 103 of handle portion 102 such that trigger 128 can be rotated about pin 129 between its first, second, and third positions. In various embodiments, referring to FIGS. 8, 9, 17 and 18, surgical instrument 100 can further include trigger lock 148 which can be configured to engage trigger 128 and selectively lock trigger 128 in at least one of its first, second, and third positions described above. In at least one embodiment, trigger 128 can include pivot end 138 comprising cam surface 140, first notch 142, and second notch 144 where trigger lock 148 can be configured to engage first notch 142 and second notch 144. More particularly, surgical instrument 100 can further include, referring to FIGS. 8 and 9, trigger lock spring 150 which can be configured to bias follower portion 149 of trigger lock 148 against cam surface 140 such that when either first notch 142 or second notch 144 is aligned with follower portion 149, trigger lock spring 150 can push follower portion 149 into first notch 142 or second notch 144, respectively. In at least one embodiment, referring primarily to FIGS. 8 and 9, trigger lock 148 can be pivotably mounted to housing 103 of handle portion 102 via pin 151. In various embodiments, trigger lock spring 150 can be compressed intermediate button portion 152 of trigger lock 148 and housing 103 such that trigger lock spring 150 can rotate trigger lock 148 about pin 151 and bias trigger lock 148 downwardly against cam surface 140 of trigger 128.

Further to the above, in at least one embodiment, first notch 142 can be aligned with follower portion 149 when trigger 132 is moved into its second position and anvil 112 is moved into its partially closed position. In various embodiments, follower portion 149 can be securely retained within first notch 142 such that trigger lock 148 may need to be manually disengaged from trigger 132 before trigger 132 can be moved into its third position and/or returned to its first position. In at least one embodiment, referring to FIGS. 8 and 9, a surgeon can depress button portion 152 of lock member 148 such that lock member 148 is rotated about pin 151 and follower portion 149 is lifted upwardly and out of engagement with trigger 128. In other various embodiments, first notch 142 can be configured such that follower portion 149 can slide out of first notch 142 upon an application of force to trigger 132. In either event, after follower portion 149 has been disengaged from first notch 142, a surgeon can selectively move trigger 132 into its third position or release trigger 132 and allow a trigger spring, for example, to return trigger 132 to its first position. In at least one alternative embodiment, first notch 142 and follower portion 149 can be configured such that, after trigger 132 has been moved into its second position, trigger 132 must be moved into its third position before it can be returned into its first position. In either event, in at least one embodiment, second notch 144 of trigger 132 can be aligned with follower portion 149 when trigger 132 is moved into its third position and anvil 112 is moved into its closed position. Similar to first notch 142, second notch 144 can be configured to retain follower portion 149 therein until lock member 148 is disengaged from trigger 132 and/or a sufficient force is applied to trigger 132 to dislodge follower portion 149 from second notch 144. Thereafter, in various embodiments, a trigger spring can move trigger 132 from its third position into its second position where the surgeon may be required to, similar to the above, disengage follower portion 149 from first notch 142. In at least one alternative embodiment, first notch 142 can be configured such that follower portion 149 can slide past first notch 142 and allow trigger 132 to be moved from its third position to its first position without requiring the surgeon to dislodge follower portion 149 from first notch 142.

Further to the above, although not illustrated, button portion 152 of lock member 148 can be recessed, for example, within surgical instrument housing 103 when closure trigger 128 is in its first position. In alternative embodiments, button portion 152 can be positioned flushly with housing 103 or it can extend slightly from housing 103. In either event, in at least one embodiment, button portion 152 can move outwardly relative to housing 103 when closure trigger 128 is moved into its second position. Such movement can provide visual feedback to the surgeon that the anvil of the surgical instrument is in its partially closed position. In addition, the movement of button portion 152 can also be accompanied by audio and/or tactile feedback. In either event, a surgeon can access button portion 152 after it has been moved outwardly such that lock member 148 can be disengaged from trigger 128 as described above. In various embodiments, button portion 152 can move outwardly even further when trigger 128 is moved from its second position to its third position. Similar to the above, such movement can provide a visual cue to the surgeon that the anvil is now in its closed position and can be accompanied by audio and/or tactile feedback, as described above. Although button 152 is described above as moving outwardly as trigger 128 is progressed between its first and third positions, the invention is not so limited. On the contrary, button 152, or any other suitable indicator, can be provide feedback to the surgeon in any suitable manner.

In alternative embodiments, although not illustrated, anvil 112 can be held, or retained, in more than the three positions described above, i.e., its open, closed, and partially-closed positions. In at least one embodiment, anvil 112 can be retained in open, closed, and two or more intermediate positions. In such embodiments, anvil 112 could be progressed through these intermediate positions and apply an increasingly greater force to the soft tissue captured in end effector 106 as anvil 112 is moved toward its closed position. In at least one embodiment, similar to the above, trigger 132 could include a plurality of notches which could correspond with the various intermediate positions of anvil 112. In various alternative embodiments, although not illustrated, the end effector closure system could include a ratchet assembly which could allow trigger 132 and, correspondingly, anvil 112 to be held in a plurality of positions. In such embodiments, anvil 112 and trigger 132 could be held in place by a pawl pivotably engaged with a ratchet wheel operably engaged with trigger 132.

Figure 13:
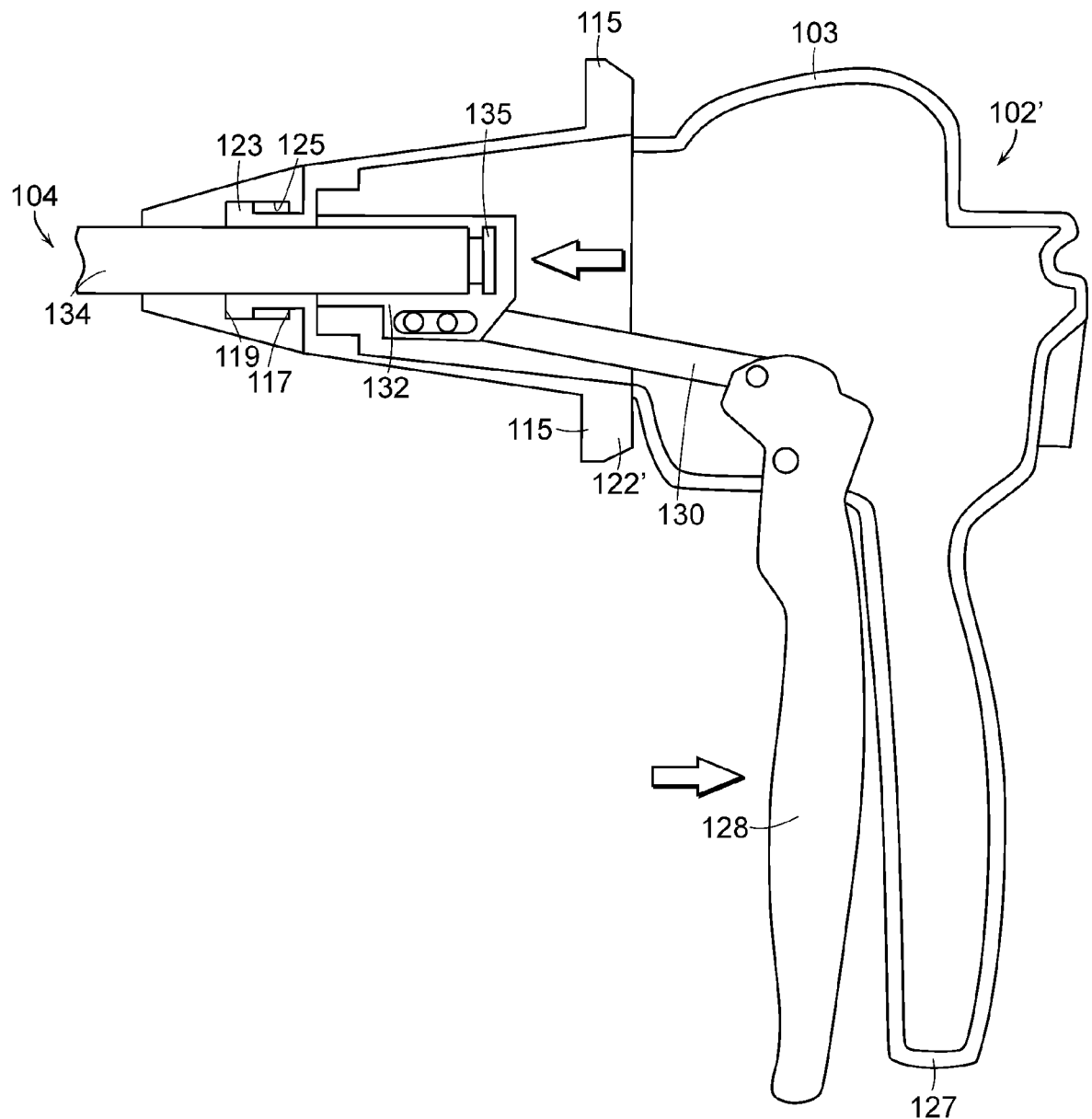
FIG. 13 is an elevational view of the surgical instrument of FIG. 10 illustrating the articulation locking mechanism actuator in a locked position and the end effector closure system in a closed configuration.
Figure 14:
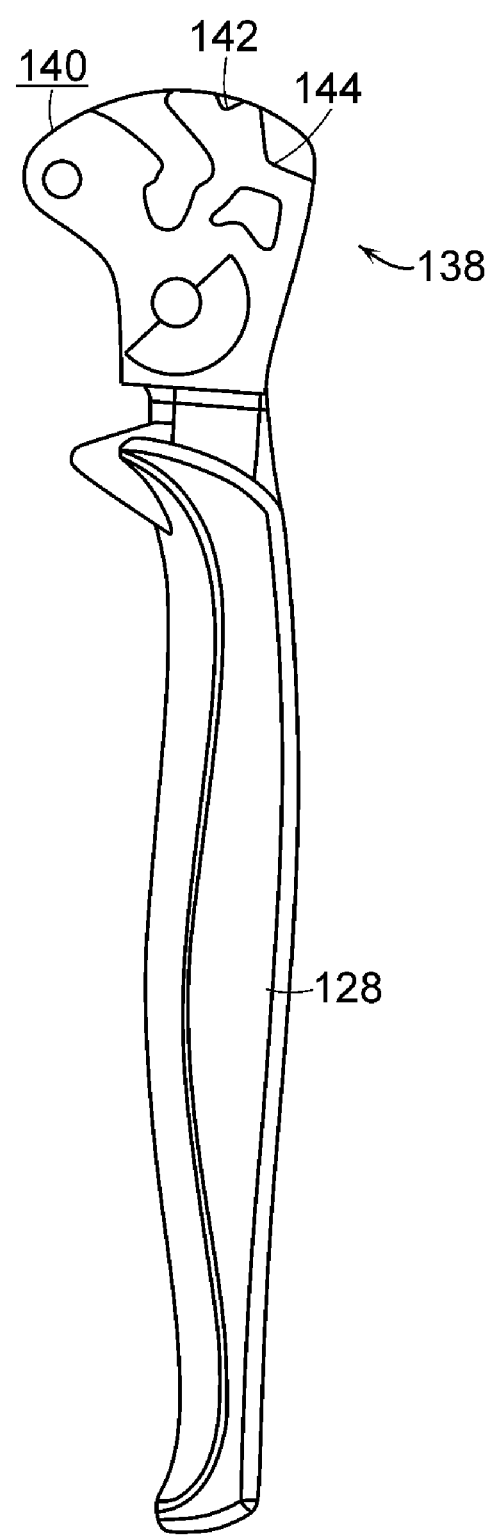
FIG. 14 is an elevational view of a closure trigger of an end effector closure system of the surgical instrument of FIG. 1.
Figure 15:
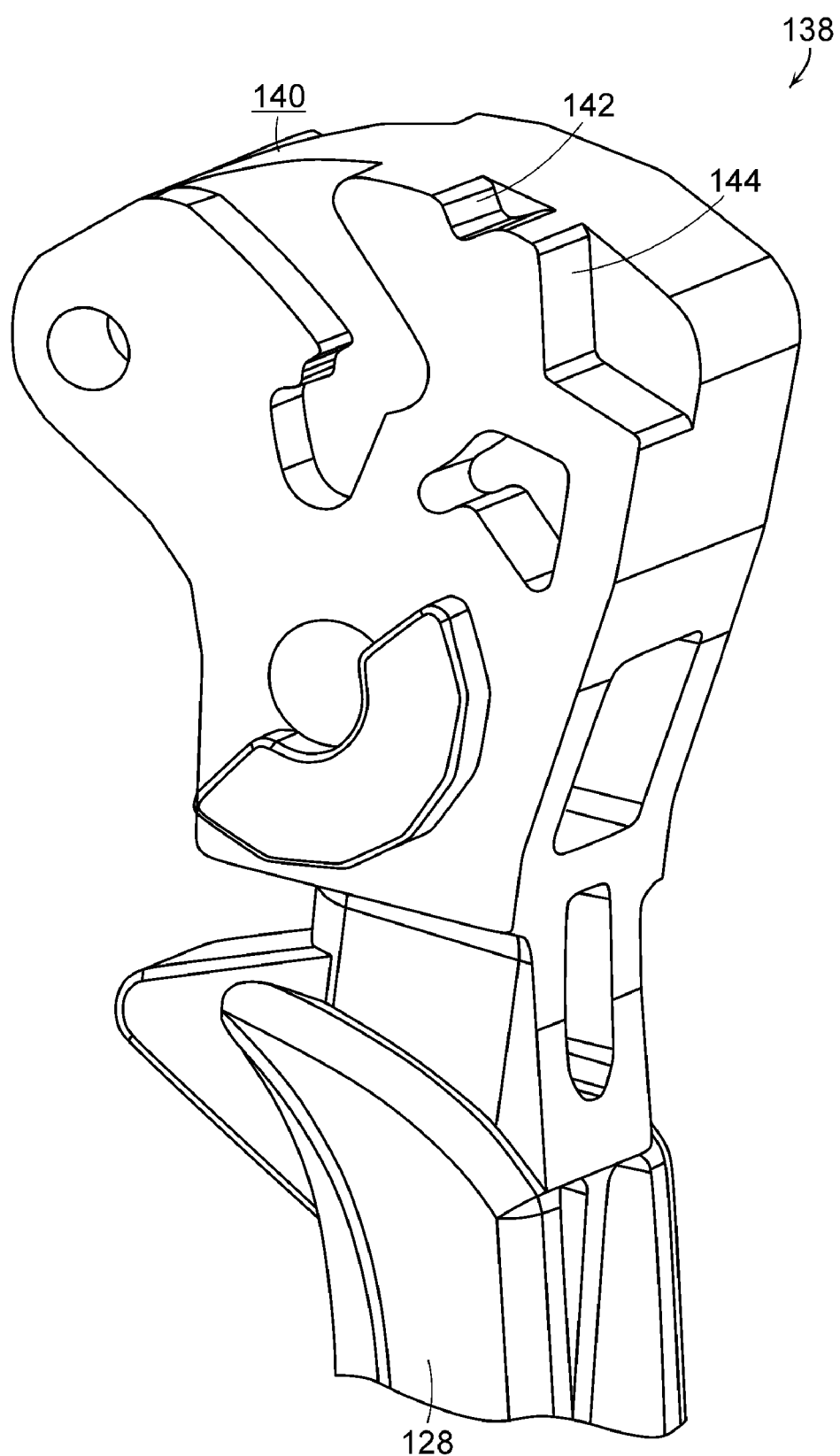
FIG. 15 is a partial perspective view of the closure trigger of FIG. 15.
Figure 16:
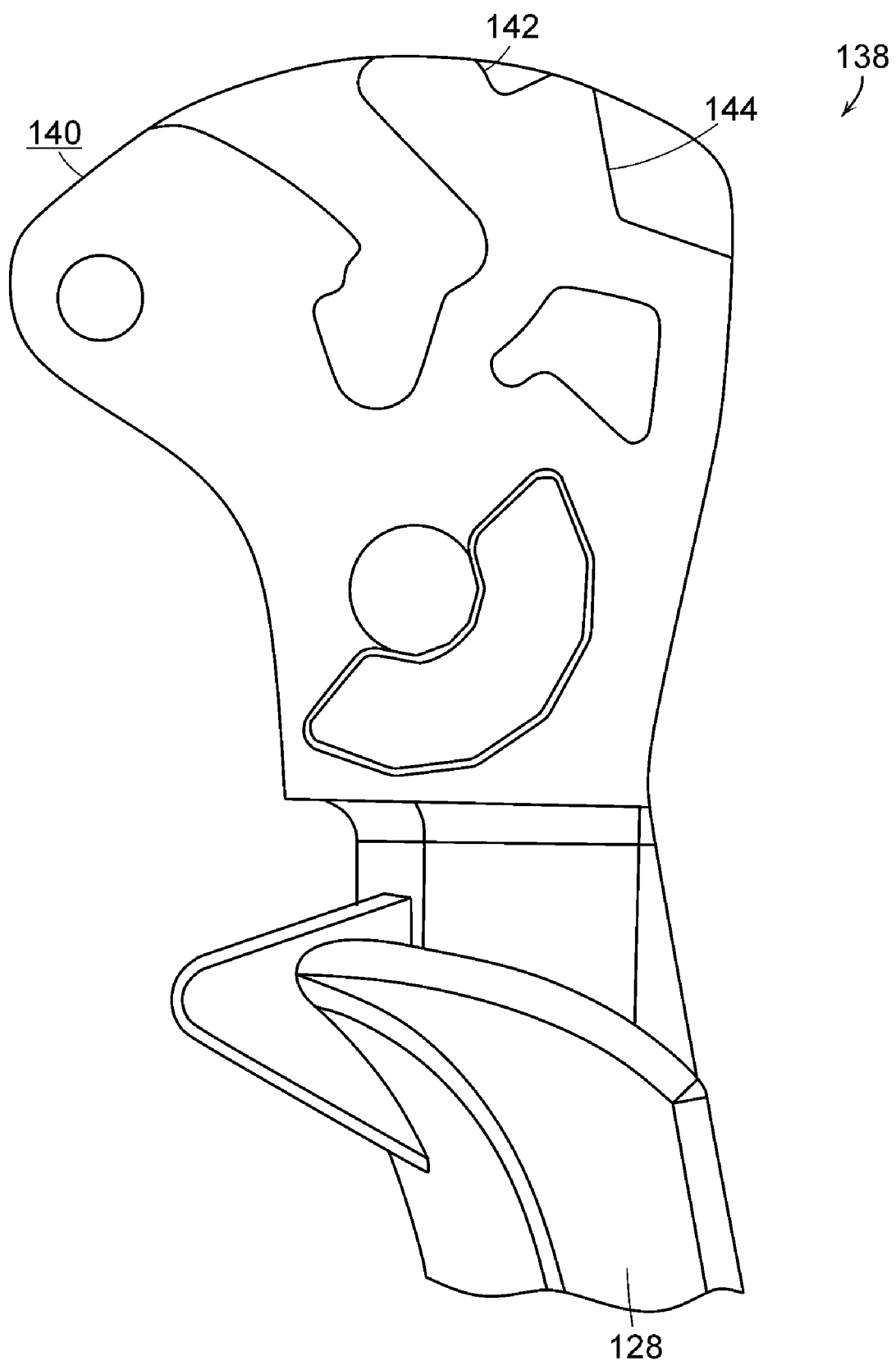
FIG. 16 is a partial elevational view of the closure trigger of FIG. 15.
Figure 17:
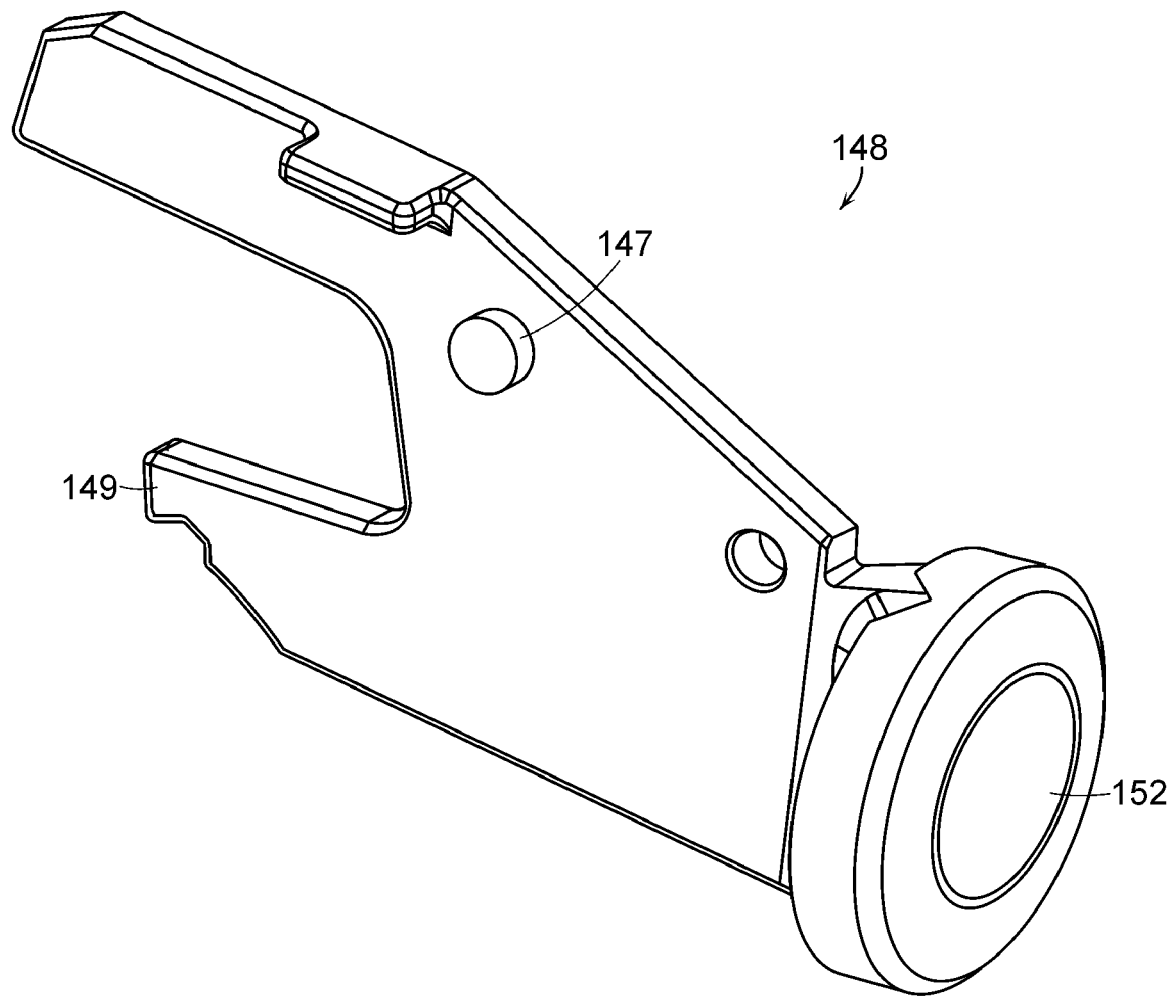
FIG. 17 is a perspective view of a trigger lock of the surgical instrument of FIG. 1.
Figure 18:
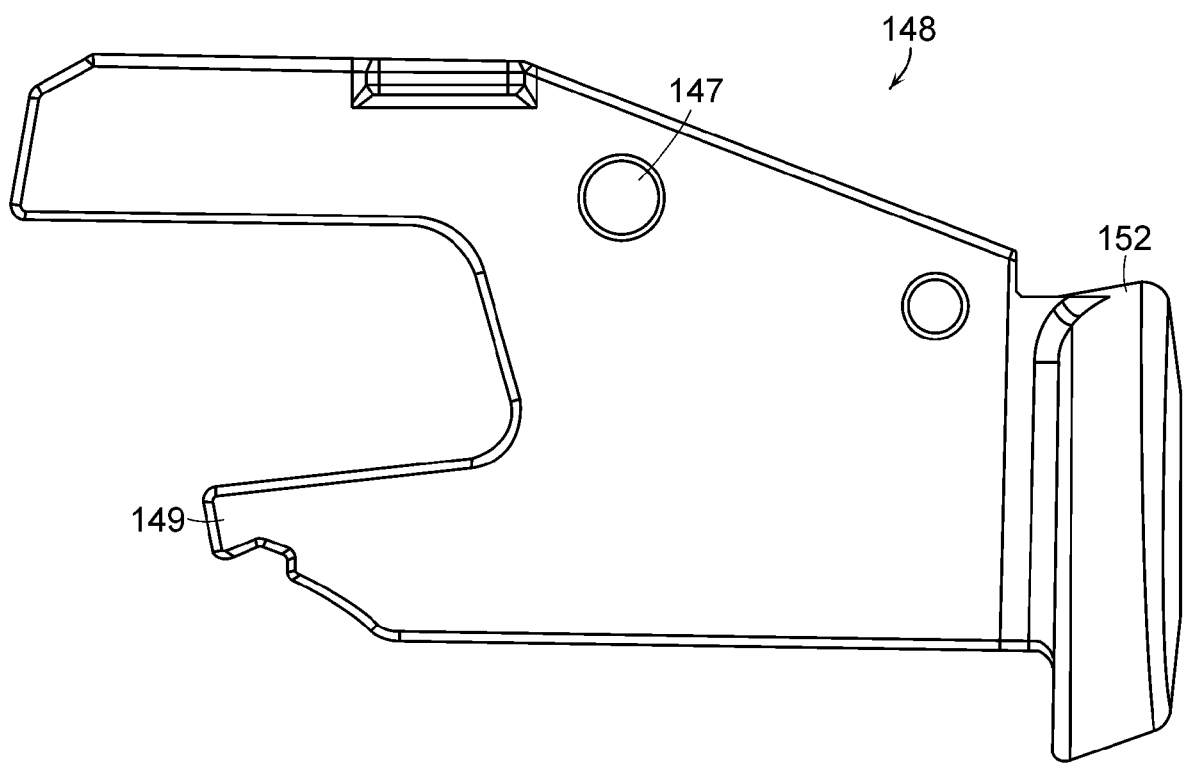
FIG. 18 is an elevational view of the trigger lock of FIG. 17.

In various embodiments, referring to FIGS. 10-13, the relative movement between actuator 122' and handle portion 102', as described above, can be limited in order to control the range through which lock member 120 can be displaced. More particularly, referring to FIGS. 10 and 11, the distal portion of actuator 122' can include projection 123 extending therefrom which can be received in cavity 125 where the displacement of actuator 122' can be limited by proximal wall 117 and distal wall 119 of cavity 125. In at least one embodiment, when trigger 128 is in its first position, as illustrated in FIGS. 10 and 11, actuator 122 can be moved from a distal position in which projection 123 can abut distal wall 119, as illustrated in FIG. 10, into a more proximal position in which projection 123 does not abut distal wall 119, as illustrated in FIG. 11. In this more distal position, as described above, lock member 120 can be disengaged from end effector 106 and end effector 106 can be rotated relative to shaft assembly 104. When trigger 128 is in its second position, referring to FIG. 12, driver 132 can limit the range of motion of actuator 122' such that projection 123 cannot be positioned against proximal wall 117. In at least one embodiment, however, actuator 122' can be moved proximally a sufficient distance to disengage lock member 120 from end effector 106. In these circumstances, a surgeon can reposition end effector 106 although anvil 112 may be partially closed onto the soft tissue, for example. When trigger 128 is in its third position, as illustrated in FIG. 13, driver 132 can force actuator 122' distally such that projection 132 abuts, or is positioned adjacent to, distal wall 119 and actuator 122' cannot be moved sufficiently to unlock articulation joint 114.

In various embodiments, a surgical instrument in accordance with the present invention can include a firing drive configured to advance a cutting member and/or staple driver within an end effector as described above. In at least one embodiment, referring to FIGS. 8, 9 and 19-25, the firing drive of surgical instrument 100 can include firing trigger 160, first firing link 162, second firing link 164, and firing member 166. In various embodiments, firing trigger 160 can be operably engaged with at least one of firing member 166 and firing links 162 and 164 in order to advance knife bar 168 within elongate shaft assembly 104. In at least one embodiment, knife bar 168 can be operably engaged with a cutting member (not illustrated) and a staple driver (not illustrated) in end effector 106 where the cutting member can be configured to incise tissue, for example, and the staple driver can be configured to deploy staples from staple cartridge 110. Cutting members and staple drivers are well disclosed in U.S. Pat. Nos. 6,905,057 and 7,044,352, which have been previously incorporated by reference into the present application, and, as a result, these devices are not described in greater detail herein. Other cutting members and staple drivers are disclosed in U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, which was filed on Sep. 29, 2006, and U.S. patent application Ser. No. 11/652,169, entitled SURGICAL STAPLING DEVICE WITH A CURVED CUTTING MEMBER, which was filed on Jan. 11, 2007, the entire disclosures of which are hereby incorporated by reference herein.

Figure 19:
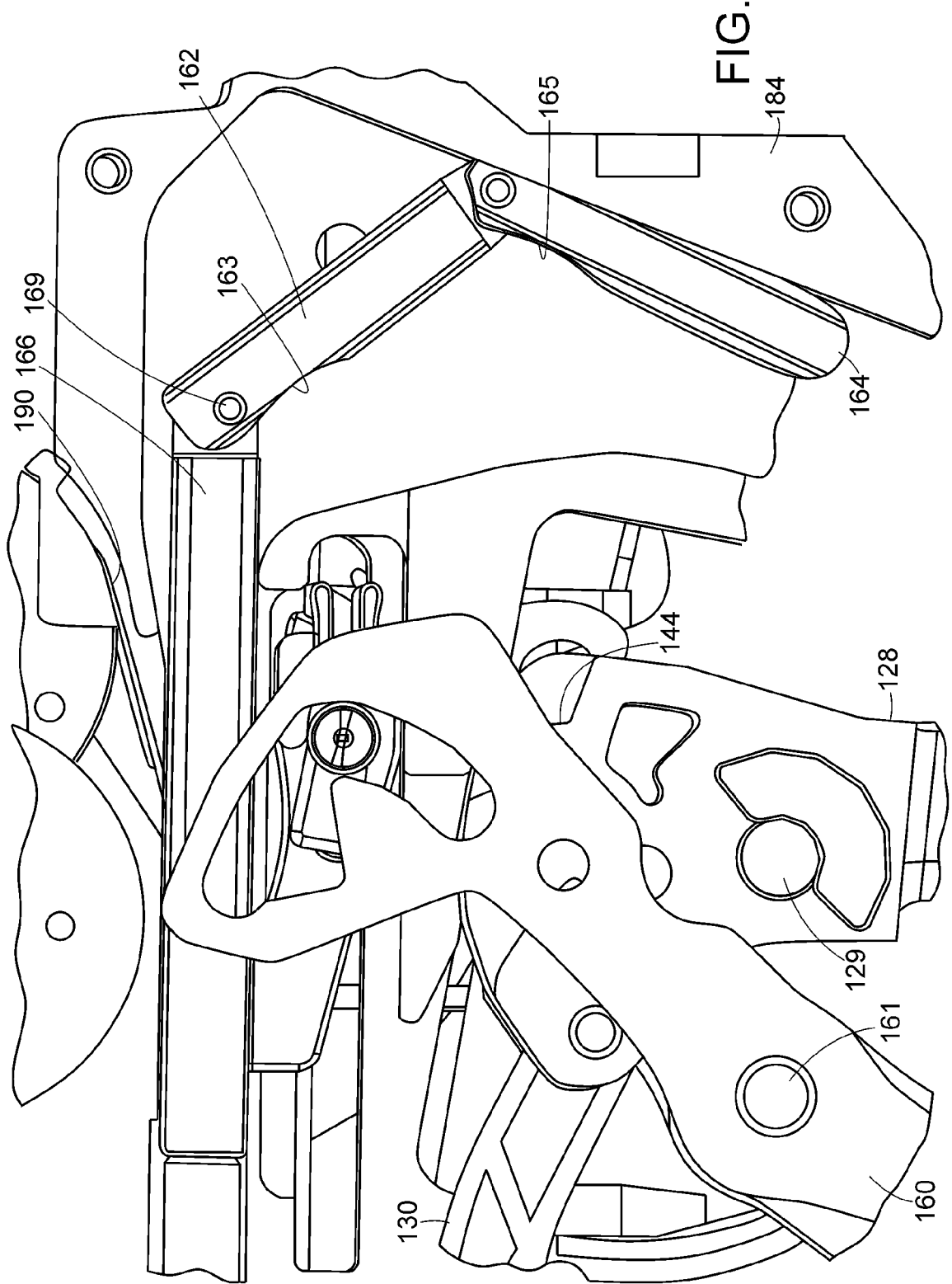
FIG. 19 is a detail view of a firing drive of the surgical instrument of FIG. 1 with some components of the surgical instrument removed.
Figure 20:
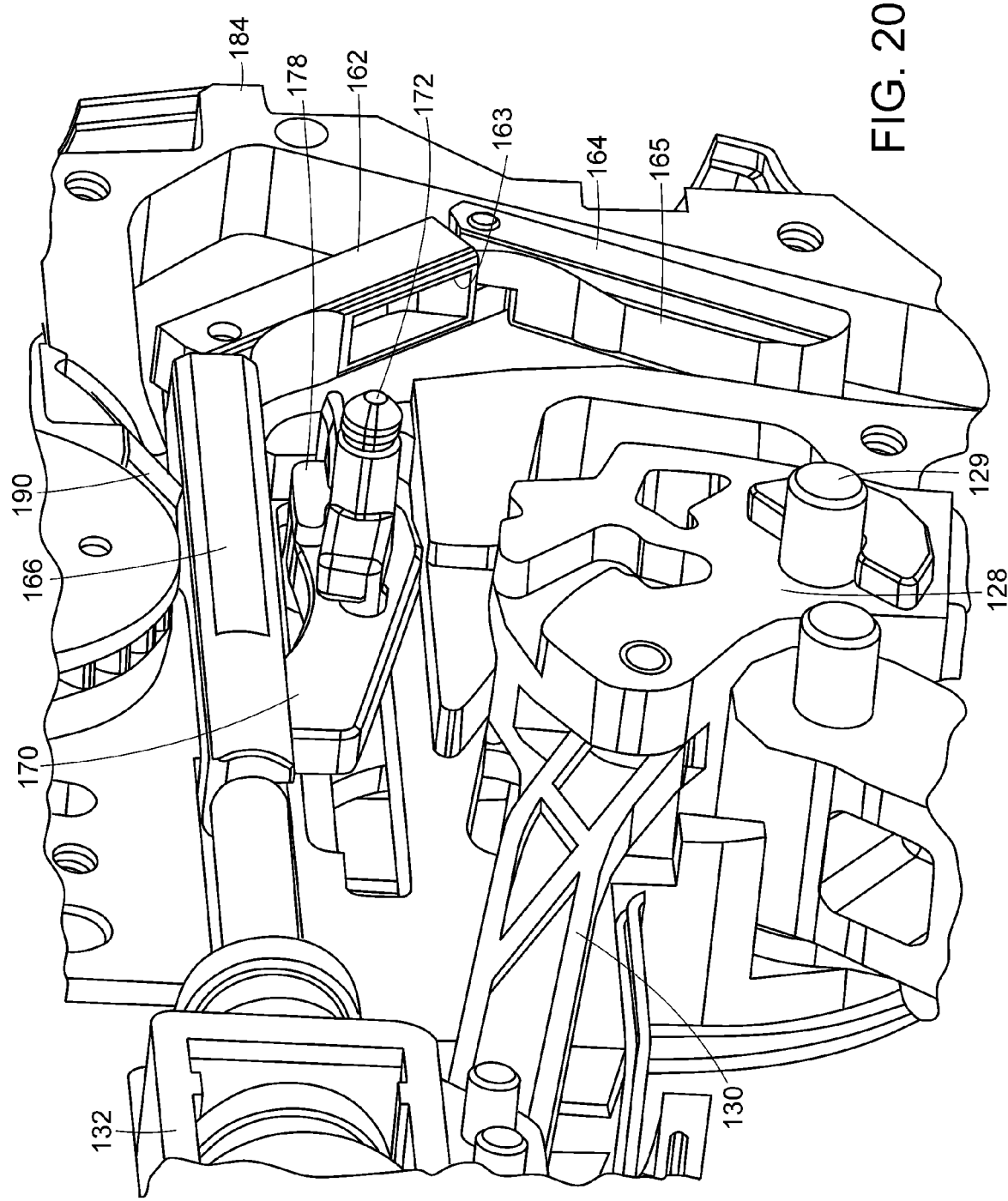
FIG. 20 is a perspective view of the firing drive of FIG. 19.
Figure 21:
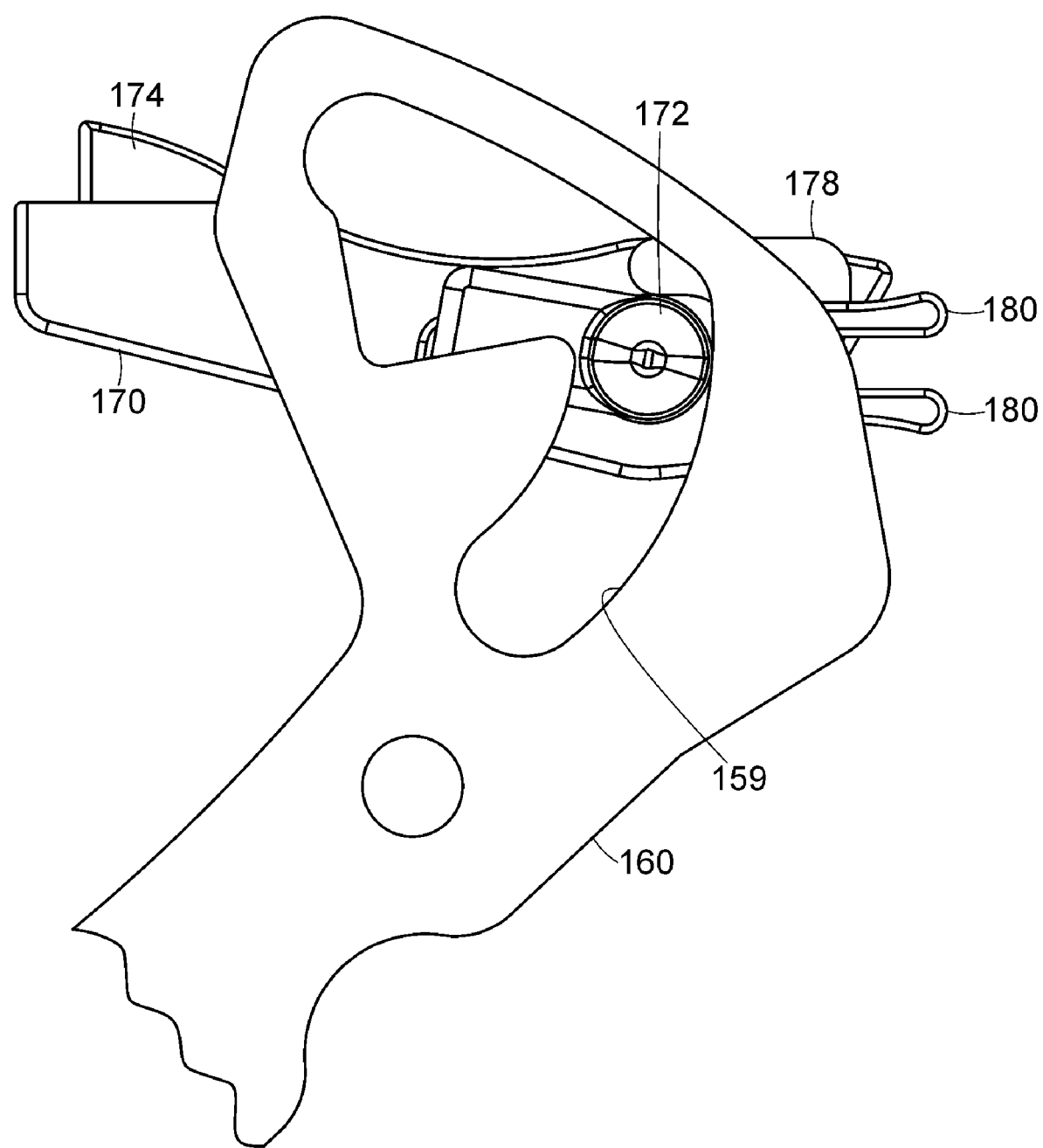
FIG. 21 is a partial detail view of a firing trigger, pawl, and tilter mechanism of the firing drive of FIG. 19.
Figure 22:
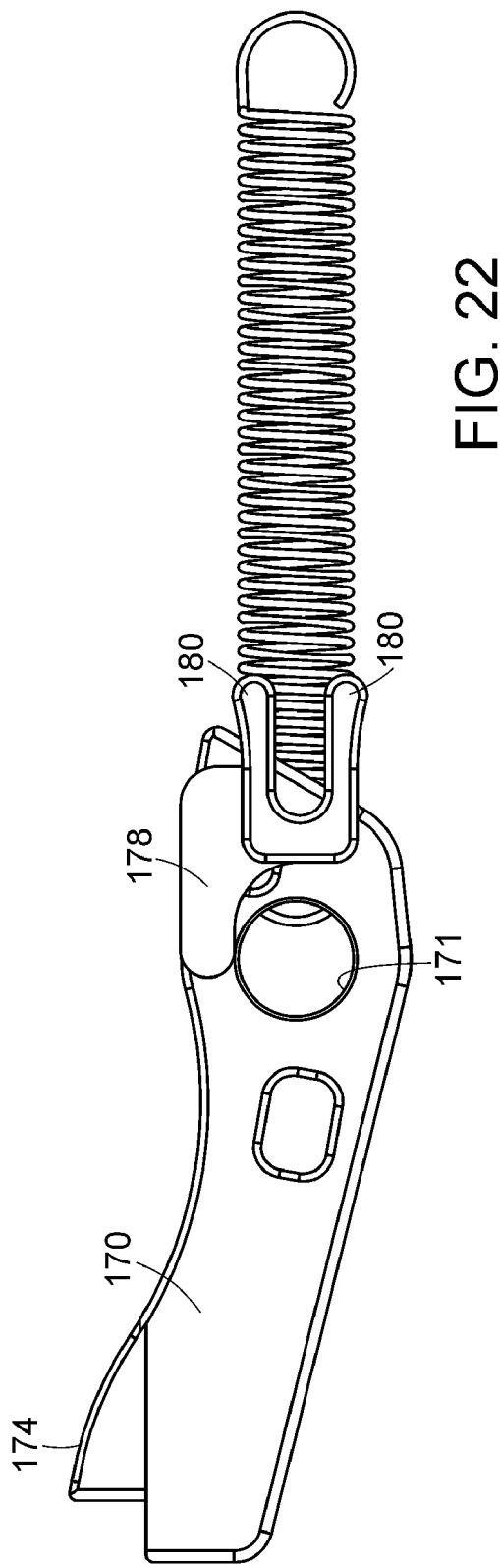
FIG. 22 is an elevational view of the pawl, tilter mechanism, and a pawl return spring of the firing drive of FIG. 19.
Figure 23:
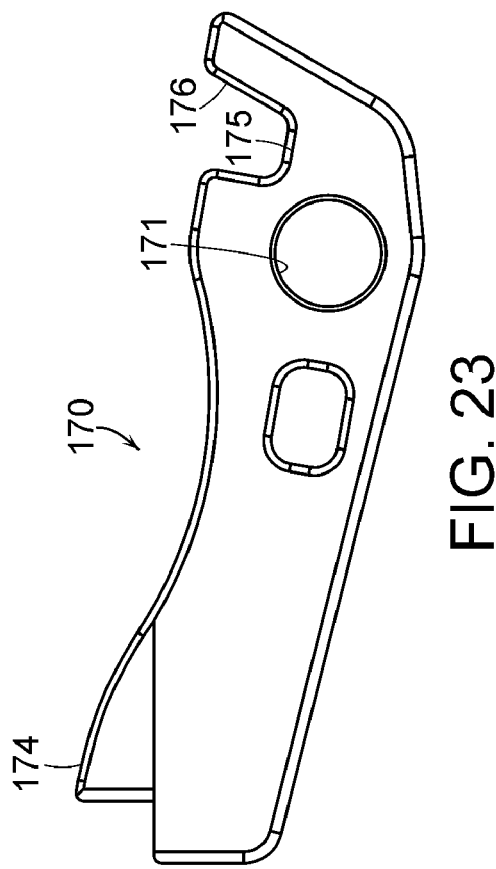
FIG. 23 is an elevational view of the pawl of FIG. 22.

In various embodiments, referring primarily to FIGS. 19 and 20, firing trigger 160 can be pivotably connected to surgical instrument housing 103 (FIGS. 8 and 9) by pin 161. In use, in at least one embodiment, firing trigger 160 can be pivoted about pin 161 in order to advance firing member 166 and firing links 162 and 164 distally. In various embodiments, firing trigger 160 can include slots 159, where slots 159 can be configured to receive firing pin 172. In various embodiments, when firing trigger 160 is actuated, or rotated, from its position illustrated in FIG. 2 to a position adjacent handle grip 127, the side walls of slots 159 can be configured to engage and advance firing pin 172 distally. In at least one embodiment, referring to FIG. 23, the firing drive can further include pawl 170, where pawl 170 can include aperture 171. In various embodiments, aperture 171 can be configured to receive at least a portion of firing pin 172 such that, when firing pin 172 is advanced distally by trigger 160, firing pin 172 can advance pawl 170 distally as well. In various embodiments, referring to FIG. 24, pawl 170 can include tooth 174 and firing member 166 can include recess 167, where recess 167 can be configured to receive tooth 174. In use, when pawl 170 is advanced distally by firing pin 172 and tooth 174 is engaged with a side wall of recess 167, pawl 170 can advance firing member 166 distally as well. In various embodiments, pawl 170 can be advanced distally by firing pin 172 along a substantially linear path. In such embodiments, slots 159 can include arcuate profiles which can, in cooperation with firing pin 172, convert the rotational motion of firing trigger 160 into translational motion of pawl 170. In at least one embodiment, the force applied to pawl 170 can be substantially, if not entirely, directed in the distal direction. In such embodiments, as a result, the possibility of pawl 170 becoming bound or stuck against stapler frame 184 can be reduced.

In various embodiments, pawl 170 can be pivoted between a first position in which pawl 170 is operably disengaged from firing member 166 and a second position, referring to FIGS. 19 and 20, in which pawl 170 is operably engaged with firing member 166. Referring primarily to FIGS. 21-25, the firing drive can further include tilter mechanism 178 which can be configured to pivot pawl 170 between its first and second positions. In use, when firing trigger 160 is actuated, pawl 170 can be moved, at least initially, relative to tilter mechanism 178 such that at least a portion of pawl 170 can abut tilter mechanism 178 and pivot pawl 170 upwardly and into operative engagement with firing member 166. In at least one embodiment, pawl 170 can include, referring primarily to FIG. 23, groove 175 which can be configured to receive projection 179 (FIG. 25) extending from the center portion of tilter mechanism 178. In at least one embodiment, as pawl 170 is advanced distally, proximal wall 176 of groove 175 can contact a cam surface on projection 179 and, owing to the force applied to pawl 170 by pivot pin 172, pawl 170 can be pivoted, or rotated, upwardly such that tooth 174 can be positioned in recess 167 of firing member 166 as described above. After pawl 170 has been pivoted, pawl 170 can drag tilter mechanism 178 distally as pawl 170 is advanced toward end effector 106. More particularly, in at least one embodiment, tilter mechanism 178 can include deformable members 180 which can be received within slots 182 in stapler frame 184 such that the interaction between deformable members 180 and stapler frame 184 at least partially inhibits the movement of tilter mechanism 178 relative to stapler frame 184. Stated another way, owing to static friction forces between deformable members 180 and the side walls of slots 182, a force sufficient to overcome these friction forces must be applied to tilter mechanism 178 before tilter mechanism 178 can be 'dragged' relative to stapler frame 184.

Figure 24:
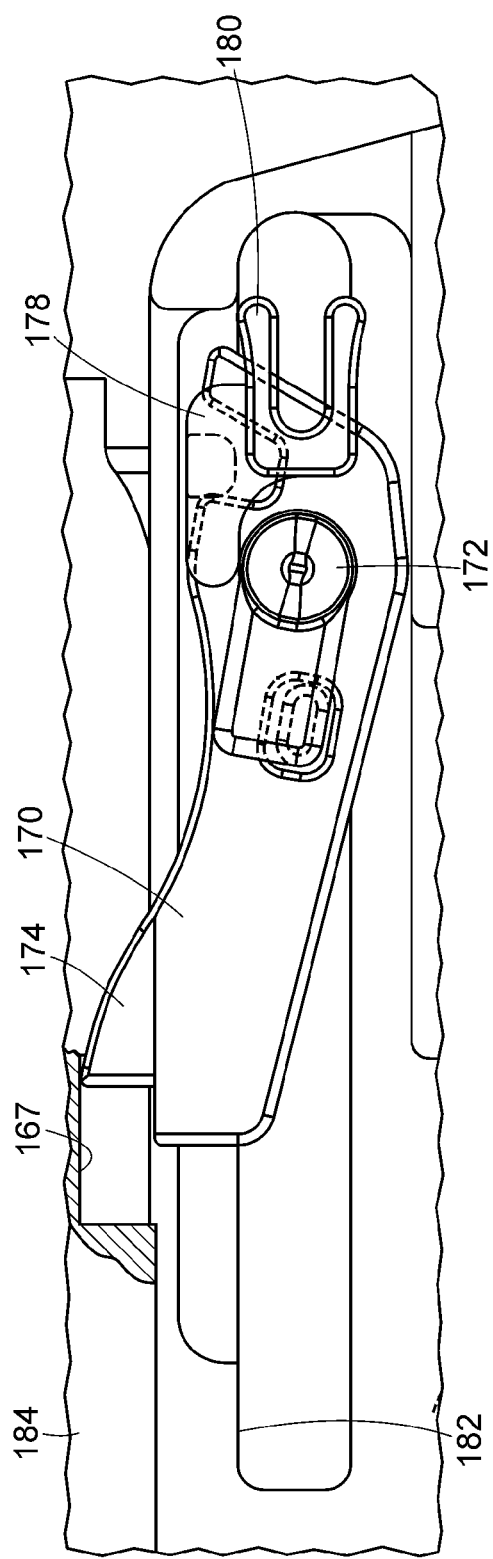
FIG. 24 is a detail view of the firing drive of FIG. 19 illustrating the pawl pivoted into a position to engage a firing link of the firing drive.
Figure 25:
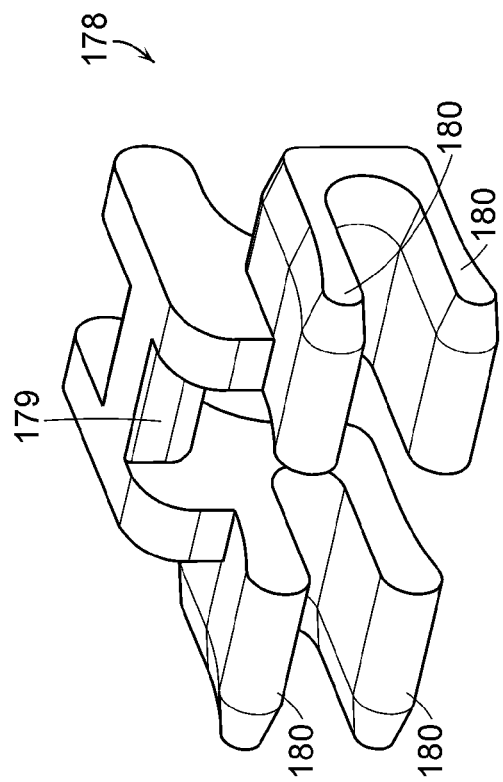
FIG. 25 is a perspective view of the tilter mechanism of FIG. 22.
Figure 26:
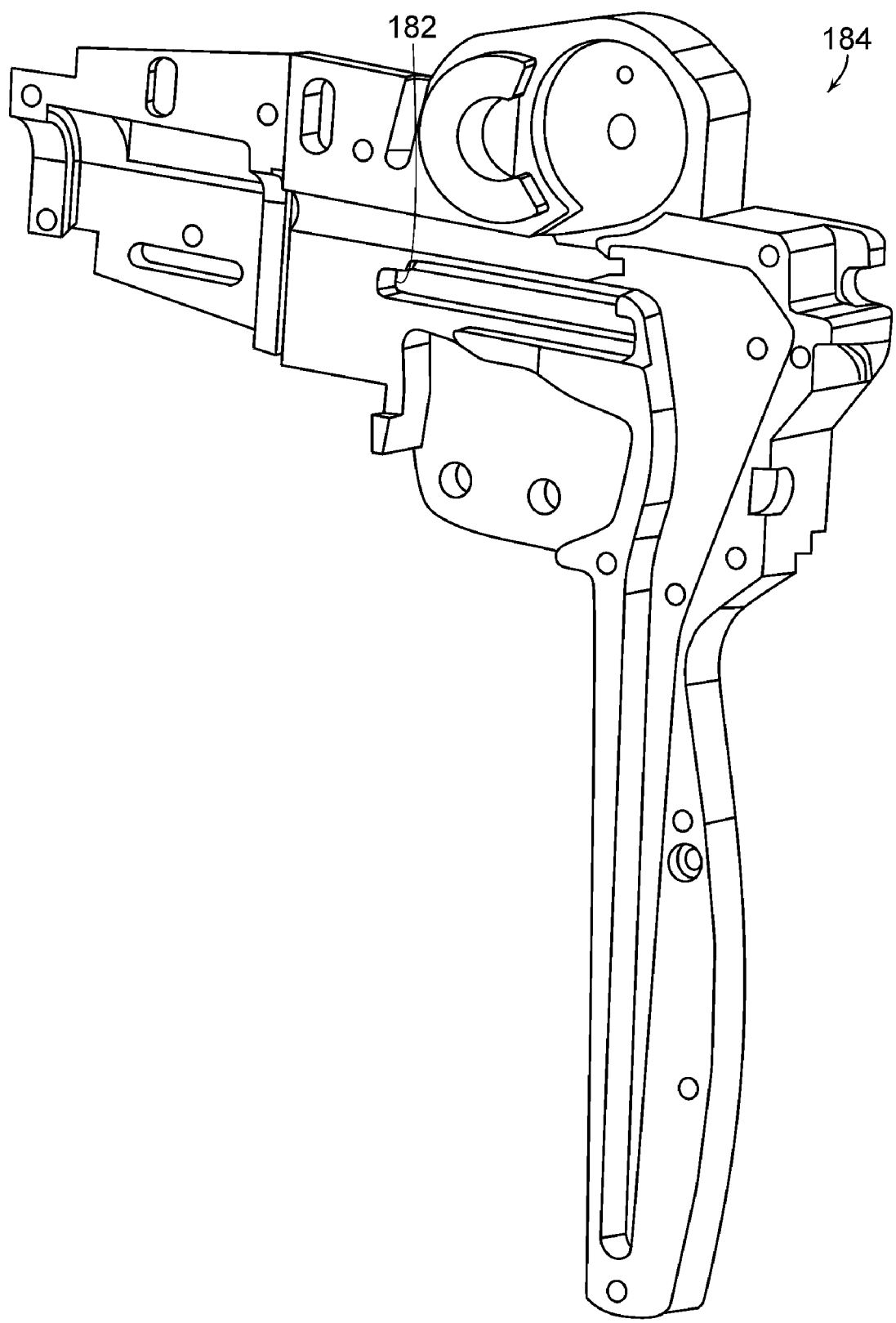
FIG. 26 is a perspective view of a frame of the surgical instrument of FIG. 1.

After firing trigger 160 has been actuated and firing member 166 has been advanced, trigger 160 can be released and returned to its unactuated position illustrated in FIG. 2 and pawl 170 can be disengaged from firing member 166 and retracted to its starting position illustrated in FIG. 19. More particularly, in at least one embodiment, surgical instrument 100 can further include a trigger spring (not illustrated) operably engaged with trigger 160 and housing 103, for example, where the trigger spring can be configured to rotate trigger 160 about pin 161 and drive firing pin 172 proximally after pawl 170 has been disengaged from firing member 166. In various embodiments, pawl 170 can be disengaged from firing member 166 when it is pivoted from its second position, as illustrated in FIG. 24, into its first position, as described above, by tilter mechanism 178. In such embodiments, pawl 170 can be moved, at least initially, relative to tilter mechanism 178 such that distal wall 177 of groove 175 can contact a second cam surface on projection 179 and can, owing to a force applied to firing pin 172 by trigger 160 or return spring 186, rotate pawl 170 downwardly such that tooth 174 of pawl 170 can be disengaged from recess 167 in firing member 166. Thereafter, trigger 160 and/or return spring 186 can pull, or retract, pawl 170 relative to firing member 166. In various embodiments, similar to the above, pawl 170 can be configured to drag tilter mechanism 178 proximally within slot 182. As a result of the above, pawl 170 does not need to be biased into its first or second positions. In various circumstances, pawl 170 can be rotated freely between its first and second positions without having to overcome a force applied thereto by a biasing spring. In effect, in various embodiments, the force to move pawl 170 between its first and second positions need only overcome the gravitational weight of pawl 170 and any frictional forces between pawl 170 and the surrounding components of the surgical instrument.

Once pawl 170 has been returned to its original position, in at least one embodiment, tooth 174 of pawl 170 may no longer be aligned with recess 167 in firing member 166. On the contrary, referring generally to FIGS. 19 and 20, tooth 174 of pawl 170 can be aligned with recess 163 in first firing link 162. More particularly, first firing link 162 can be pivotably connected to firing member 166 such that, when firing member 166 is advanced distally, as described above, firing member 166 can pull first firing link 162 into the position that firing member 166 previously occupied. As a result, upon a second actuation firing trigger 160, pawl 170 can be pivoted from its first position into its second position such that tooth 174 is operably engaged with recess 163 and pawl 170 can advance firing link 162 distally. In at least one embodiment, firing link 162 can push firing member 166 and knife bar 168 distally and, correspondingly, advance the cutting member and the staple driver distally within end effector 106. Thereafter, pawl 170 can once again be pivoted from its second position to its first position and can be retracted relative to first firing link 162. Once pawl 170 is returned to its original position for the second time, tooth 174 of pawl 170 may no longer be aligned with recess 163 of first firing link 162. On the contrary, similar to the above, tooth 174 can be aligned with recess 165 in second firing link 164 and the process described above can be repeated.

Although not illustrated, a surgical instrument in accordance with the present invention can include more than two, or less than two, firing links in order to advance the cutting member and staple driver to their desired positions within end effector 106. In various embodiments, although not illustrated, firing member 166 can include more than one recess 167 such that pawl 170 can directly advance firing member 166 toward end effector 106 more than once. In at least one such embodiment, pawl 170 can be retracted after advancing firing member 166 distally, as described above, such that, when pawl 170 is once again tilted upwardly, pawl 170 can engage another recess 167 in firing member 166 and advance firing member 166 toward end effector 106 once again. As a result, in at least one embodiment, firing links 162 and 164 may not be required.

Figure 27:
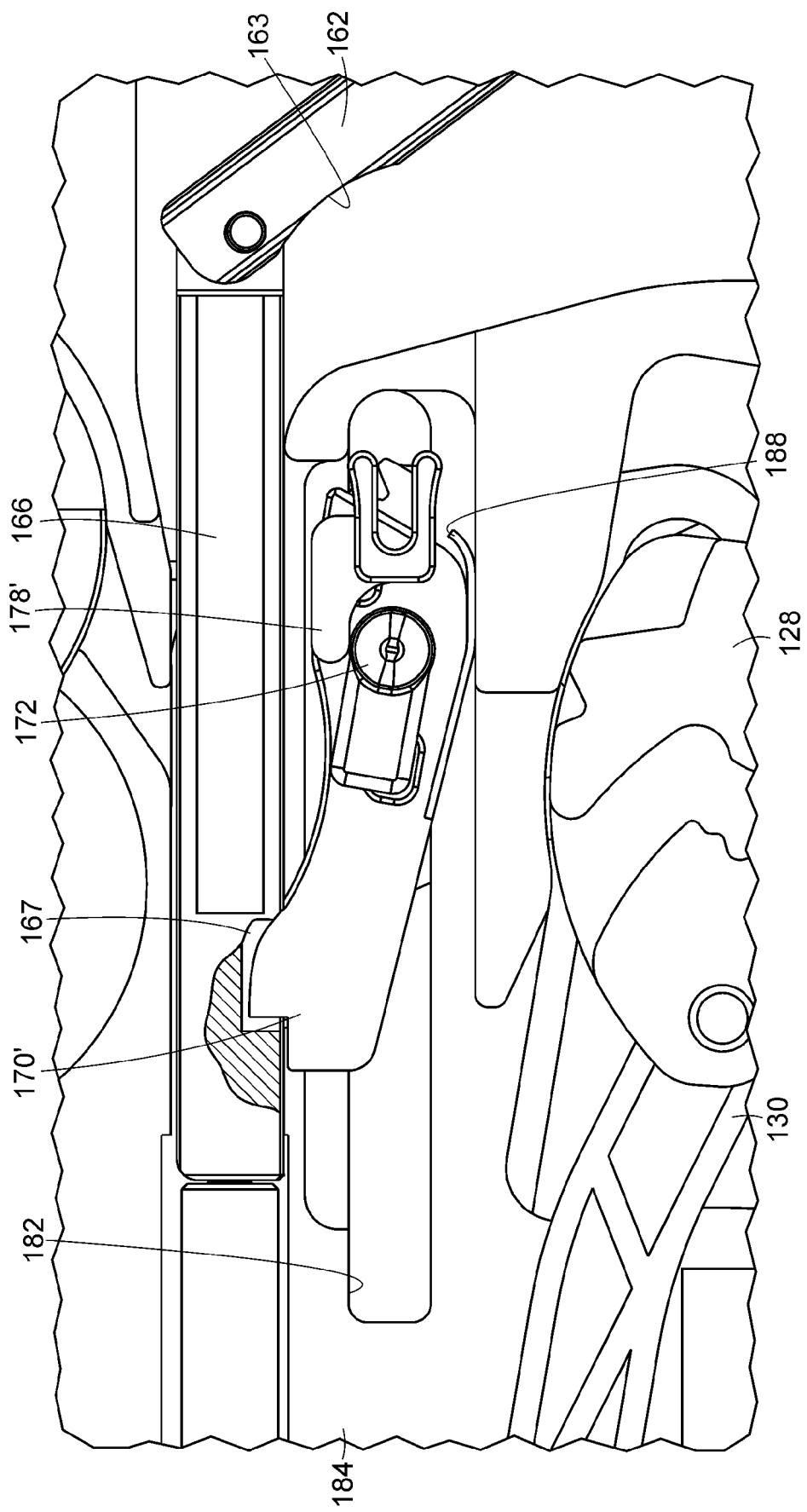
FIG. 27 is a detail view of a firing drive of a surgical instrument in accordance with an alternative embodiment of the present invention with some components of the surgical instrument removed.
Figure 28:
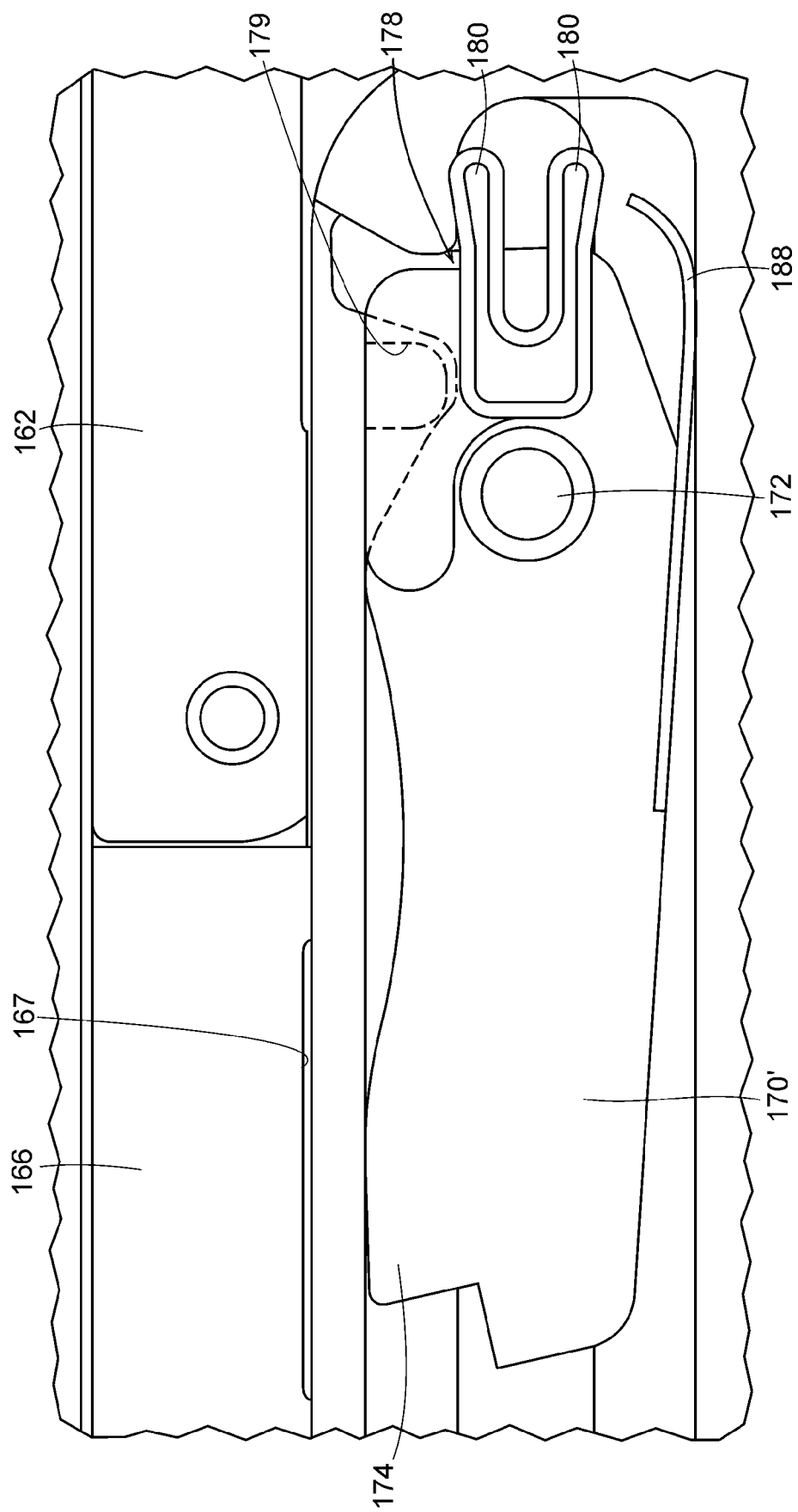
FIG. 28 is a detail view of the firing drive of FIG. 27 illustrating a pawl of the firing drive disengaged from a firing link.

In various embodiments, a surgical instrument can include one or more spring members configured to move pawl 170 into at least one of its first and second positions. In at least one embodiment, referring to FIGS. 27 and 28, the firing drive can include pawl 170', firing pin 172, and tilter mechanism 178' where, similar to the above, tilter mechanism 178' can be configured to pivot pawl 170' upwardly when pawl 170' is advanced distally. The firing drive can further include pivot spring 188 which can be operably connected to pawl 170' such that, when pawl 170' is pivoted upwardly into its second position as illustrated in FIG. 27, pawl 170' can flex, or resiliently bend, pivot spring 188. After pawl 170' has been advanced, pawl 170' can be pivoted downwardly into its first position by pivot spring 188 as illustrated in FIG. 28. More particularly, owing to potential energy stored in pivot spring 188 when it is flexed, spring 188 can move pawl 170' downwardly once pawl 170' is no longer held in its second position by tilter mechanism 178' and firing pin 172. Thereafter, as described above, pawl 170' can be retracted relative to firing member 166 and/or firing links 162 and 164. In various embodiments, tilter mechanism 178' may not include a second cam surface for pivoting pawl 170 into its first position. In such embodiments, pawl 170' can be retracted by a force applied to firing pin 172 as described above. In various alternative embodiments, although not illustrated, tilter mechanism 178' and pawl 170' can also include co-operating features for pivoting pawl 170' downwardly into its first position.

In various embodiments, referring to FIGS. 19 and 20, surgical instrument 100 can further include band 190 which can be configured to move firing member 166 and firing links 162 and 164 relative to end effector 106. In at least one embodiment, a first. end of band 190 can be connected to firing member 166, for example, such that, when firing member 166 is advanced distally, band 190 can be pulled distally as well. In various alternative embodiments, band 190 can be connected to first firing link 162 and/or second firing link 164. In at least one embodiment, band 190 can be positioned around at least a portion of reel, or spool, 192 such that when band 190 is pulled by firing member 166, band 190 can be deployed, or unwound, from reel 192. In at least one embodiment, a second end of band 190 can be connected to reel 192 such that band 190 cannot be readily disengaged from reel 192 under the normal operating conditions of surgical instrument 100. In either event, when band 190 is pulled by firing member 166, reel 192 can be rotated in one of a clockwise or counter-clockwise direction, depending on the manner in which band 190 is positioned around reel 192. In order to retract firing member 166, reel 192 can be rotated in an opposite direction to move firing member 166, and firing links 162 and 164, proximally and wind band 190 around reel 192.

In various embodiments, band 190 can be wound around reel 192 such that band 190 is wrapped around a substantially cylindrical surface on reel 192. In at least one embodiment, the distance between an axis of rotation of reel 192 and the cylindrical surface can be substantially equidistant around the perimeter of reel 192. In these embodiments, the mechanical advantage of reel 192 can remain substantially constant as band 190 is pulled proximally as described above and the capacity for reel 192 to apply a pulling force to band 190 can remain substantially the same. In alternative embodiments, however, reel 192 can be configured to provide a variable mechanical advantage. In at least one embodiment, reel 192 can include a non-cylindrical surface on which band 190 can be wrapped such that the distance between the axis of rotation of reel 192 and the non-cylindrical surface is not equidistant around the perimeter of reel 192. In these embodiments, as a result, the capacity for reel 192 to apply a pulling force to band 190 can change as band 190 is wound around reel 192. In at least one embodiment, reel 192 can act as a cam and can include a shape which can be optimized to provide additional force to band 190 when it is initially retracted, i.e., when the force to retract the cutting member, for example, can be at its highest.

Figure 29:
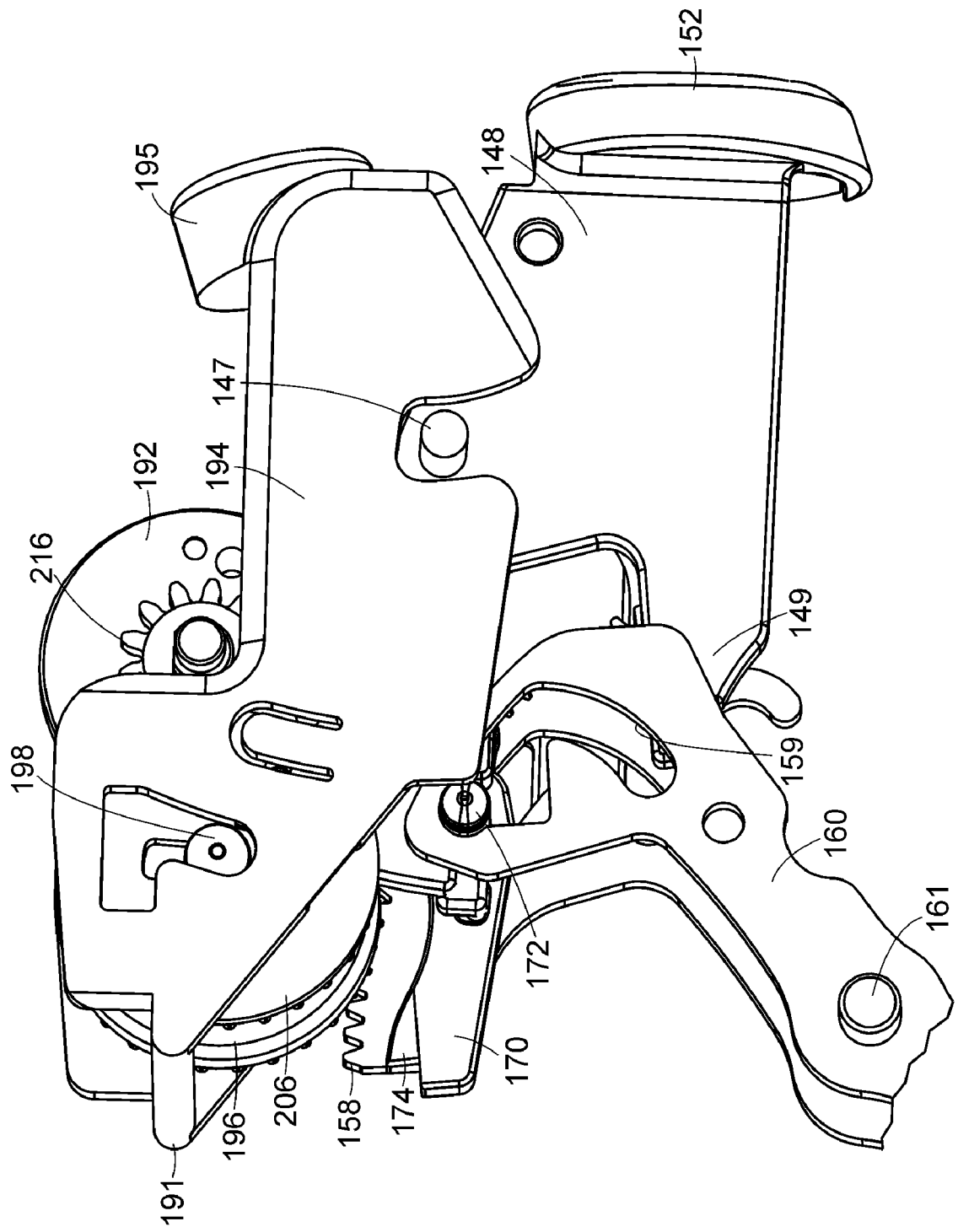
FIG. 29 is a perspective view of a return mechanism of the surgical instrument of Claim 1 illustrating the firing trigger in an unactuated position with some components of the surgical instrument removed.

In various embodiments, referring to FIGS. 29-42, firing trigger 160 can be selectively engaged with a return mechanism of surgical instrument 100. In at least one embodiment, when firing trigger 160 is operably engaged with firing member 166 via pawl 170, as described above, an actuation of firing trigger 160 can advance firing member 166 distally and, when firing trigger 160 is operably engaged with firing member 166 via band 190, an actuation of firing trigger 160 can retract firing member 166 proximally. In various embodiments, the return mechanism can be manually actuated to disengage firing trigger 160 from firing member 166 and to operably engage firing trigger 160 with reel 192. In at least one embodiment, the return mechanism can include return carriage 194 which can be pivotably mounted in surgical instrument housing 103 such that return carriage 194 can be pivoted between a first, or unactuated, position as illustrated in FIG. 29 and a second, or actuated, position as illustrated in FIG. 32. In at least one such embodiment, return carriage 194 can include push button portion 195 which, when a force is applied thereto, can be configured to move return carriage 194 from its unactuated position to its actuated position.

Figure 30:
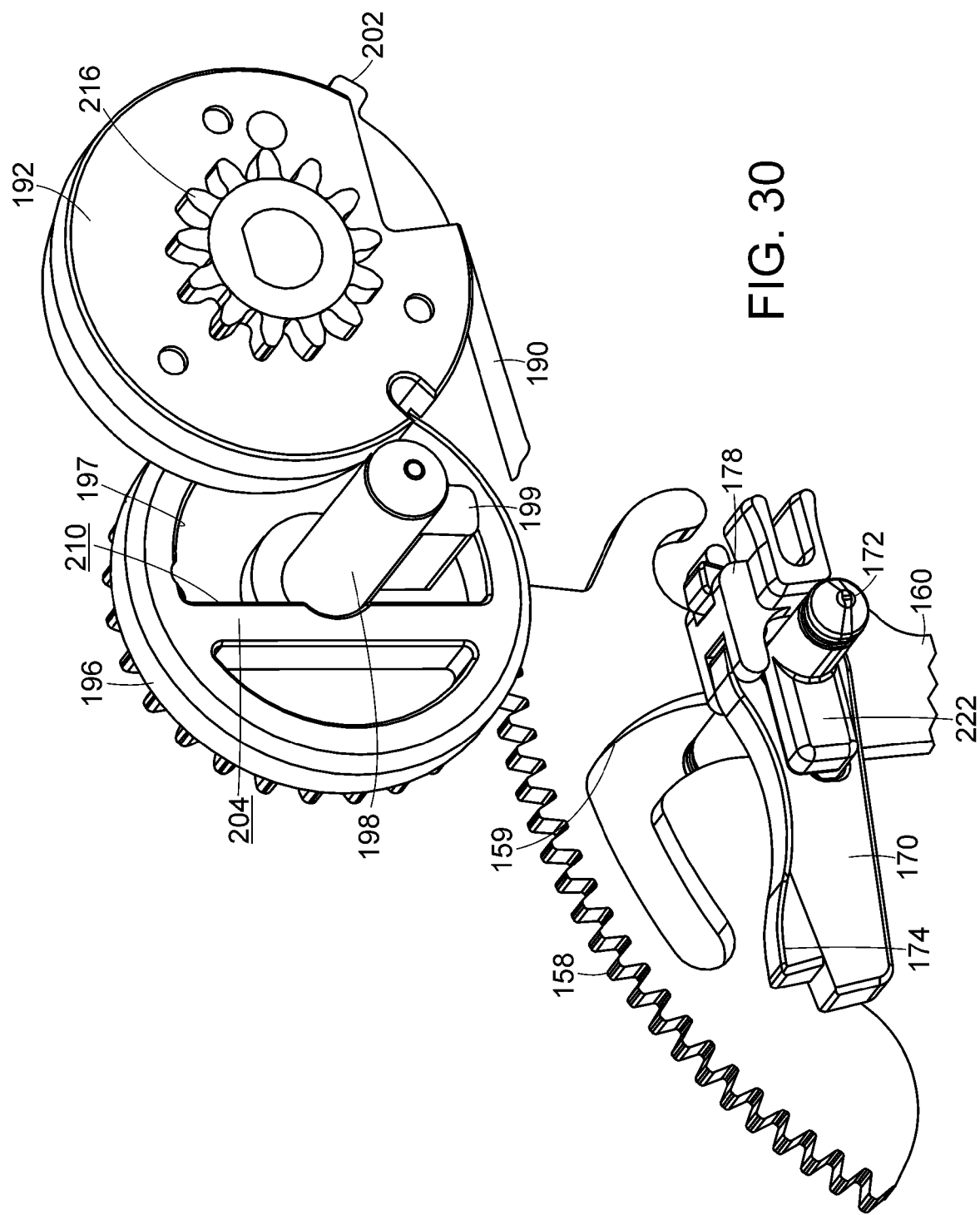
FIG. 30 is a partial perspective view of the return mechanism of FIG. 29 illustrating the firing trigger in an actuated position with some components of the return mechanism removed.
Figure 31:
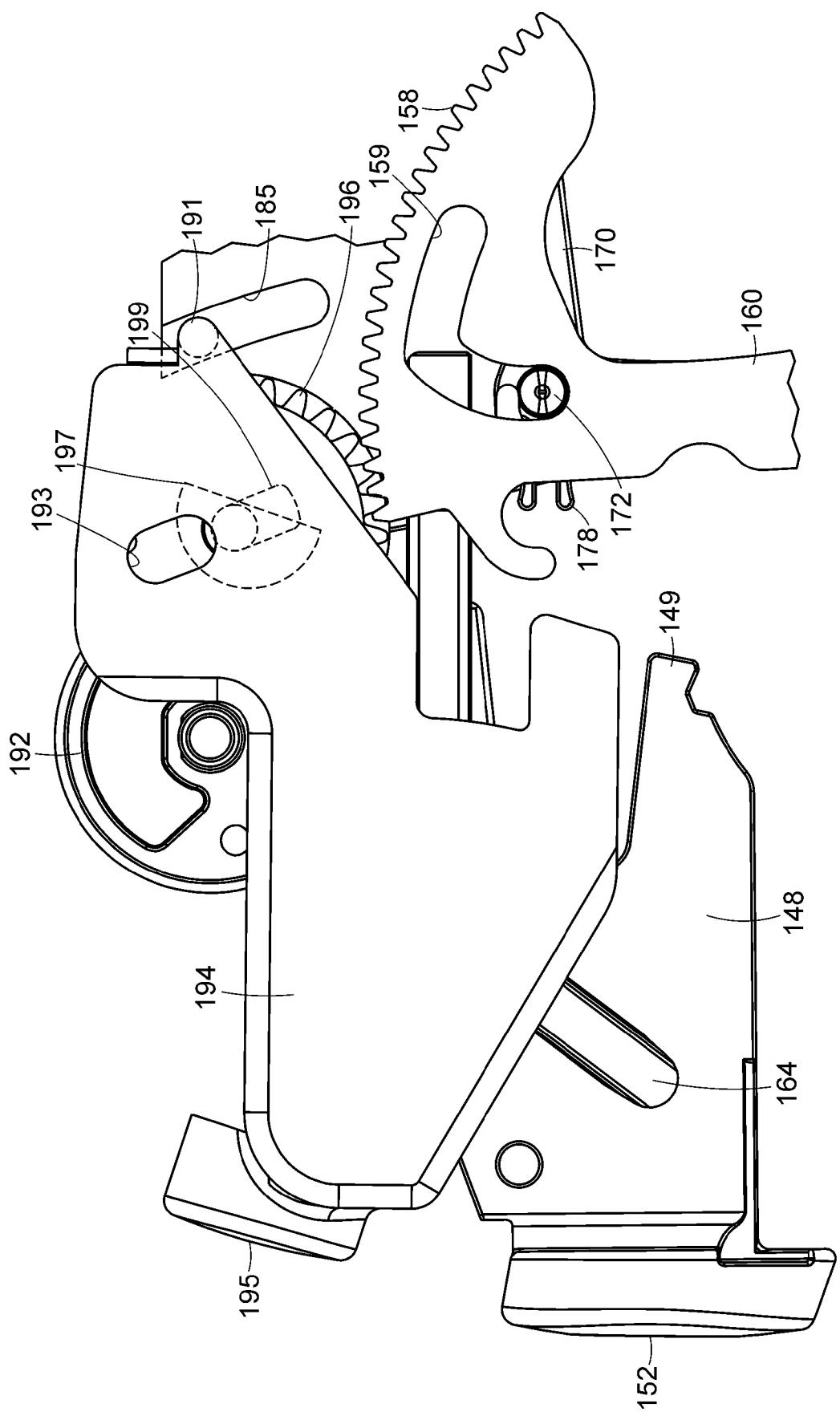
FIG. 31 is an elevational view of the return mechanism of FIG. 29 arranged in the configuration illustrated in FIG. 30.
Figure 32:
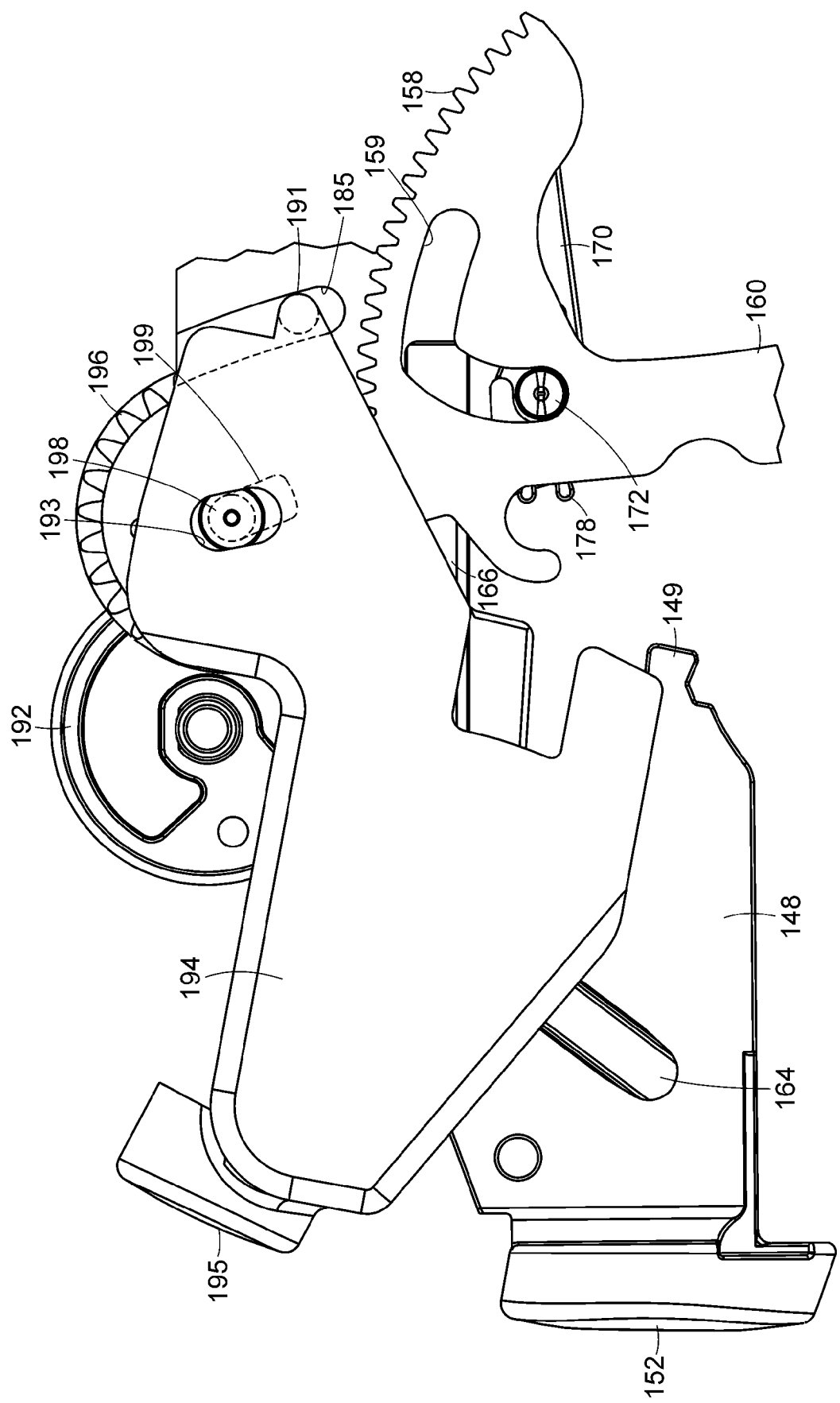
FIG. 32 is an elevational view of the return mechanism of FIG. 29 illustrating a return carriage of the return mechanism in an actuated position.
Figure 33:
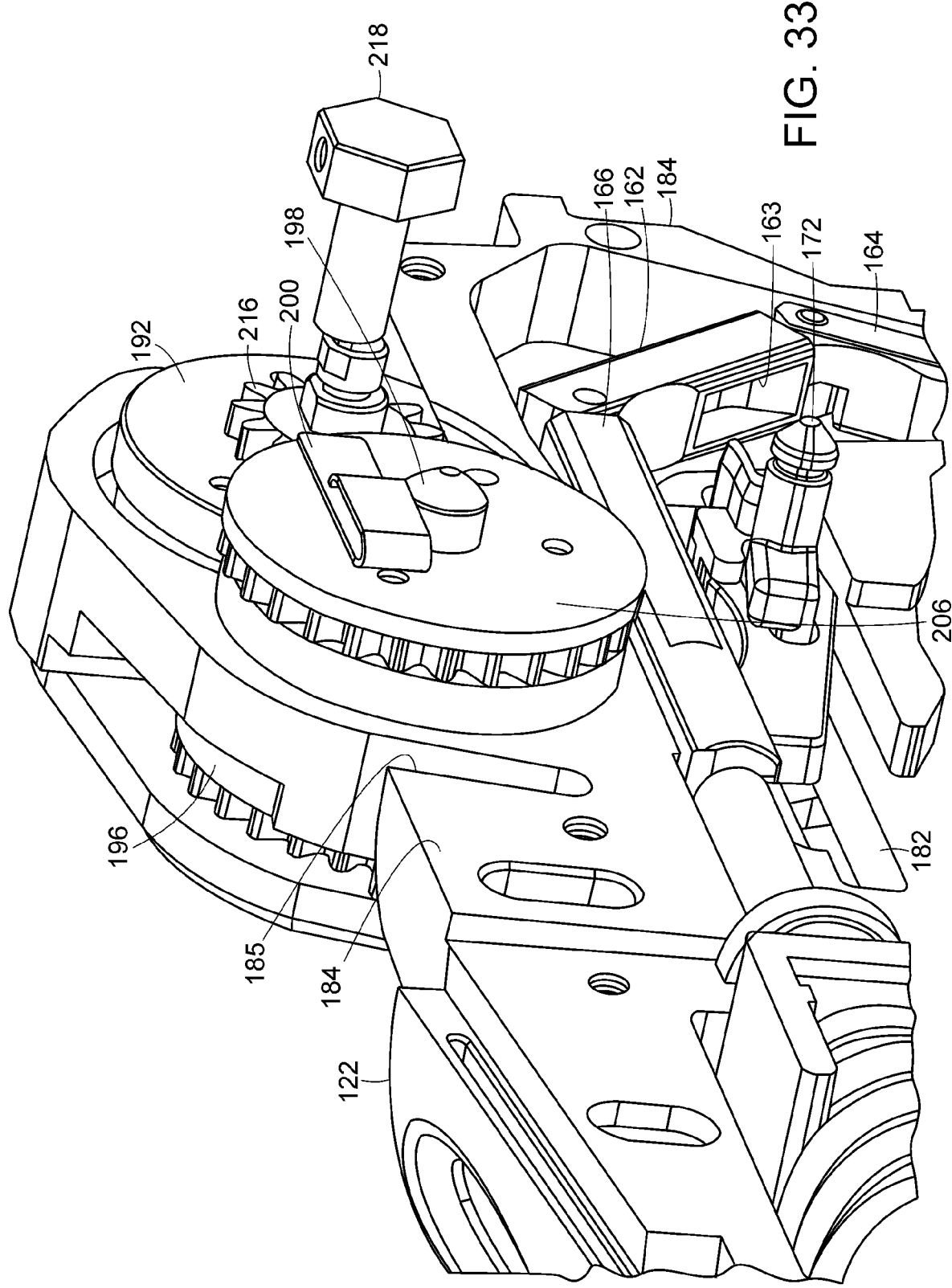
FIG. 33 is a partial perspective view of the return mechanism of FIG. 29 with some components of the return mechanism removed.
Figure 34:
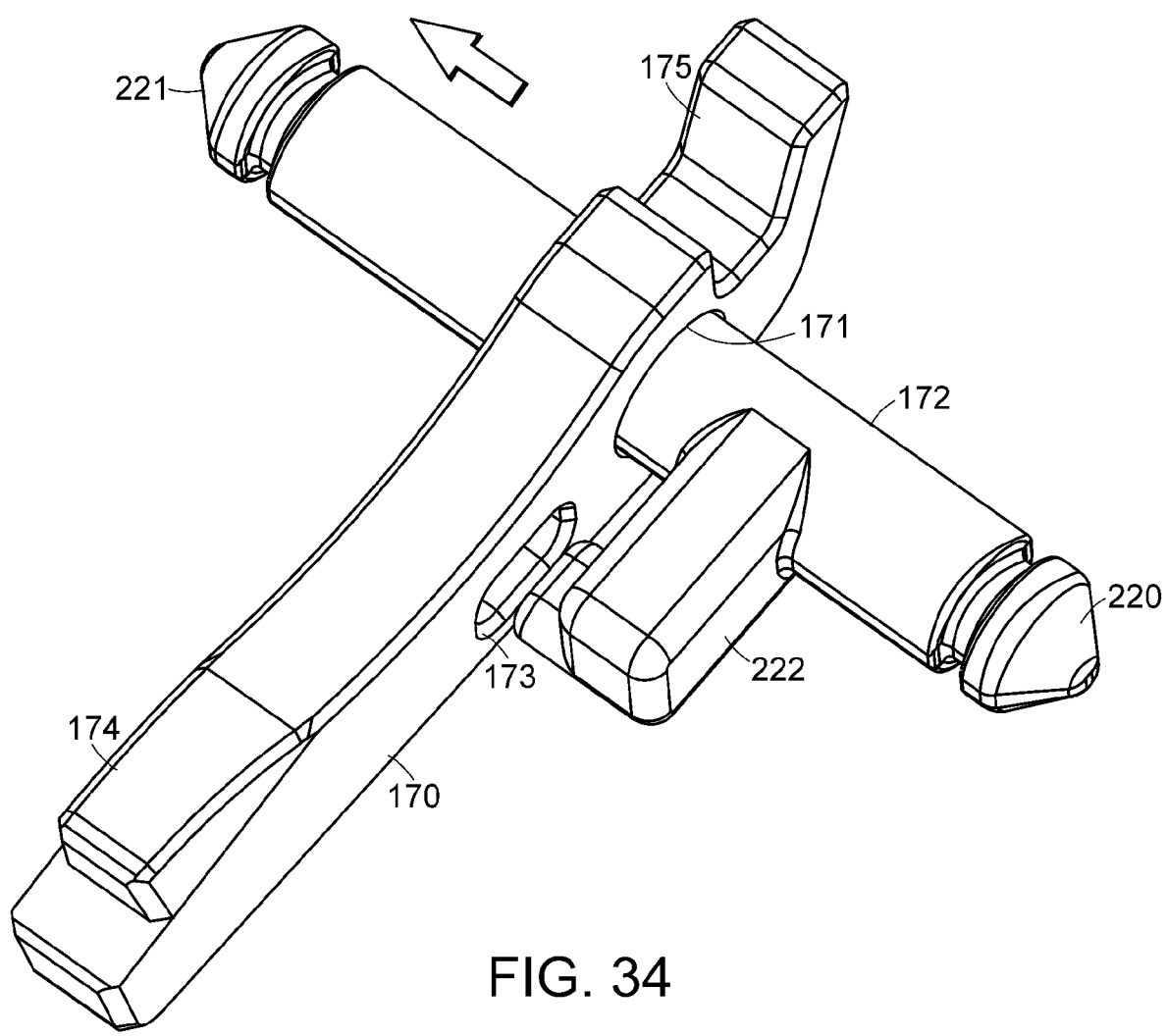
FIG. 34 is a perspective view of the pawl and firing pin of the firing drive of FIG. 19.
Figure 35:
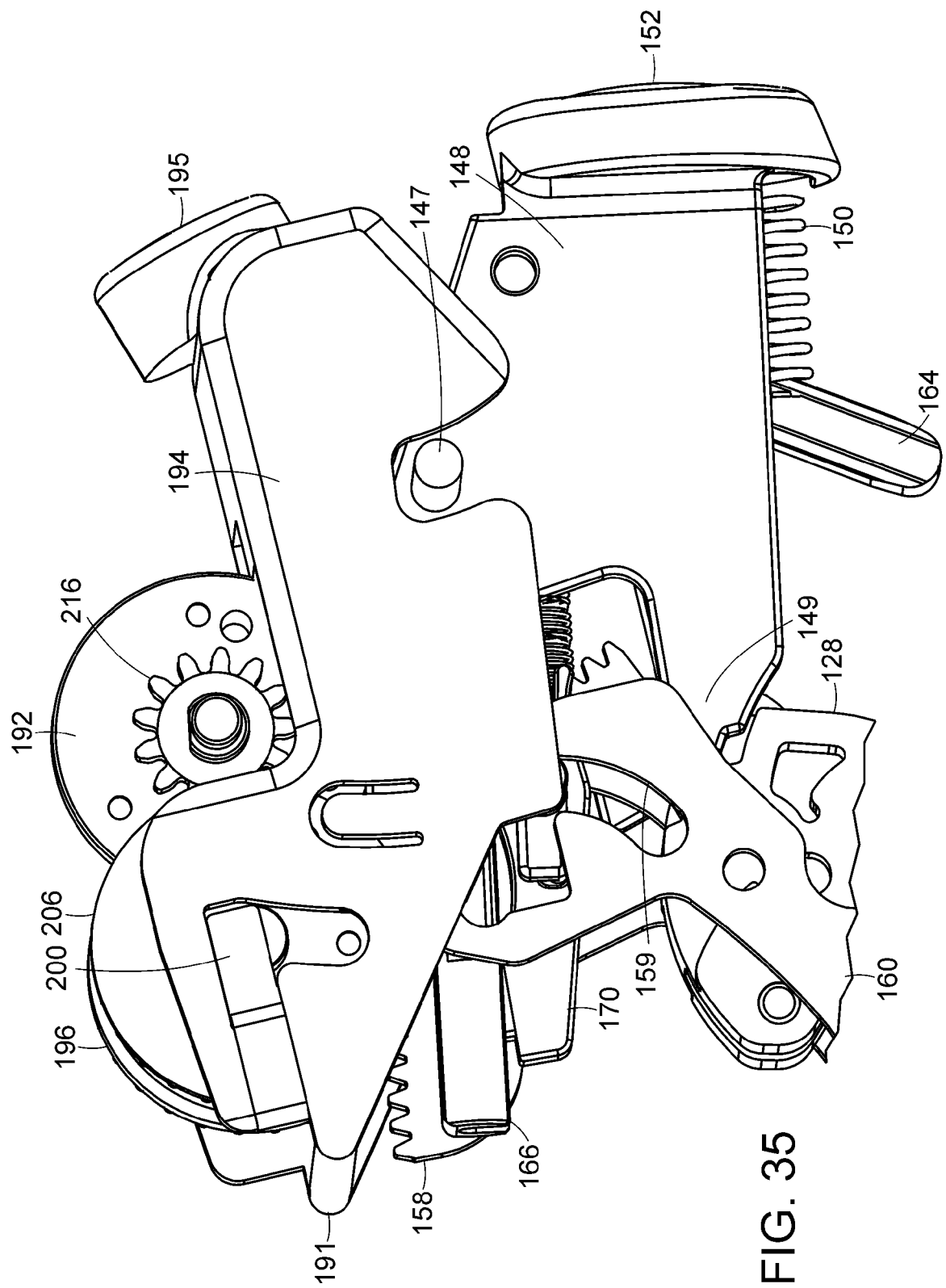
FIG. 35 is a perspective view of the return mechanism of FIG. 29 illustrating the return carriage in an actuated position and the firing trigger returned to its unactuated position.

When return carriage 194 is positioned in its unactuated position illustrated in FIGS. 29-31, firing trigger 160 can be configured to advance firing member 166 as described above and gear portion 158 of trigger 160 can be operatively engaged with trigger gear 196. In various embodiments, gear portion 158 and trigger gear 196 can be operably engaged such that a rotation of trigger 160 about pin 161 can drive trigger gear 196 about an axis defined by return pin 198. In at least one embodiment, when return carriage 194 is in its unactuated position, trigger gear 196 can be configured to rotate freely about return pin 198 such that the rotation of trigger gear 196 is not transmitted, or at least not substantially transmitted, to return pin 198. More particularly, referring to FIG. 30, key 199 of return pin 198 can be biased out of engagement with trigger gear 196 such that the rotation of trigger gear 196 is not transmitted to key gear 206 and reel 192. As a result, an actuation of trigger gear 160 does not rotate, or at least substantially rotate, reel 192 when return carriage 194 is in its unactuated position.

After the cutting member and the staple driver have been advanced within end effector 106, return carriage 194 can be moved into its actuated position. In various embodiments, referring to FIG. 30, reel 192 can include cam member 202 extending therefrom which can contact return carriage 194 and rotate return carriage 194 downwardly. In at least one embodiment, cam member 202 can contact return carriage 194 during the final actuation of trigger 160 which advances the cutting member and staple driver within end effector 106. In at least one such embodiment, cam member 202 can contact return carriage 194 after the third actuation of firing trigger 160. In various embodiments, referring to FIGS. 32-35, when gear carriage 194 is moved into its actuated position, return carriage 194 can be configured to operably engage trigger gear 196 with reel 192. In at least one embodiment, referring to FIGS. 33 and 35, return carriage 194 can include biasing spring 200 where, when return carriage 194 is in its unactuated position, spring 200 can be located in the position illustrated in FIG. 33 and, when return carriage 194 is moved into its actuated position illustrated in FIG. 35, spring 200 can contact return pin 198 and bias return pin 198 toward trigger gear 196. In at least one embodiment, referring to FIG. 31, trigger gear 196 can include D-shaped cavity 197 therein which can, under certain circumstances explained below, receive key 199 extending from return pin 198 and operably engage trigger gear 196 with key gear 206 and reel 192. In various embodiments, the movement of return carriage 194 into its actuated position can be accompanied by an audio and/or tactile feedback to inform the surgeon that the return mechanism of the surgical instrument has been engaged with trigger 160.

Figure 36:
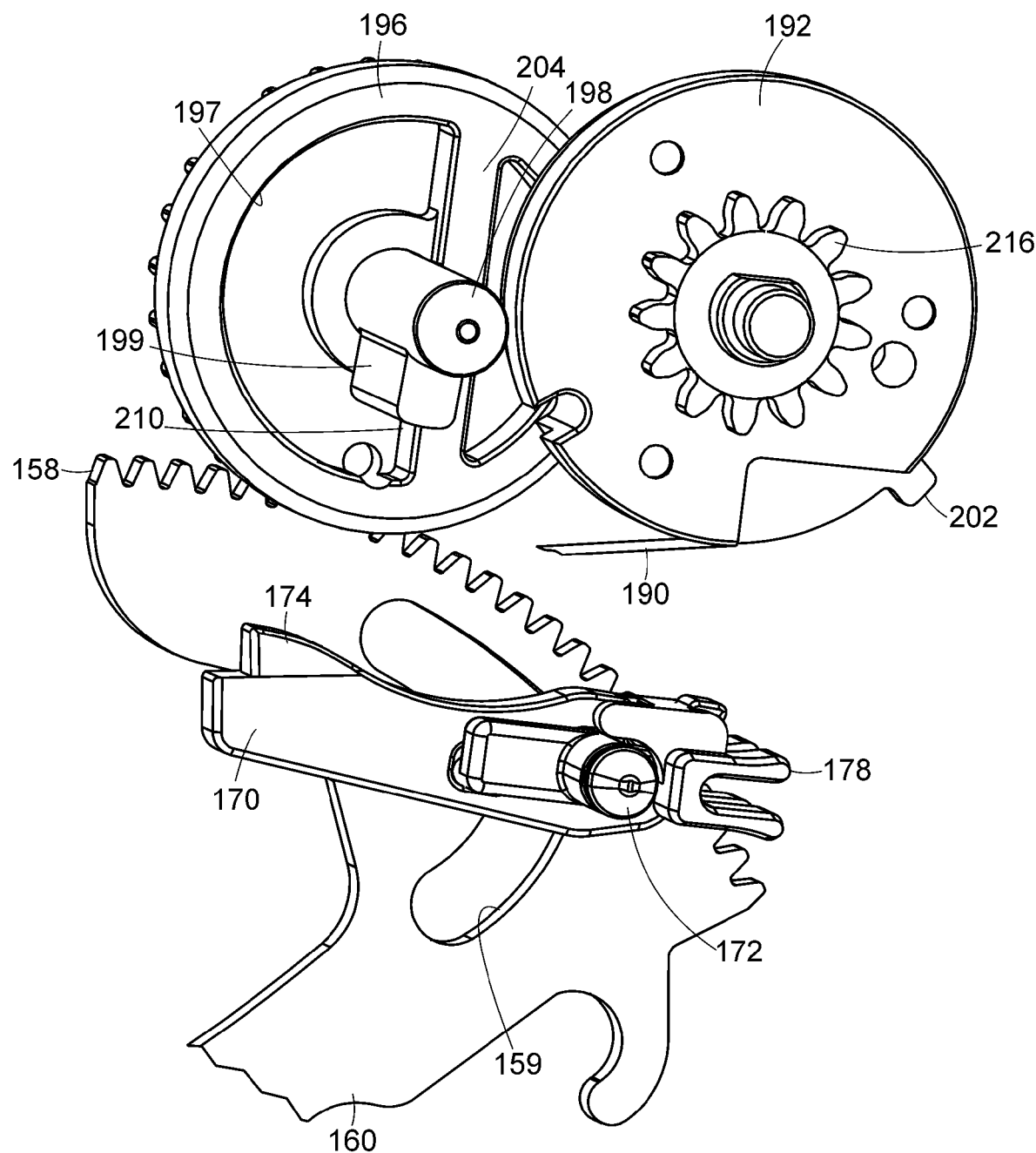
FIG. 36 is a partial perspective view of the return mechanism of FIG. 29 arranged in the configuration illustrated in FIG. 35 illustrating a return pin of the return mechanism operably engaged with the firing trigger.
Figure 37:
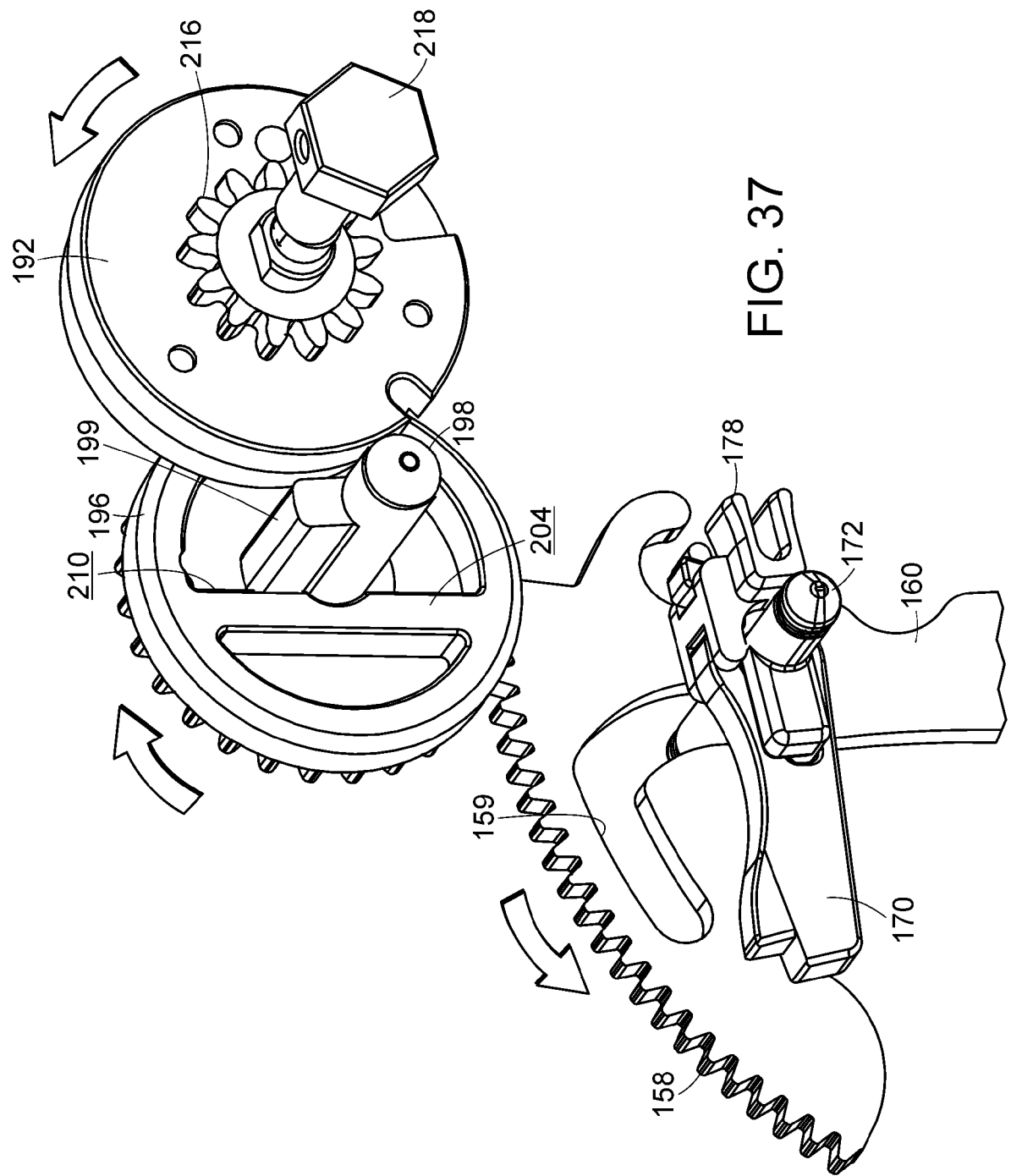
FIG. 37 is a partial perspective view of the return mechanism of FIG. 29 illustrating the firing trigger in an actuated position after rotating the return pin.
Figure 39:
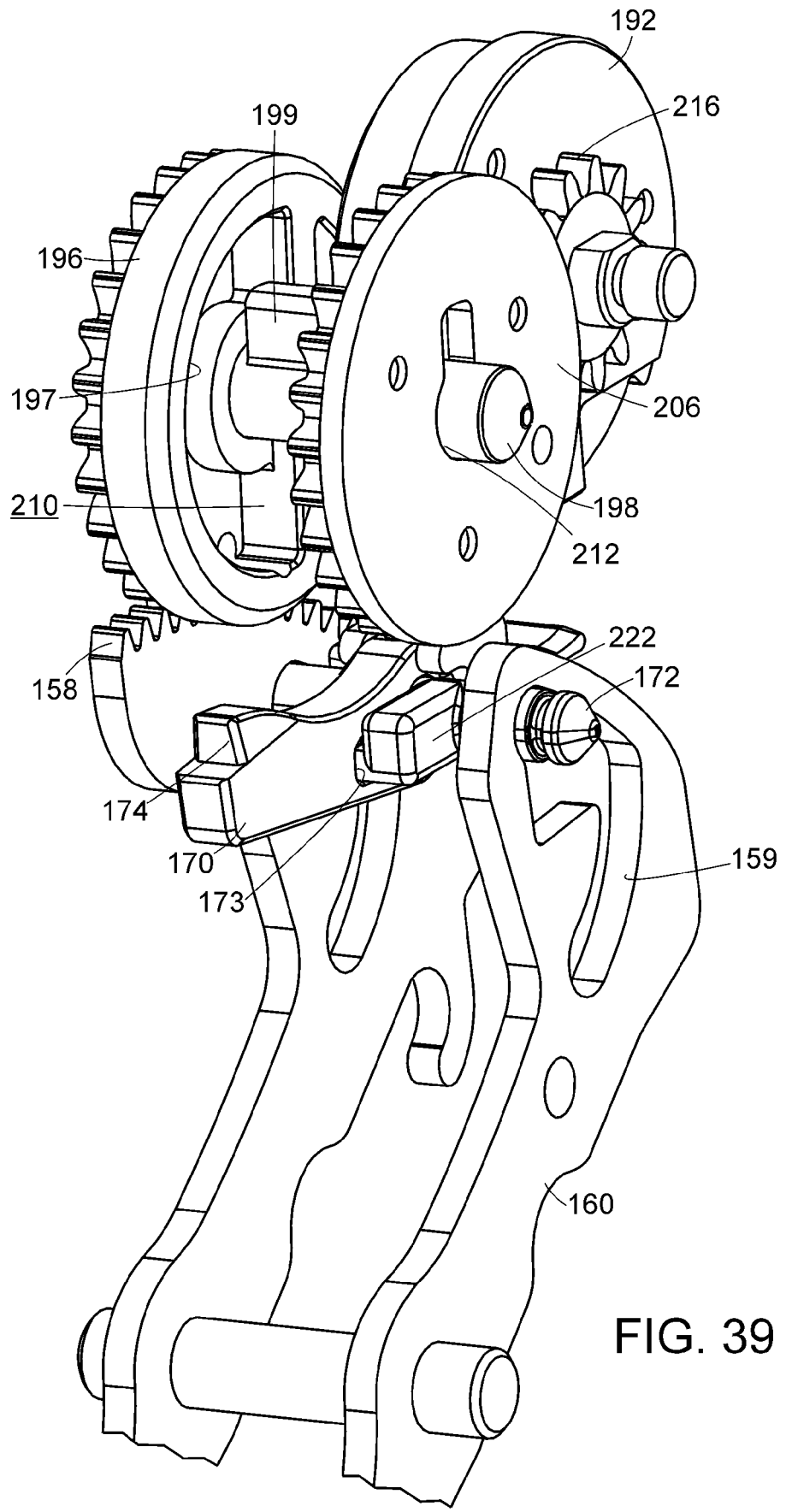
FIG. 39 is a partial perspective view of the return mechanism of FIG. 29 illustrating the firing trigger returned to its unactuated position.
Figure 40:
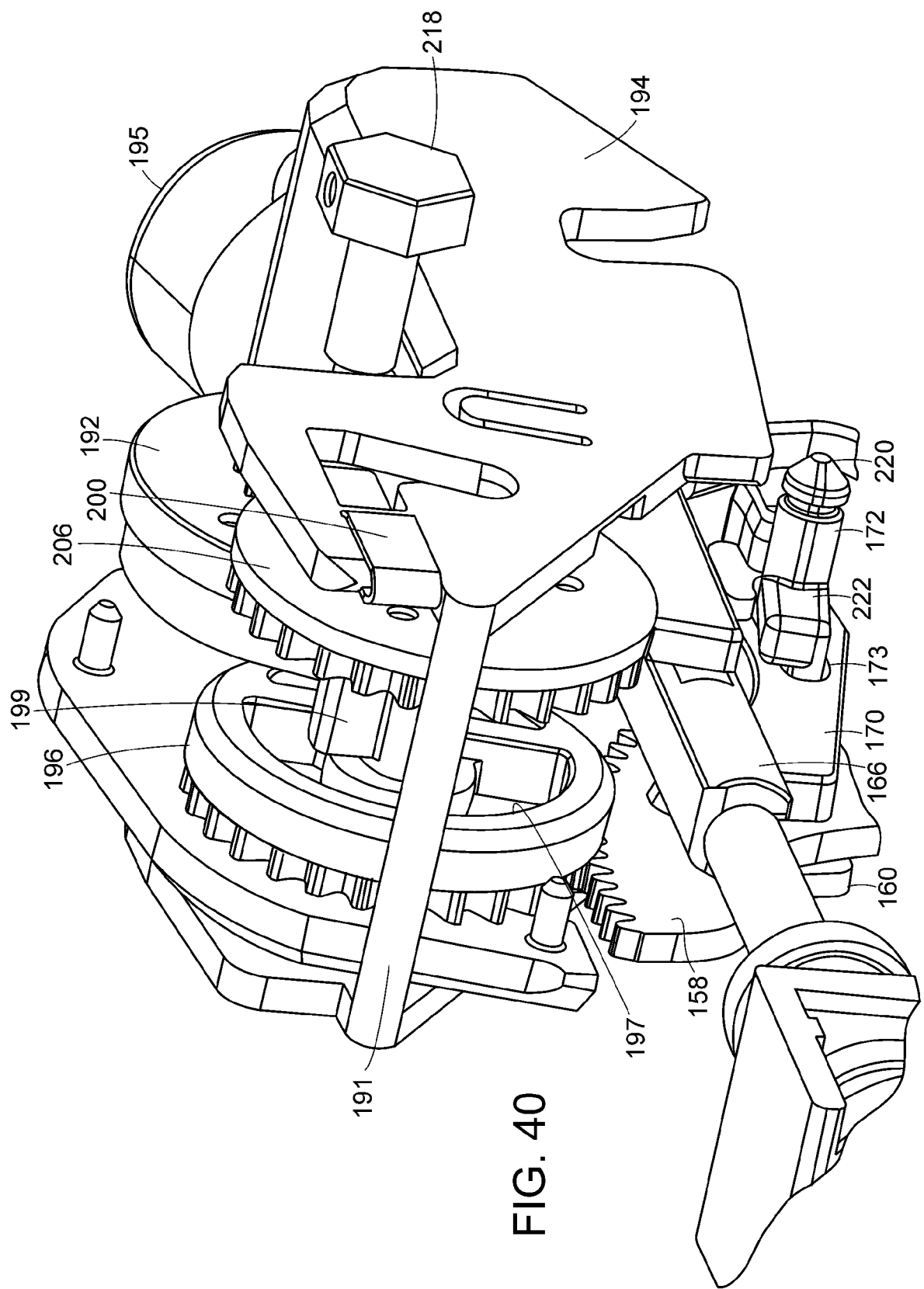
FIG. 40 is a perspective view of the return mechanism of FIG. 29 illustrating the return carriage returned to its unactuated position.
Figure 41:
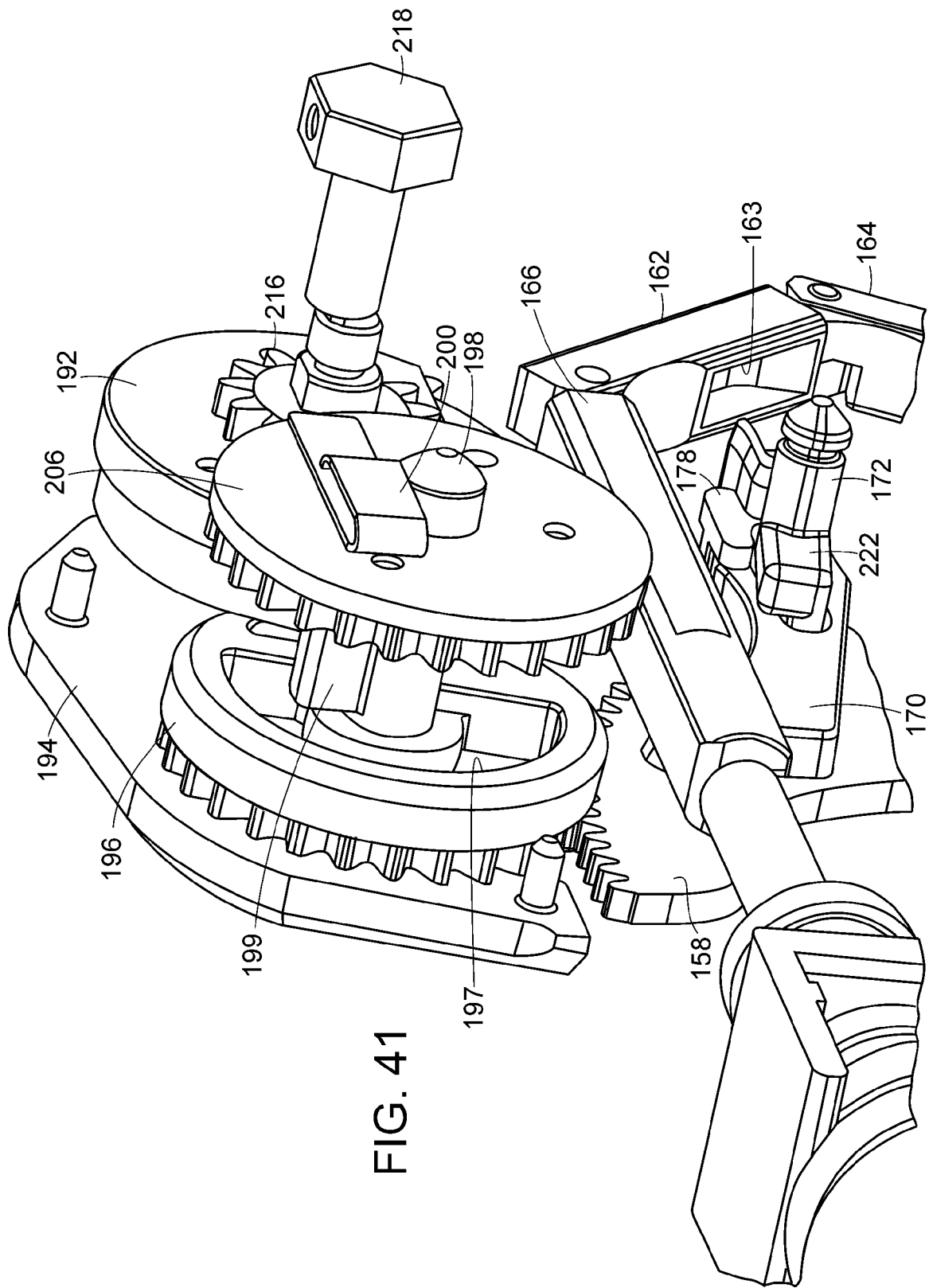
FIG. 41 is a perspective view of the return mechanism of FIG. 29 arranged in the configuration of FIG. 40 illustrating the relative relationship between a biasing spring and the return pin of the return mechanism with some components of the return mechanism removed.
Figure 42:
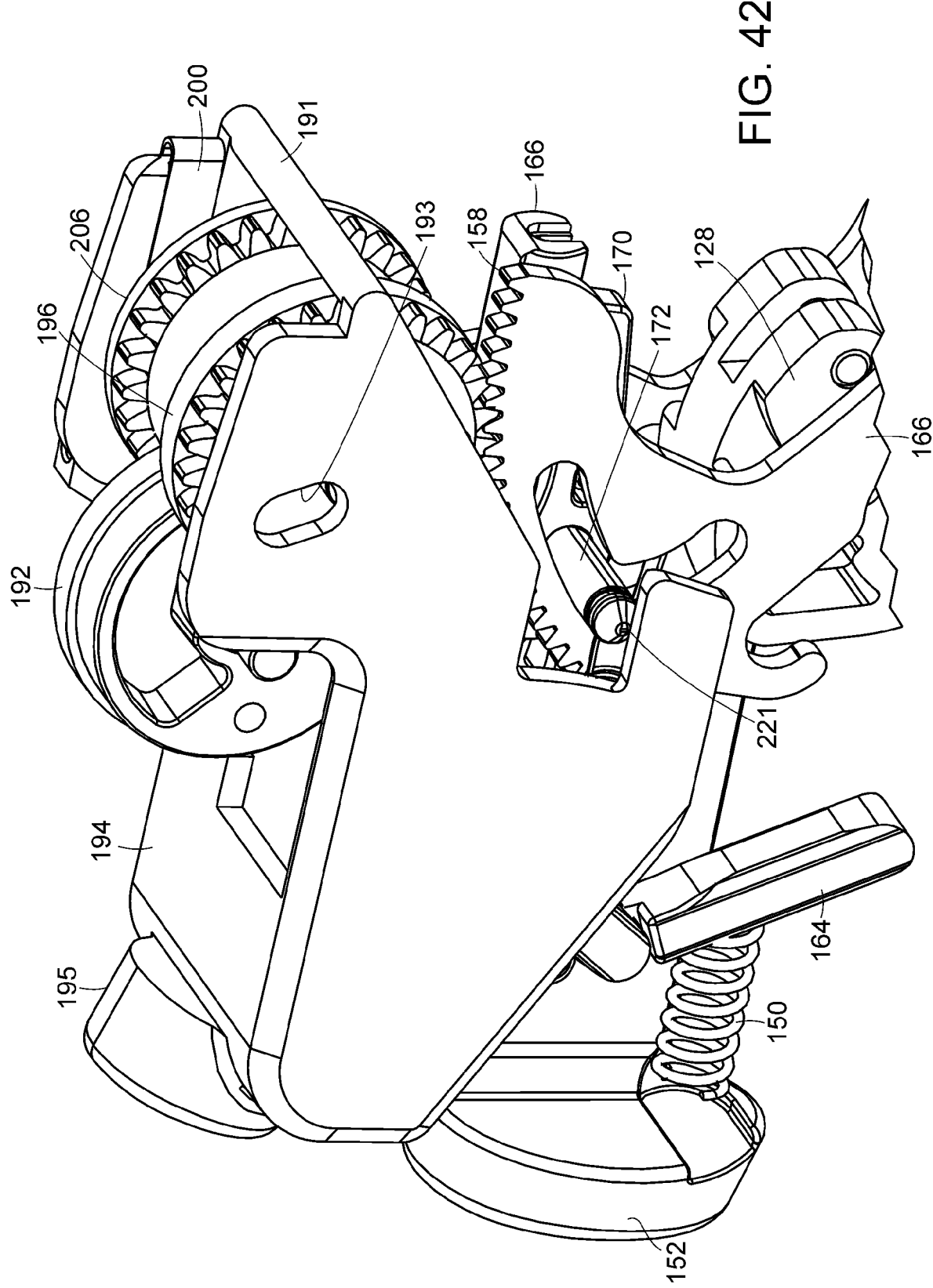
FIG. 42 is a perspective view of the return mechanism of FIG. 29 arranged in the configuration of FIG. 40 illustrating the return carriage operably engaged with the firing pin of the firing drive and the return pin of the return mechanism in order to reset the firing drive and the return mechanism to the their initial configurations.

Further to the above, when return pin 198 is slid toward trigger gear 196, D-shaped cavity 197 can be positioned such that key 199 does not immediately enter cavity 197. On the contrary, referring to FIG. 31, spring 200 can bias return pin 198 such that key 199 initially abuts face 204 of trigger gear 196. After trigger 160 is released and is returned to its unactuated position, however, D-shaped cavity 197 can be rotated and aligned with key 199 such that spring 200 can bias key 199 into cavity 197 as illustrated in FIG. 36. In at least one embodiment, referring to FIG. 31, when return pin 198 is slid toward trigger gear 196, an end of return pin 198 can be received in slot 193 in return carriage 194 as illustrated in FIG. 32. After key 199 has been inserted into cavity 197, a subsequent actuation of trigger 160 can cause drive surface 210 of D-shaped cavity 197 to abut key 199 and rotate return pin 198 to a position illustrated in FIGS. 37 and 38. In effect, an actuation of trigger 160, in at least one embodiment, can rotate key 199 approximately half a revolution such that key 199, which is initially extending substantially downwardly (FIG. 36), can be rotated such that key 199 is extending substantially upwardly (FIG. 37). Thereafter, trigger 160 can be released and trigger gear 194 can be rotated relative to key 199 where key 199 can remain oriented in a substantially upward direction as illustrated in FIGS. 39-41.

Figure 38:
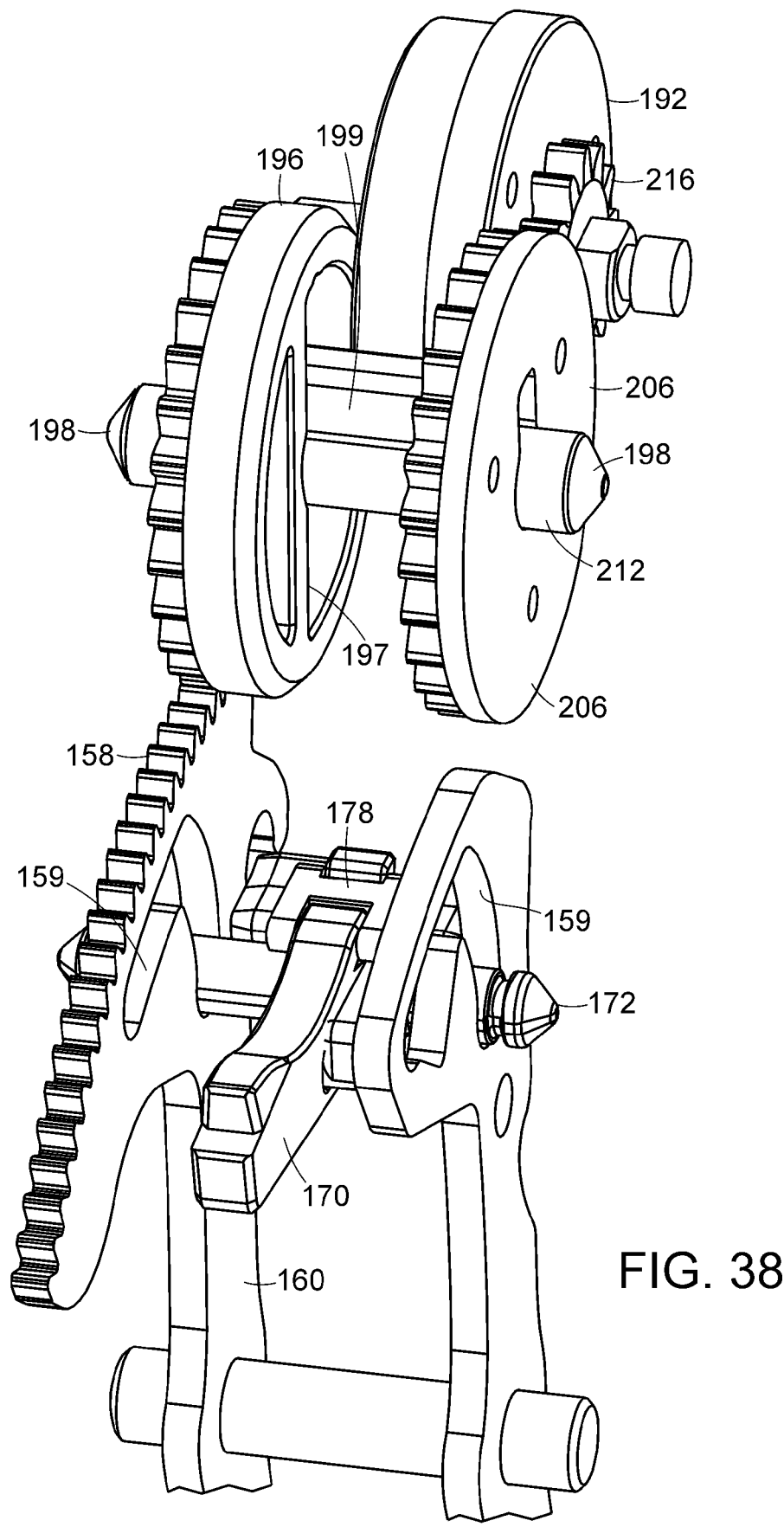
FIG. 38 is an additional perspective view of the return mechanism of FIG. 29 arranged in the configuration illustrated in FIG. 37.

In various embodiments, referring primarily to FIG. 38, key gear 206 can be operably engaged with return pin 198 such that the rotation of return pin 198 can be transmitted to key gear 206. In at least one embodiment, key gear 206 can include key-shaped aperture 212 which can be configured to slidably receive key 199 of return pin 198. In at least one such embodiment, key 199 can be operably engaged with both recess 197 of trigger gear 196 and aperture 212 of key gear 206 when return pin 198 is engaged with trigger gear 196. In various alternative embodiments, key gear 206 can be fixedly mounted to return pin 198. In such embodiments, when return pin 198 is slid relative to trigger gear 196, key gear 206 can also be slid relative to trigger gear 196. In various embodiments, referring generally to FIG. 38, reel 192 can include spur gear 216 mounted thereto, where spur gear 216 can be operatively engaged with key gear 206 such that the rotation of key gear 206 can be transmitted to reel 192. In at least one embodiment, key gear 206, when it is slid toward trigger gear 196 as described above, can be slid into operative engagement with reel 192. In alternative embodiments, spur gear 216 can be configured such that key gear 206 is in operative engagement therewith regardless of whether key gear 206 has been biased toward trigger gear 196.

As a result of the above, when return carriage 194 is positioned in its actuated position illustrated in FIG. 32, an actuation of trigger 160 can rotate reel 192 and wind band 190 around at least a portion thereof. In the event that key 199 cannot be operably engaged with trigger gear 196 when return carriage 194 is actuated, reel 192 can be rotated manually to retract band 190. In at least one such embodiment, referring to FIGS. 33 and 37, bolt, or fastener, 218 can be operatively engaged with reel 192 such that the rotation of bolt 218 can effect rotation of reel 192. In various embodiments, a surgeon can insert bolt 218 through an opening in surgical instrument housing 103 and engage bolt 218 with reel 192. In at least one embodiment, surgical instrument 100 can further include a counting mechanism (not illustrated) which can count the actuations of trigger 160 and, in at least one such embodiment, bolt 218, for example, can be operably engaged with the counting mechanism to rotate reel 192. In various embodiments, as a result, the surgical instrument can include a first, or primary, actuator for winding reel 192 and a second actuator which can be configured to wind reel 192 in lieu of the first actuator.

In various embodiments, as described above, reel 192 can be configured to pull band 190 and retract firing member 166 and firing links 162 and 164 proximally. More particularly, as described above, firing member 166 and firing links 162 and 164 can be retracted relative to pawl 170 in order to reposition firing member 166 and firing links 162 and 164 in their starting positions. In such embodiments, especially in embodiments where pawl 170 is pivotable as described above, the return mechanism of surgical instrument 100 can be further configured to hold pawl 170 out of operative engagement with firing member 166 and firing links 162 and 164 while they are moved relative to pawl 170. More particularly, when return carriage 194 is moved into its actuated position illustrated in FIG. 35, return carriage 194 can be configured to contact an end of firing pin 172 and slide firing pin 172 toward pawl 170 such that firing pin 172 engages pawl 170 and prevents pawl 170 from pivoting upwardly. More particularly, referring to FIG. 34, firing pin 172 can include first end 220 which can include a beveled and/or rounded surface, for example, where, when return carriage 194 contacts first end 220, return carriage 194 can push firing pin 172 toward pawl 170. In at least one embodiment, pawl 170 can include recess 173 which can be configured to receive key 222 extending from firing pin 172 when firing pin 172 is moved toward pawl 170. When key 222 and recess 173 are operatively engaged, firing pin 172 can prevent pawl 170 from pivoting upwardly into engagement with firing member 166 and firing links 162 and 164.

After firing member 166 and firing links 162 and 164 have been retracted, a new staple cartridge 110 can be secured in end effector 106 and surgical instrument 100 can be reset such that it can be used to incise and staple soft tissue once again. In various embodiments, referring to FIGS. 39-42, return carriage 194 can be moved from its actuated position illustrated in FIG. 32 to its unactuated position illustrated in FIG. 40. In at least one embodiment, return carriage 194 can be rotated, or pivoted, upwardly when a force is applied to button portion 195. Alternatively, return carriage 194 can be moved upwardly when, referring to FIG. 29, trigger lock 148 is rotated upwardly to disengage follower portion 149 from closure trigger 128 in order to reopen end effector 106 as described above. More particularly, when a force is applied to button portion 152 of trigger lock 148, trigger lock 148 can be rotated upwardly such that projection 147 extending therefrom can contact return carriage 194 and move return carriage 194 upwardly as well. In either event, referring to FIG. 42, when return carriage 194 is moved upwardly into its unactuated position, return carriage 194 can disengage firing pin 172 from pawl 170 and, in addition, disengage return pin 198 from trigger gear 196. More particularly, return carriage 194 can be configured to abut beveled, or rounded, end 221 of firing pin 172 such that, when return carriage 194 is rotated upwardly, return carriage 194 can slide return pin 172 away from pawl 170 and disengage key 222 from recess 173. Similarly, when return carriage 194 is moved upwardly, a side wall of slot 193 can be configured to contact an end of return pin 198 and slide return pin 198 away from trigger gear 196 to disengage key 199 from D-shaped recess 197. In short, in at least the illustrated embodiment, when button portion 152 of lock member 148 is depressed and return carriage 194 is moved upwardly, the surgical instrument can be reset and can be reused once again.

Although the surgical instruments described above can be reset after the cutting member and staple driver have been completely advanced within end effector 106, button portion 195 of return carriage 194, for example, can be depressed after the cutting member and staple driver have been only partially advanced within end effector 106. In various embodiments, return carriage 194 can further include guide pin 191 extending between opposite sides of return carriage 194. In at least one such embodiment, guide pin 191 can be slidably received within guide slot 185 (FIG. 31) in frame 184 such that slot 185 and pin 191 can define a path for return carriage 194. In various embodiments, guide pin 191 and guide slot 185 can be configured to assure that return carriage 194 engages firing pin 172 and return pin 198 and resets the surgical instrument when return carriage 194 is moved from its actuated position to its unactuated position as described above.

Figure 43:
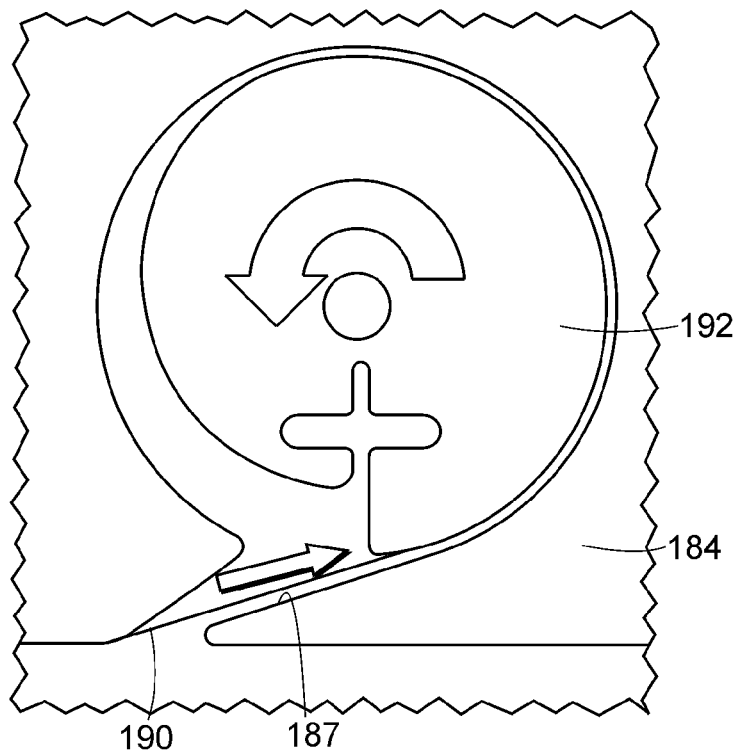
FIG. 43 is a detail view of a reel of the return mechanism of FIG. 29 illustrating the relative relationship between a return band of the return mechanism and the stapler frame of FIG. 26.
Figure 44:
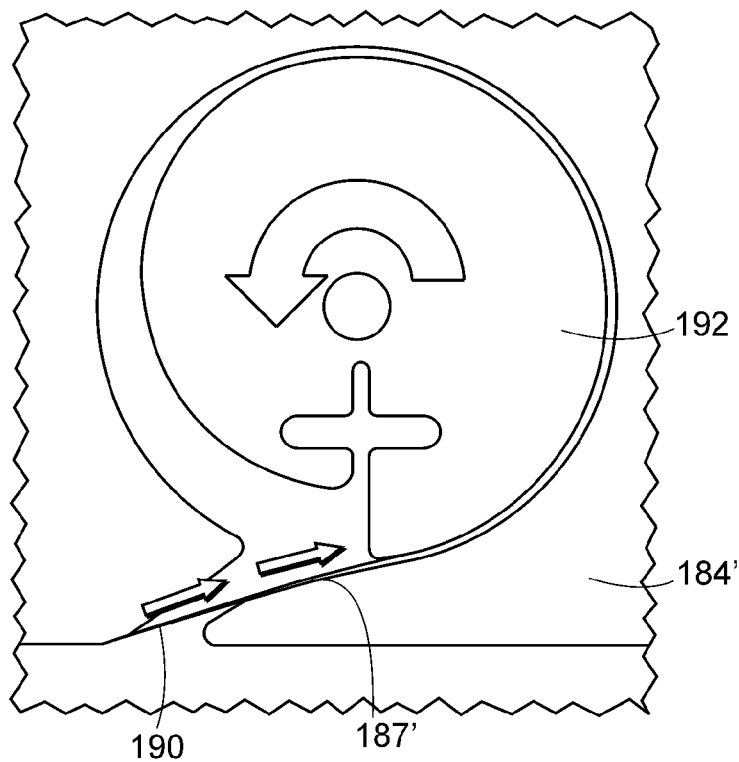
FIG. 44 is a detail view of the reel of FIG. 43 illustrating the relative relationship between the return band and an alternative embodiment of the stapler frame of FIG. 26.
Figure 45:
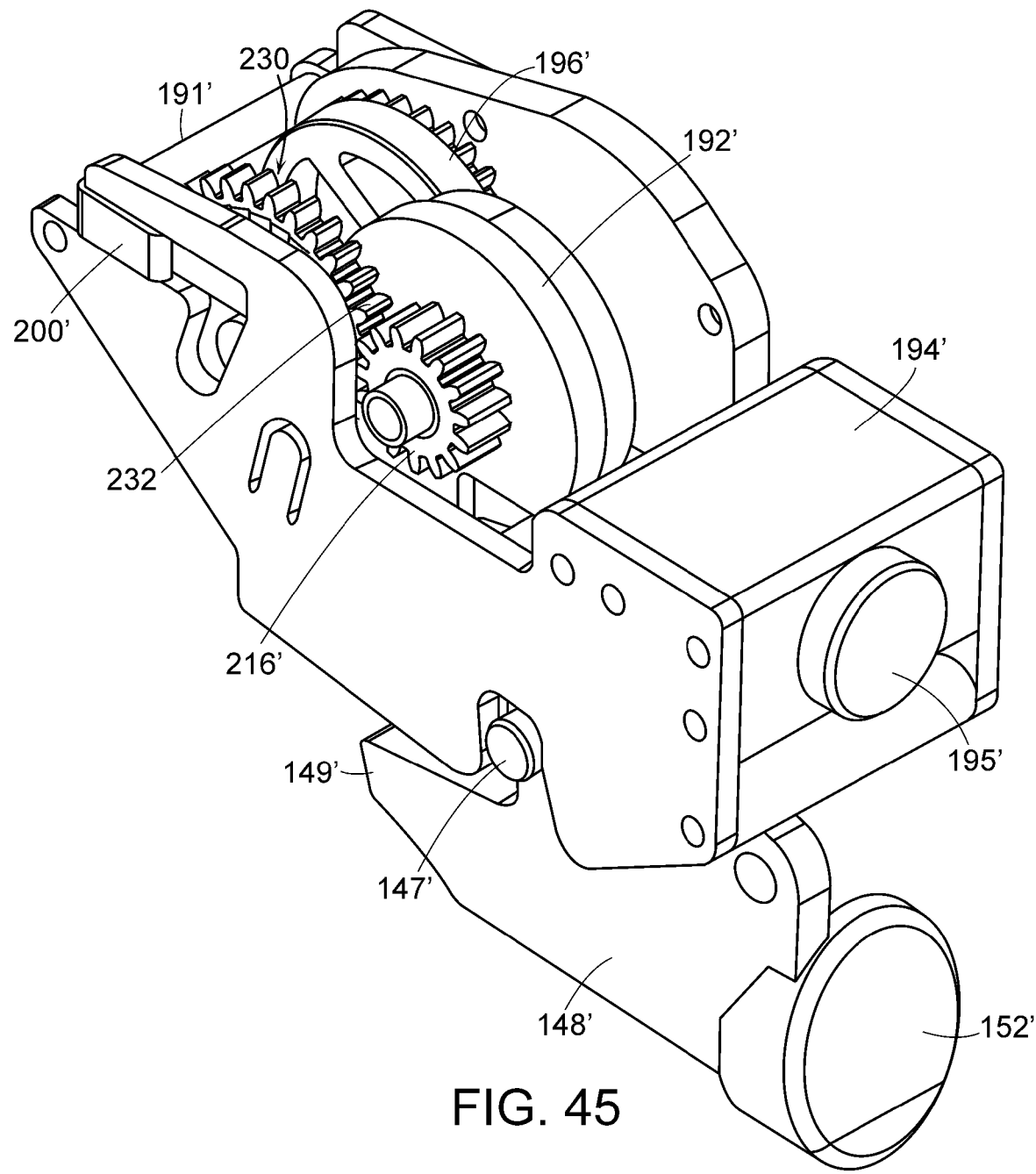
FIG. 45 is a perspective view of a return mechanism of a surgical instrument in accordance with an alternative embodiment of the present invention having an anti-back-up ratchet mechanism.
Figure 46:
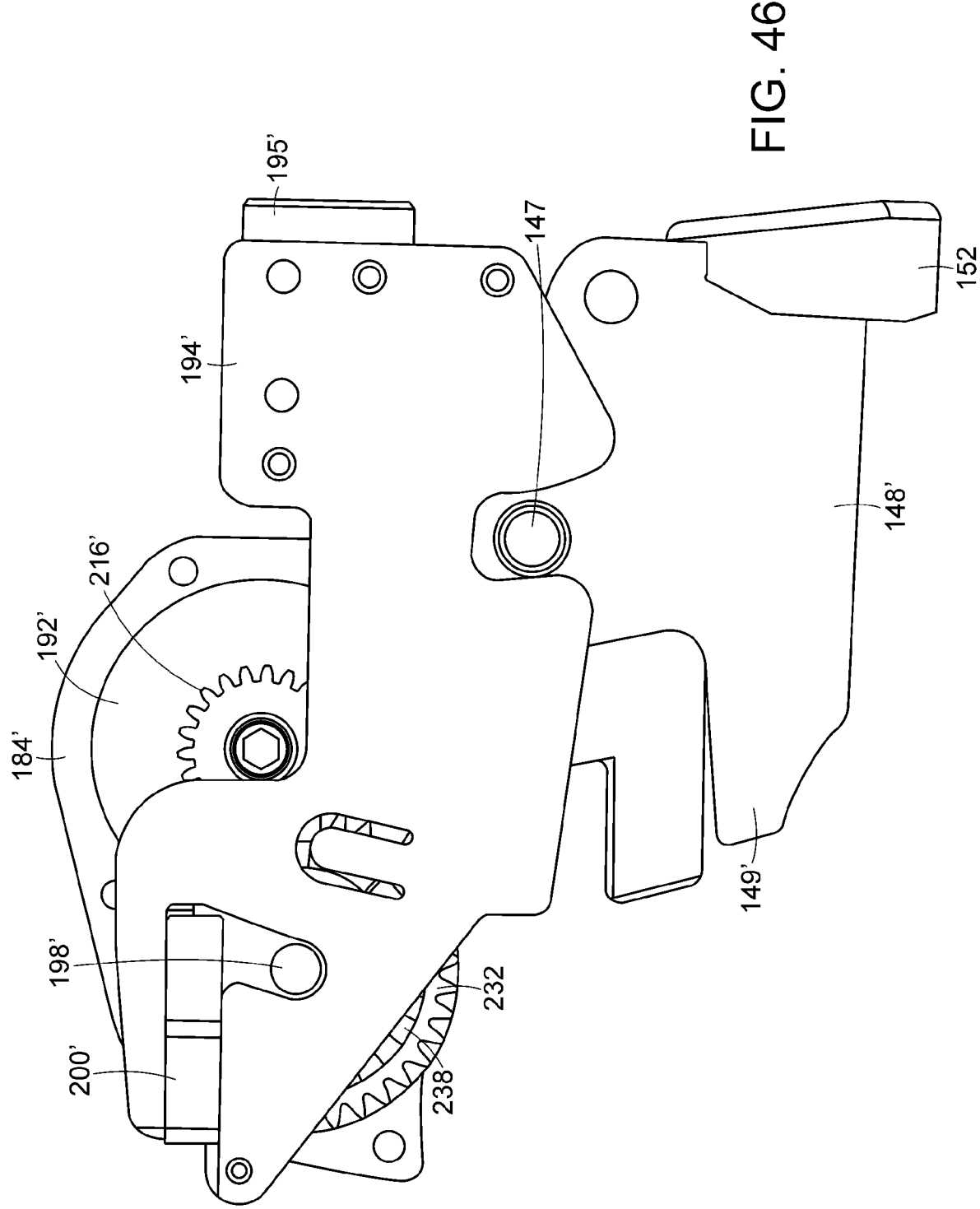
FIG. 46 is an elevational view of the return mechanism of FIG. 45 having a return carriage in an unactuated position.

In various embodiments, surgical instrument 100 can further include a brake for preventing, or at least partially inhibiting, the firing drive from advancing and/or retracting the cutting member and staple driver, for example, within end effector 106. In at least one embodiment, referring to FIG. 43, frame 184 can include brake surface 187 where brake surface 187 can be configured to apply a braking force to band 190. More particularly, when band 190 is pulled proximally and/or distally as described above, frame 184 can be configured such that band 190 slides over brake surface 187 and a friction force is created therebetween. In various embodiments, referring to FIG. 44, brake surface 187' can be configured such that the path of band 190 between firing member 166 and reel 192 is interrupted by brake surface 187' and a significant normal force can be applied to band 190.

In at least one embodiment, band 190 can be engaged with brake surface 187' when band 190 is at rest such that a static friction force between band 190 and brake surface 187' can prevent, at least initially, band 190 from moving relative to brake surface 187' when a pulling force is applied to band 190. When the pulling force applied to band 190 exceeds the static friction force, band 190 can be moved relative to brake surface 187'. Such embodiments may be particularly useful when trigger 160 is actuated more than one time to advance the cutting member and/or staple driver within end effector 106. More particularly, after an actuation of trigger 160, pawl 170 can be retracted relative to firing member 166 as described above and, in various embodiments, the friction force between band 190 and brake surface 187' can prevent, or at least partially inhibit, firing member 166 and/or firing links 162 and 164 from moving proximally, and/or distally, as pawl 170 is retracted. As a result of the above, the alignment between tooth 174 of pawl 170 and the recesses in firing member 166 and firing links 162 and 164 can be maintained when pawl 170 is moved relative thereto.

Similarly, in at least one embodiment, the stiffness of band 190 can also assist in holding firing member 166 and firing links 162 and 164 in position. More particularly, in order for firing member 166 to 'back up', or move proximally, firing member 166 would have to push band 190 proximally and, in effect, wind band 190 around reel 192. In various embodiments, the stiffness of band 190 can be such that a significant force to wind band 190 around reel 192 is required and, as a result, firing member 166 can be held in place. To further increase the force required to wind band 190 around reel 192, referring to FIG. 44, the path of band 190 can be controlled such that is not wound onto reel 192 in a tangential direction. More particularly, if the path of band 190 is such that it is wound onto reel 192 in a non-tangential direction, a portion of the force transmitted through band 190 will be lost thus resulting in a poor mechanical advantage for winding reel 192.

In various embodiments, surgical instrument 100 can include a brake which can be engaged with reel 192, or any other suitable component of the firing drive, to prevent firing member 166 and/or firing links 162 and 164 from being retracted unintentionally, for example. In at least one embodiment, although not illustrated, the brake can be moved between a first position and a second position, where, when the brake is in the first position, the brake can apply a first braking force to band 190, for example. In at least one such embodiment, the brake can apply, when it is in the second position, a second braking force to band 190, for example, which can be greater than or less than the first braking force. In various alternative embodiments, the brake may not be engaged with band 190 or any other portion of the firing drive when the brake is in the second position. In various embodiments, although not illustrated, surgical instrument 100 can include a detent mechanism which can apply a braking force to reel 192 and/or band 190. In at least one such embodiment, the detent mechanism can include a ball detent and a spring member for biasingly engaging the ball detent against reel 192 and/or band 190.

Figure 47:
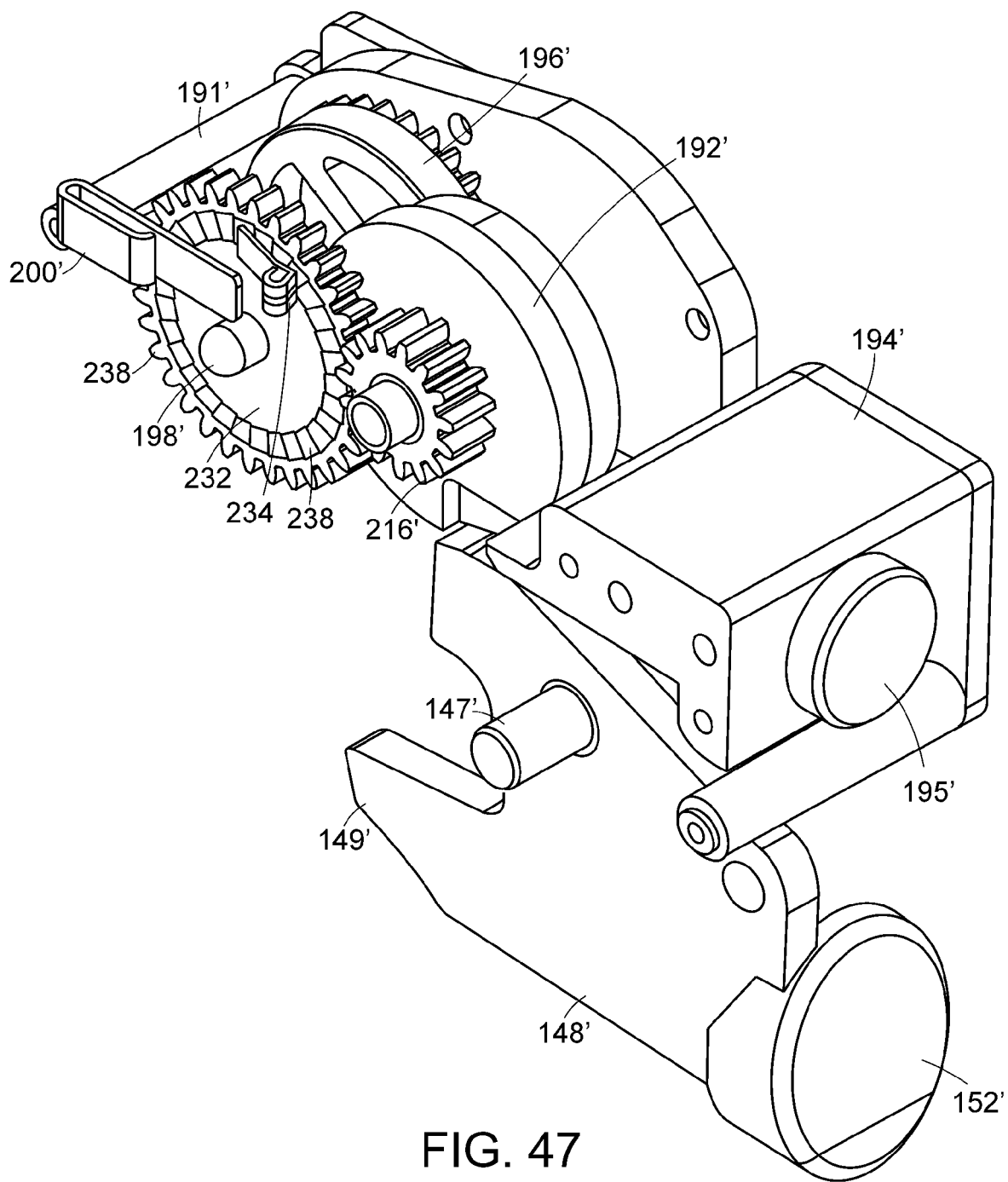
FIG. 47 is a perspective view of the return mechanism of FIG. 45 with some components of the surgical instrument removed.
Figure 48:
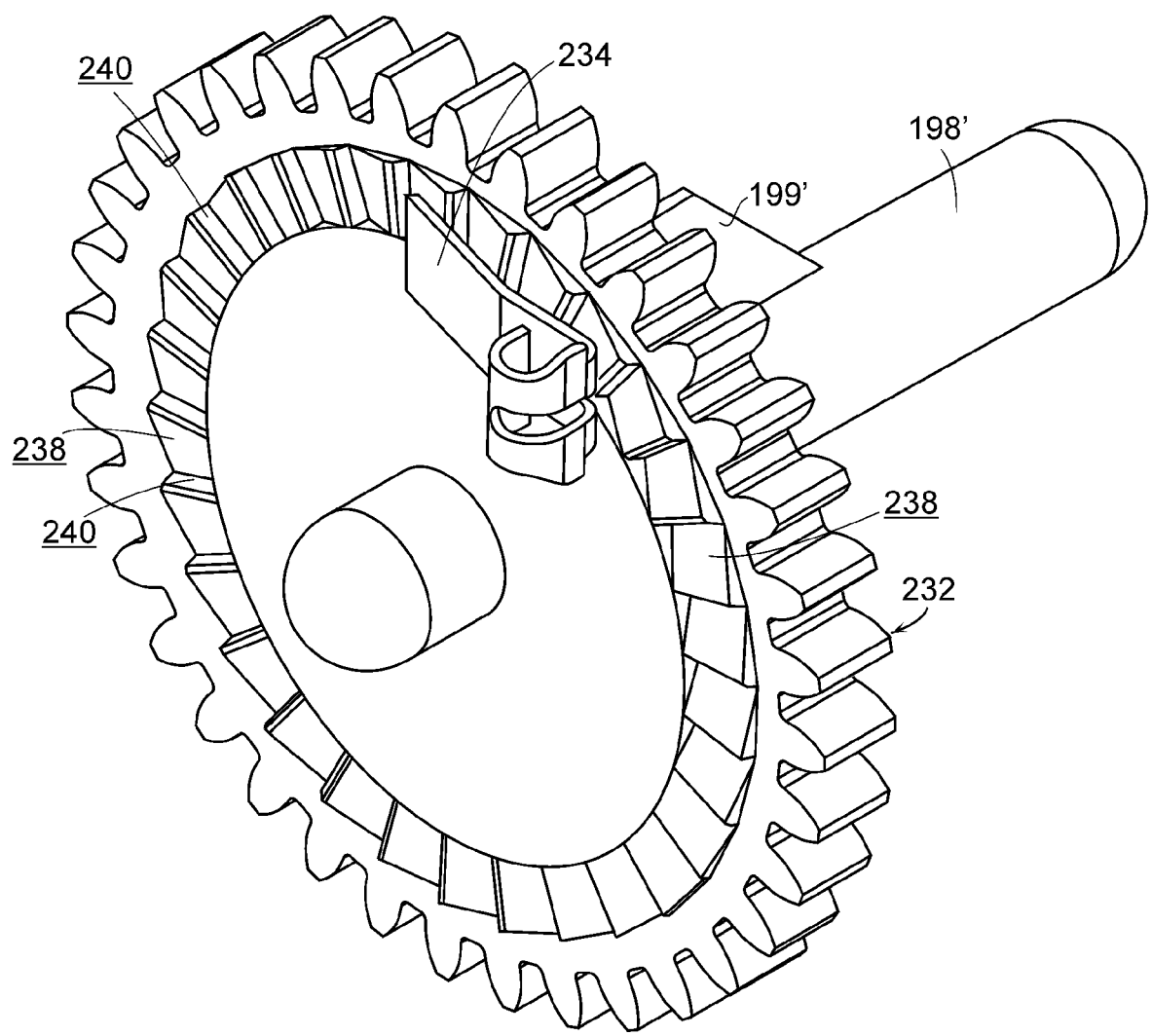
FIG. 48 is a perspective view of a return gear, return pin, and anti-back-up pawl of the ratchet mechanism of FIG. 45.
Figure 49:
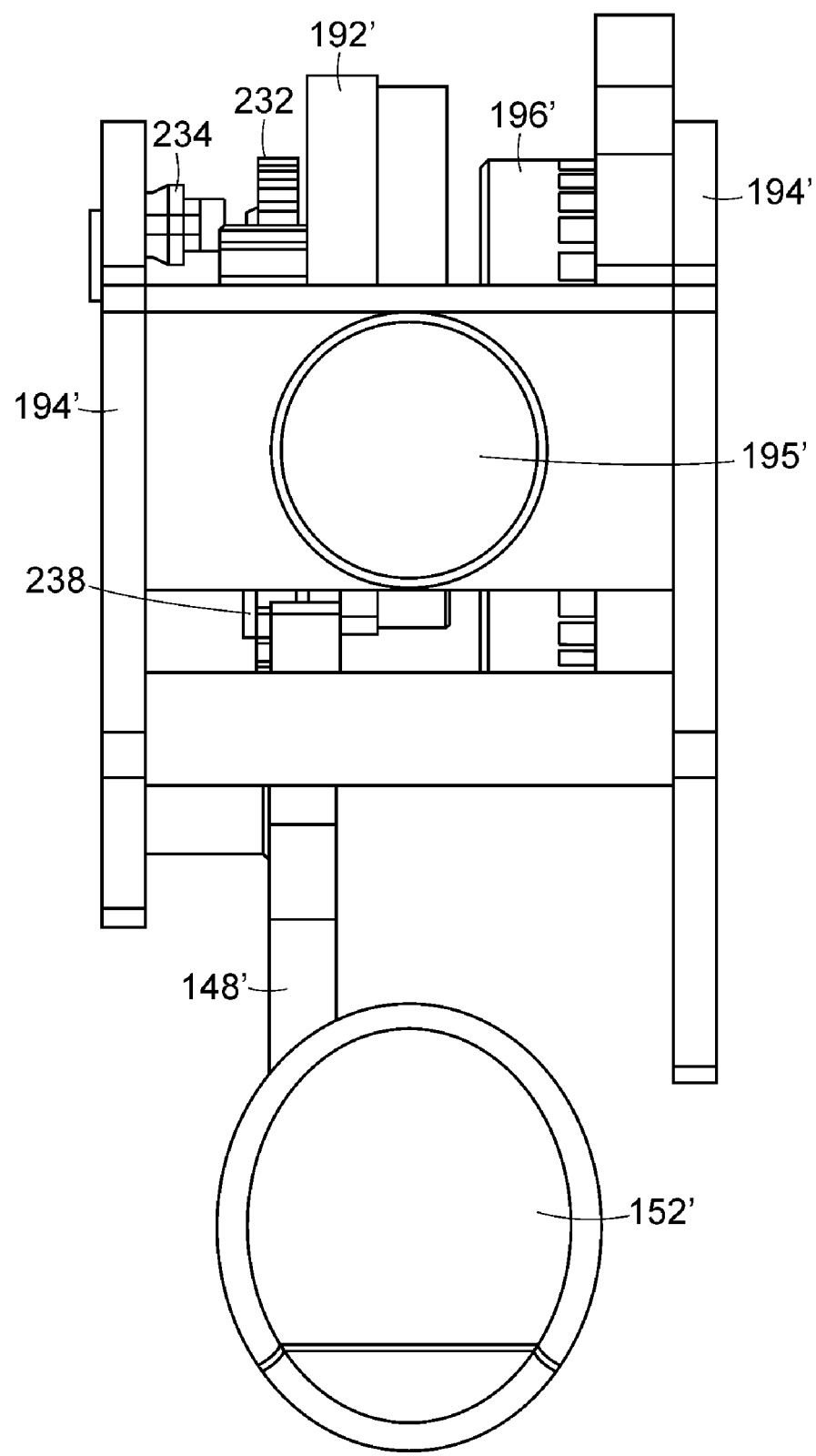
FIG. 49 is another elevational view of the return mechanism of FIG. 45.

In various embodiments, surgical instrument 100 can include a ratchet which can allow reel 192 to turn in a first direction but can, in various circumstances, prevent reel 192 from turning in a direction opposite the first direction. In at least one embodiment, referring to FIGS. 45-49, surgical instrument 100 can include ratchet assembly 230, where ratchet assembly 230 can include ratchet wheel 232 and ratchet pawl 234. In various embodiments, ratchet wheel 232 can operate in substantially the same way as key gear 206 described above except that, referring primarily to FIGS. 47 and 48, ratchet wheel 232 can include ratchet teeth 236 which can, owing to a ratcheting engagement with ratchet pawl 234, prevent ratchet wheel 232 from being turned in a clockwise direction, for example, when return carriage 194' is in its unactuated position (FIG. 47). More particularly, each ratchet tooth 236 can include a flat surface 240 where, referring to FIG. 48, at least one of flat surfaces 240 can abut edge 235 of pawl 234 and thereby prevent ratchet wheel 232 from being rotated in a clockwise direction.

Each ratchet tooth 236 can further include an inclined surface 238, where inclined surfaces 238 can be configured to slide underneath pawl 234 when ratchet wheel 232 is turned in a counter-clockwise direction. As a result of the above, ratchet assembly 230 can allow band 190 to be pulled distally by firing member 166, for example, but prevent, or at least substantially inhibit, band 190 from being moved proximally, at least when return carriage 194 is in its unactuated position. When return carriage 194' is pivoted downwardly into its actuated position, as described above with regard to return carriage 194, ratchet wheel 232 can be slid toward trigger gear 196' and out of operative engagement with ratchet pawl 234. Thereafter, as a result, ratchet wheel 232 can be rotated in either a clockwise or counter-clockwise direction without interference, or at least substantial interference, from ratchet pawl 234. In various alternative embodiments where ratchet wheel 232 is not slid toward trigger gear 196', ratchet pawl 234 can be moved downwardly and out of operative engagement with ratchet teeth 236 when return carriage 194' is moved into its actuated position. In either event, when return carriage 194' is in its actuated position, trigger gear 196' and return pin 198' can rotate ratchet wheel 232 and cam 192' to retract band 190 and firing member 166.

Figure 50:
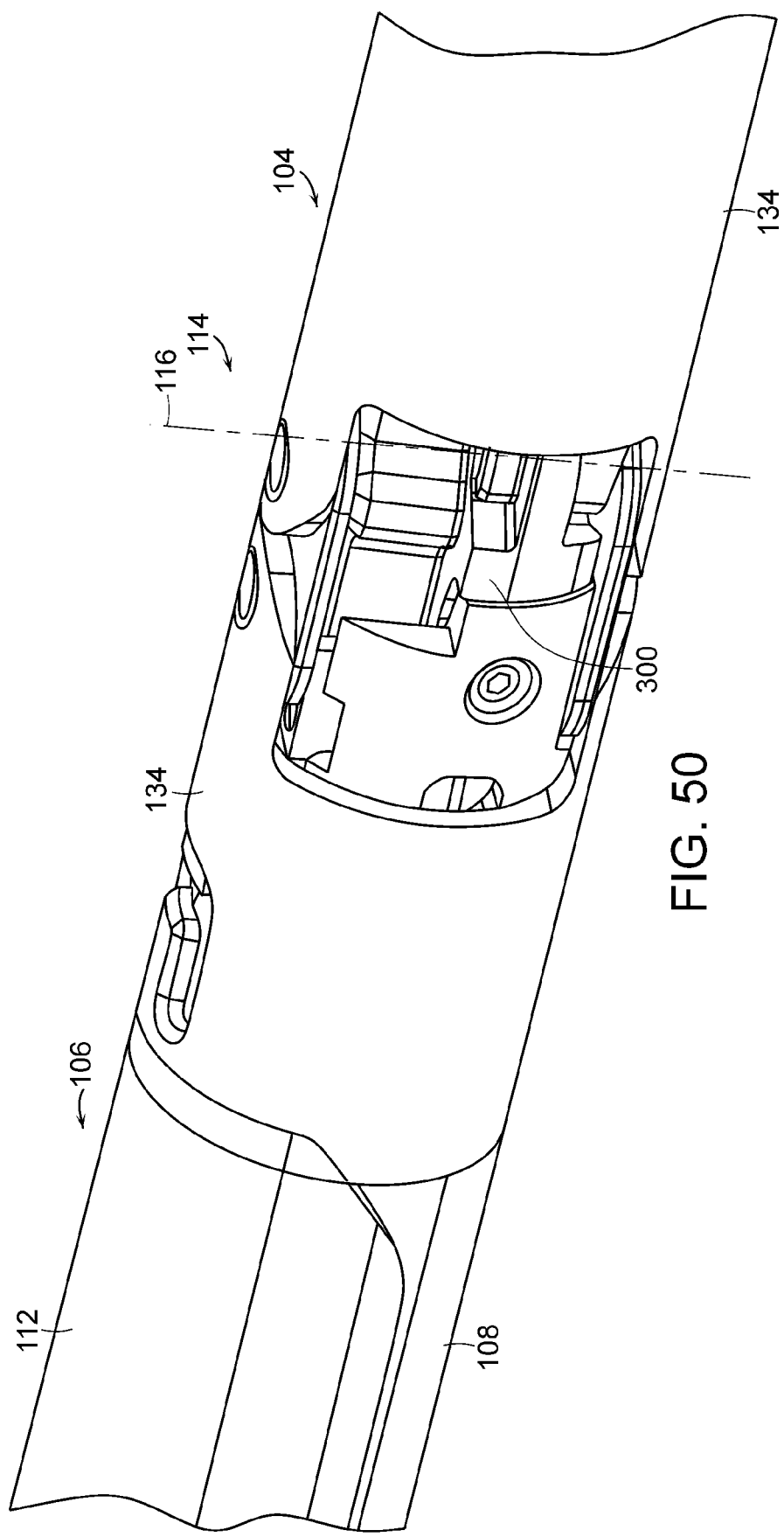
FIG. 50 is a perspective view of the articulation joint of FIG. 5.

In various embodiments, referring to FIG. 50, surgical instrument 100 can include end effector 106 and elongate shaft assembly 104, where end effector 106 and shaft assembly 104 can be pivotably connected by articulation joint 114. As outlined above, articulation joint 114 can allow end effector 106 to be moved, or articulated, relative to shaft assembly 106 about axis 116. In various circumstances, a surgeon can articulate end effector 106 to more easily access a surgical site within a patient's body. More particularly, a surgeon may insert end effector 106 and shaft assembly 104 through a cannula at least partially inserted into the patient's body and, once end effector 106 has passed through the cannula, end effector 106 can be pivoted, or articulated, in order to position end effector 106 relative to soft tissue, for example, in the surgical site that is to be stapled and/or incised. Once end effector 106 has been positioned, the relative relationship between end effector 106 and shaft assembly 104 can be fixed, or locked, by a locking mechanism as described in greater detail further below.

Figure 51:
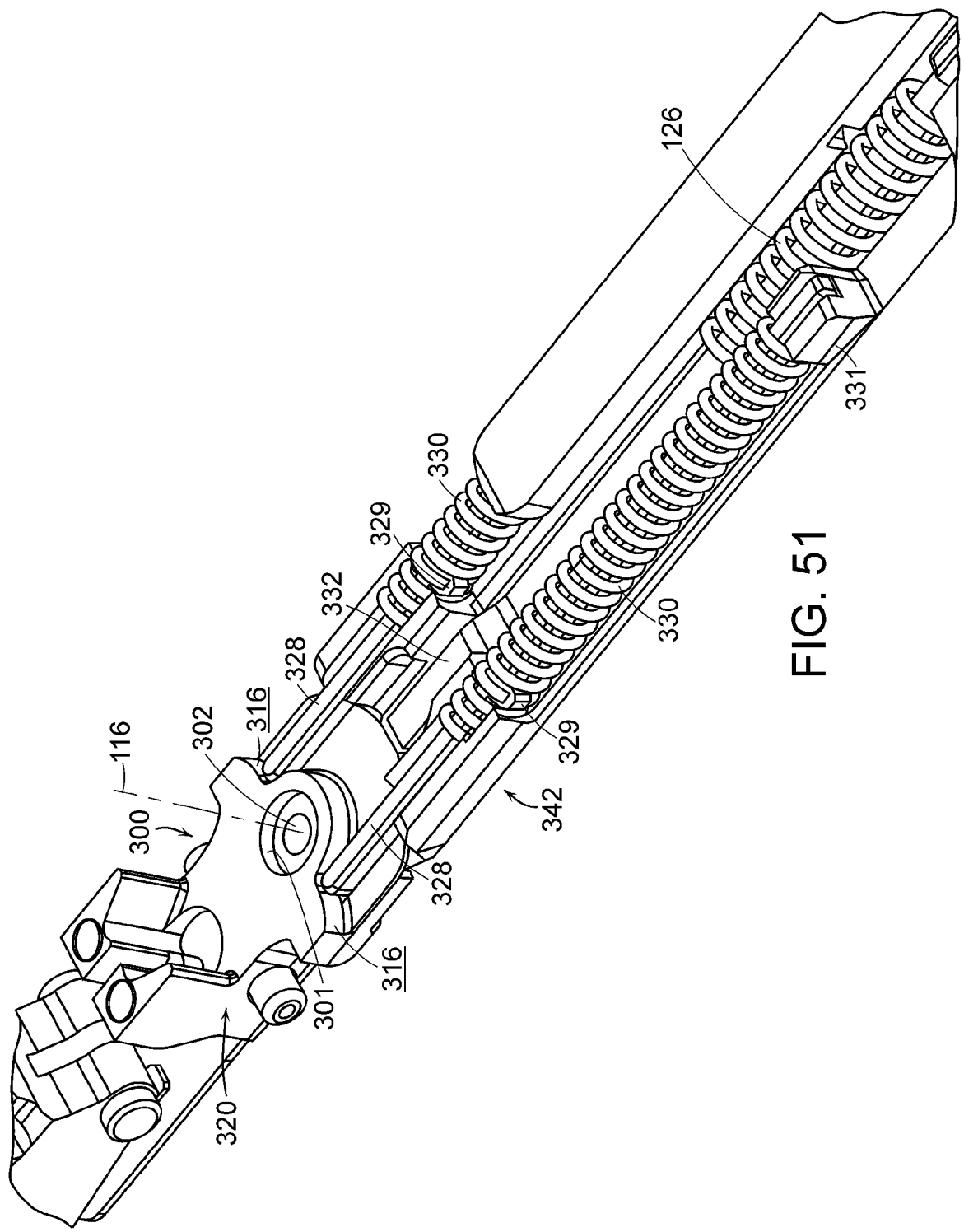
FIG. 51 is a perspective view of the articulation joint of FIG. 5 with some components of the surgical instrument removed.
Figure 52:
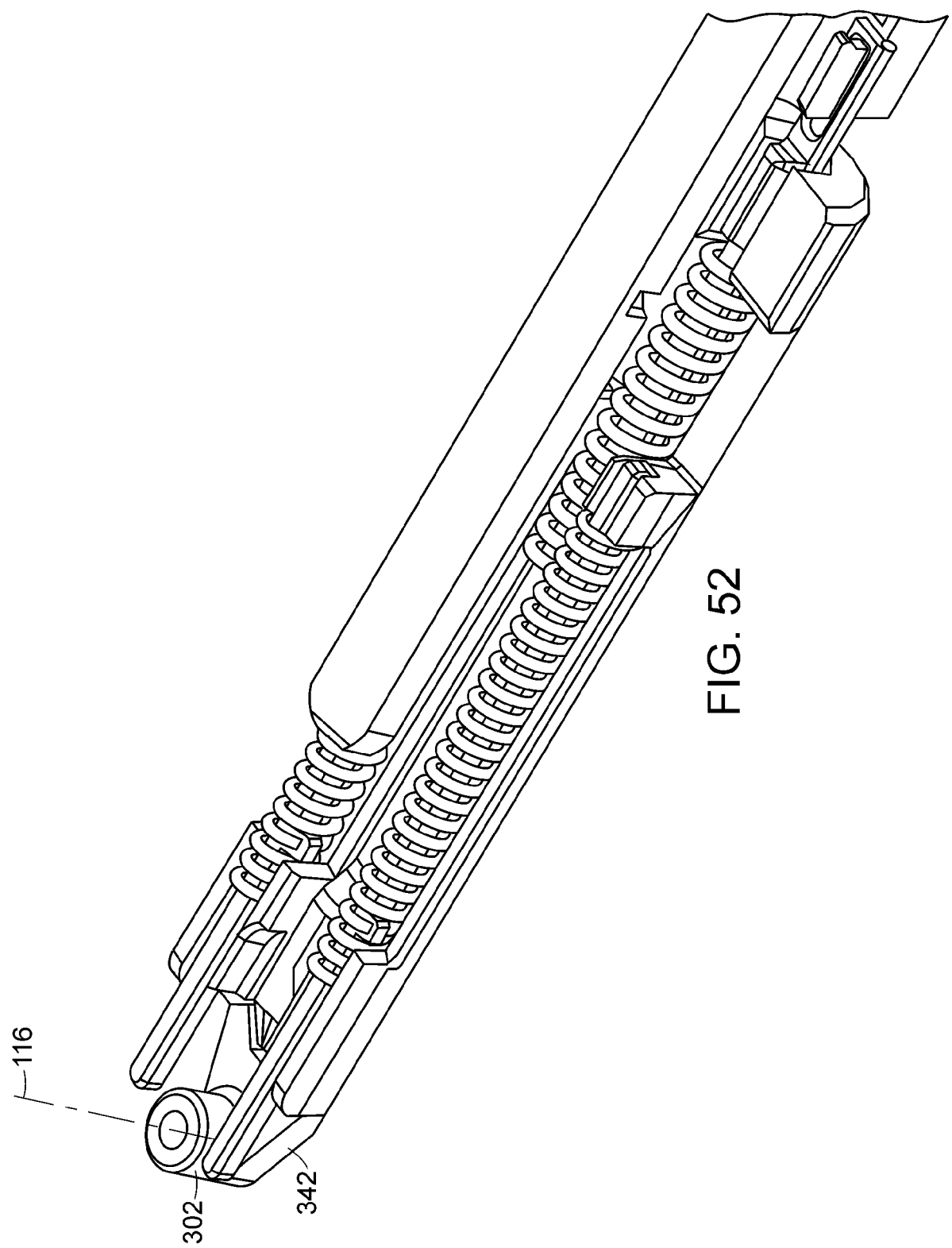
FIG. 52 is a perspective view of the articulation joint of FIG. 5 with additional components of the surgical instrument removed.
Figure 53:
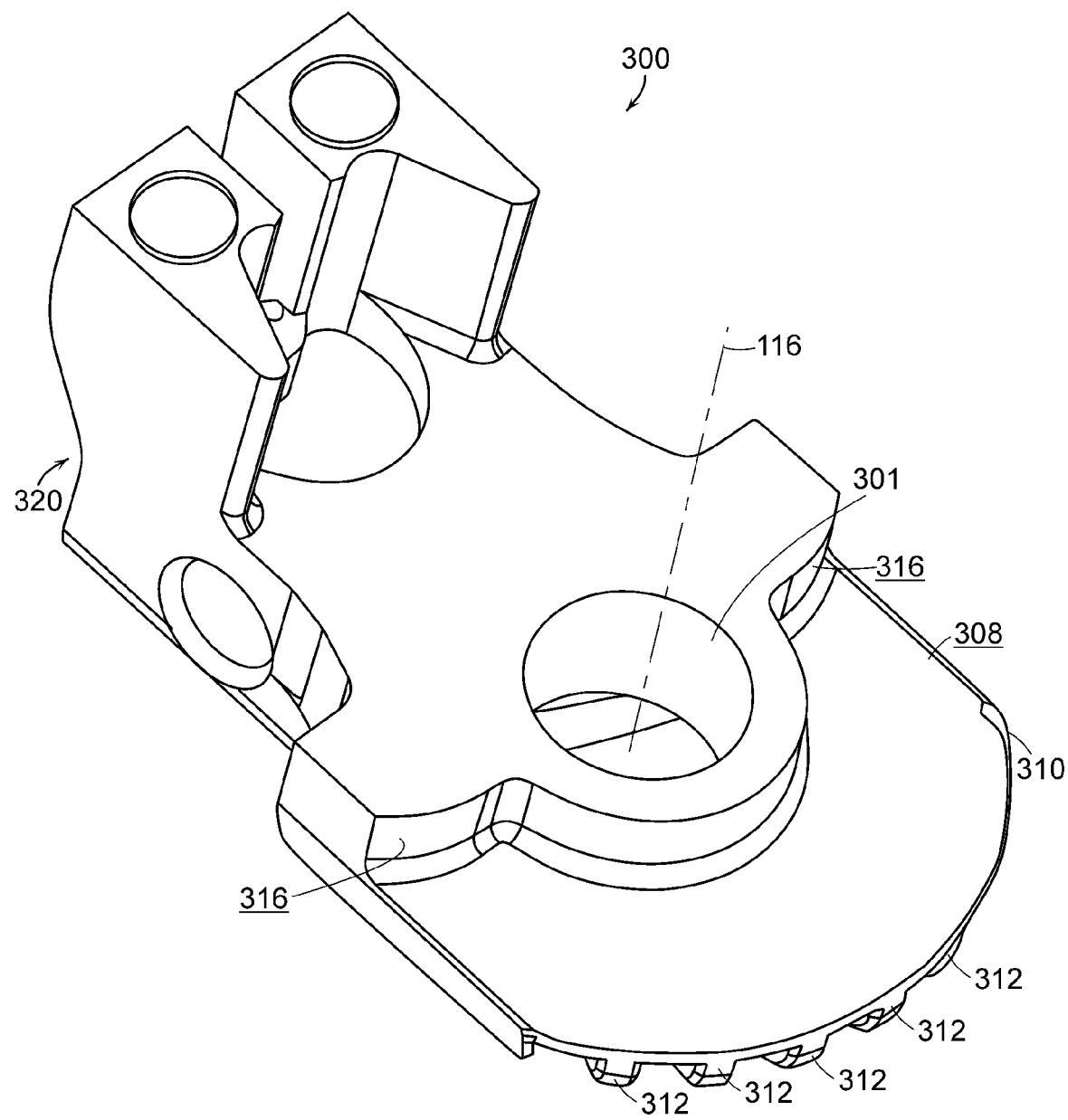
FIG. 53 is a perspective view of a lock member of the end effector of FIG. 3.
Figure 54:
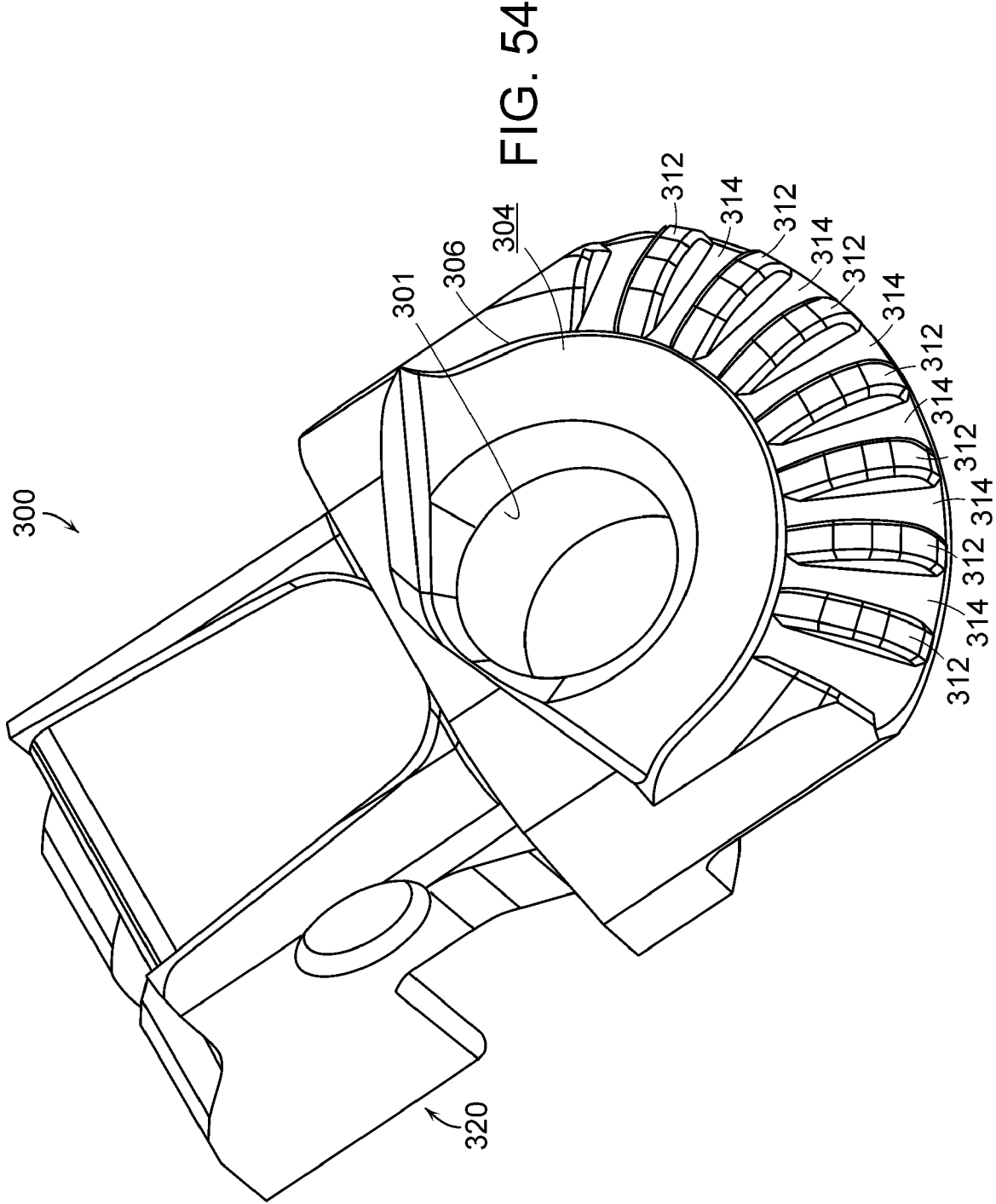
FIG. 54 is another perspective view of the end effector lock member of FIG. 53.
Figure 55:
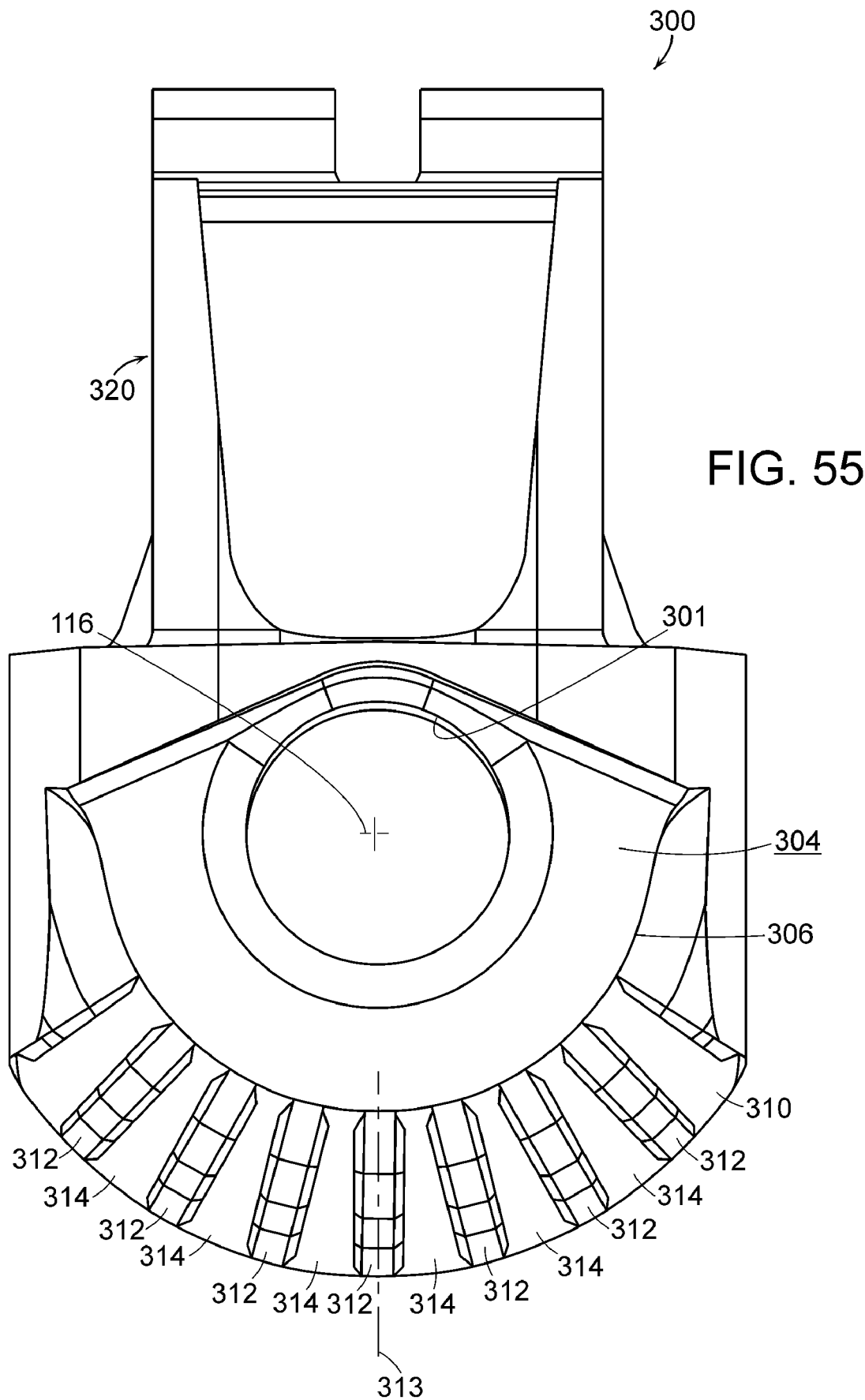
FIG. 55 is a bottom view of the end effector lock member of FIG. 53.
Figure 56:
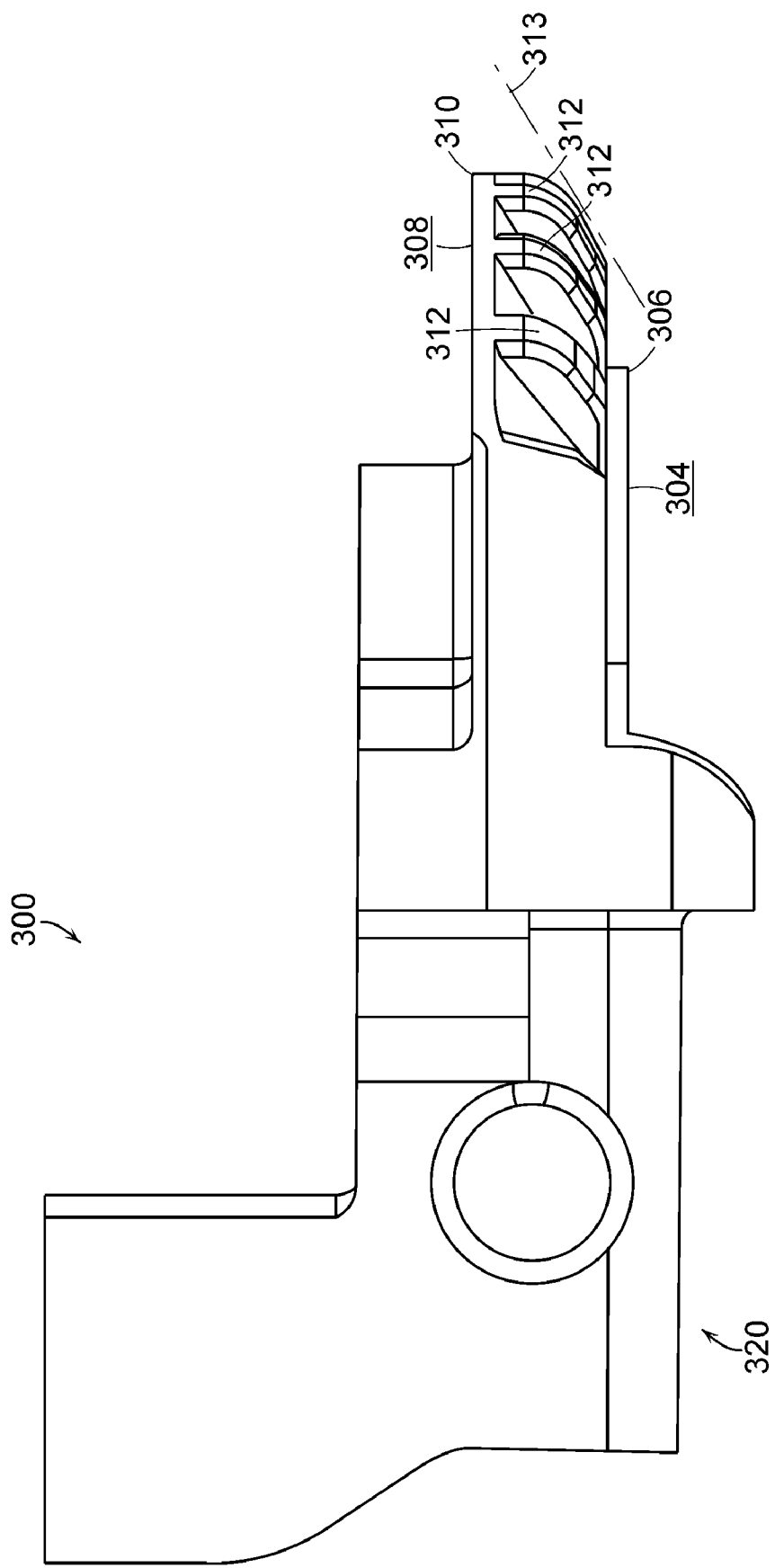
FIG. 56 is an elevational view of the end effector lock member of FIG. 53.

In at least one embodiment, referring to FIGS. 51 and 52, articulation joint 114 can include end effector lock member 300 and pivot 302. In various embodiments, referring to FIGS. 53-56, end effector lock member 300 can include connector portion 320 which can secure lock member 300 to end effector 106 and, referring to FIG. 52, shaft assembly 104 can include pivot connector 342, where pivot connector 342 can include pivot 302 extending therefrom. In various embodiments, lock member 300 can include aperture 301 which can be sized and configured to receive at least a portion of pivot 302 therein. In at least one embodiment, pivot 302 and aperture 301 can be configured such that end effector 106 can rotate freely about axis 116. In other various embodiments, pivot 302 and aperture 301 can be configured such that friction between pivot 302 and aperture 301 can resist, although permit, relative movement between end effector 106 and shaft assembly 104. Although not illustrated, articulation joint 114 can include more than one axis, or pivot, about which end effector 106 can be rotated.

In various embodiments, a surgeon can articulate end effector 106 relative to shaft assembly 104 by pushing end effector 106 against a cavity side wall surrounding a surgical site, for example, and applying a force to shaft assembly 104 such that end effector 106 pivots about axis 116. Thereafter, if the surgeon desires to re-center end effector 106, i.e., orient end effector 106 and shaft assembly 104 along a line, the surgeon can place end effector 106 against a cavity side wall once again, for example, and a apply a force to shaft assembly 104 as described above. In various embodiments, referring to FIGS. 51 and 52, surgical instrument 100 can include a re-centering mechanism which can automatically re-center, or at least substantially re-center, end effector 106 relative to shaft assembly 104. In various embodiments, end effector lock member 300 can include centering surfaces 316 and elongate shaft assembly 104 can include centering shafts 328 and biasing members 330, where biasing members 330 can be configured to bias centering shafts 328 against centering surfaces 316. In at least one such embodiment, centering surfaces 316 can be disposed on substantially opposite sides of axis 116 such that centering shafts 328 can apply a substantially equal torque, or moment, to lock member 300 and, absent an additional motivating force, hold end effector 106 in a substantially centered position. When end effector 106 is articulated by such a motivating force, as described above, lock member 300 can be configured to displace one of centering shafts 328 proximally and compress the biasing member 330 operably engaged therewith. More particularly, the biasing member 330 can be positioned between a guide 331 and at least one projection 329 extending from centering shaft 328 such that, when projection 329 is moved proximally by shaft 328, biasing member 330 is compressed therebetween. After the motivating force is removed, the compressed biasing member 330 can expand and rotate lock member 300 to its center position via centering shaft 328, or to a position where the torque applied by biasing members 330 is substantially balanced. Although biasing member 330 is illustrated as a coil spring, biasing member 330 can include any suitable elastic member.

In various embodiments, a locking mechanism can be used to hold end effector 106 in its articulated position even after the motivating force has been removed. In at least one embodiment, referring to FIGS. 53-56, end effector lock member 300 can include a first portion having first surface 308, a second portion having second surface 304, teeth 312, and recesses 314 defined between teeth 312 where, as described in greater detail further below, teeth 312 and recesses 314 can be configured to be operably engaged with a shaft assembly locking member in order to fix, or lock, the relative relationship between end effector 106 and shaft assembly 104. In various embodiments, teeth 312 and recesses 314 can be positioned intermediate first surface 308 and second surface 304. In at least one embodiment, first surface 308 can extend from aperture 301 to first perimeter 310, and second surface 304 can extend from aperture 301 to second perimeter 306. In various embodiments, first perimeter 310 can define a first plane and second perimeter 306 can define a second plane where teeth 312 and recesses 314 can be positioned intermediate the first and second planes. In embodiments where first perimeter 310 is different than second perimeter 306, teeth 312 can extend at an angle, or bevel, therebetween. In various embodiments, a tooth 312 can intersect first perimeter 310 at a point further away from axis 116 than a point at which the tooth 312 intersects second perimeter 306. In at least one embodiment, at least one of the teeth 312 can define a first axis 313 which can extend between first surface 308 and second surface 304 in a direction which is not perpendicular to first surface 308 and/or axis of rotation 116. In such embodiments, teeth 312 can slide over soft tissue, for example, which is positioned adjacent to articulation joint 114. Stated another way, owing to the angled, or beveled, surfaces of teeth 112, the probability of teeth 112 catching on, or impinging upon, the soft tissue surrounding articulation joint 114 when end effector 106 is articulated can be reduced. In at least one embodiment, teeth 312 may not extend beyond first perimeter 310 such that, in the event that at least a portion of first perimeter 310 is in contact with soft tissue, for example, first perimeter 310 and teeth 312 can, as above, easily slide relative to the soft tissue.

Figure 57:
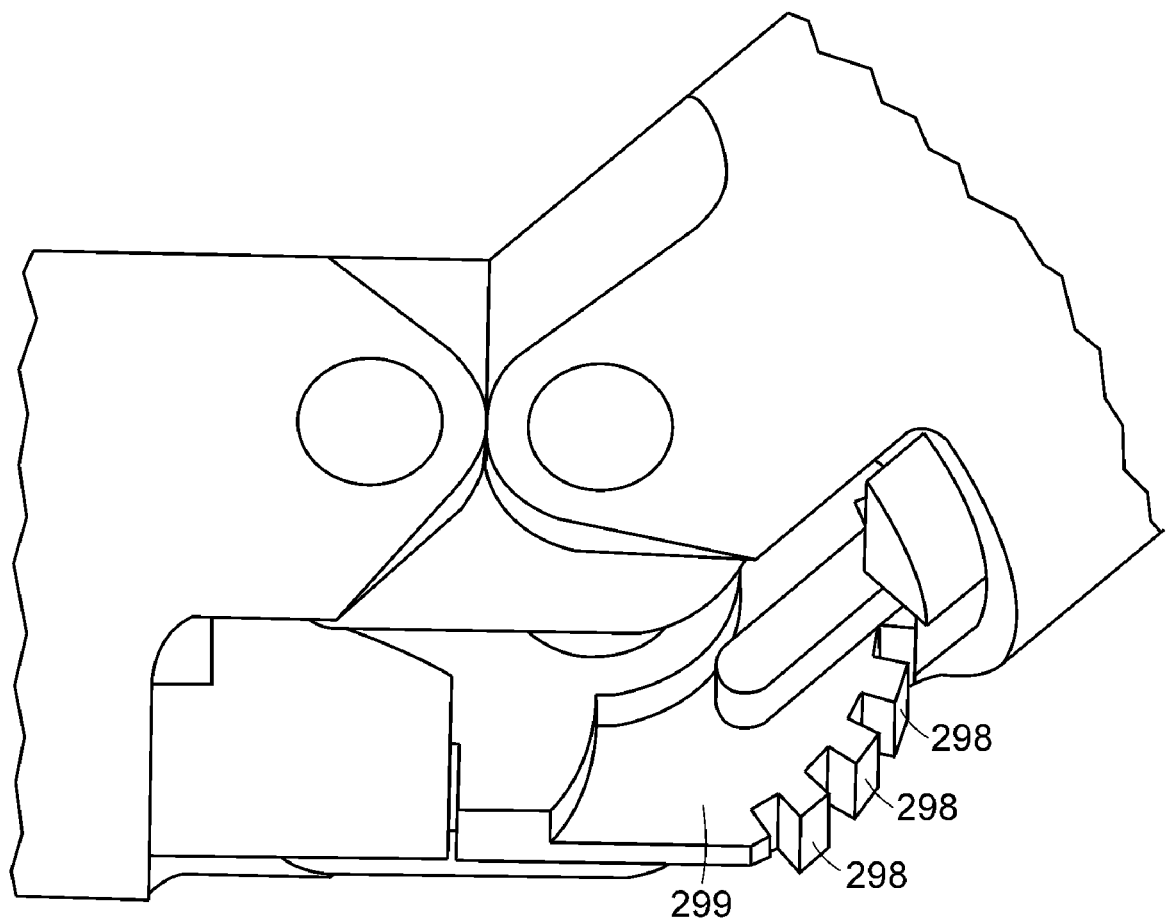
FIG. 57 is a partial perspective view of an articulation joint of a previous surgical instrument.
Figure 58:
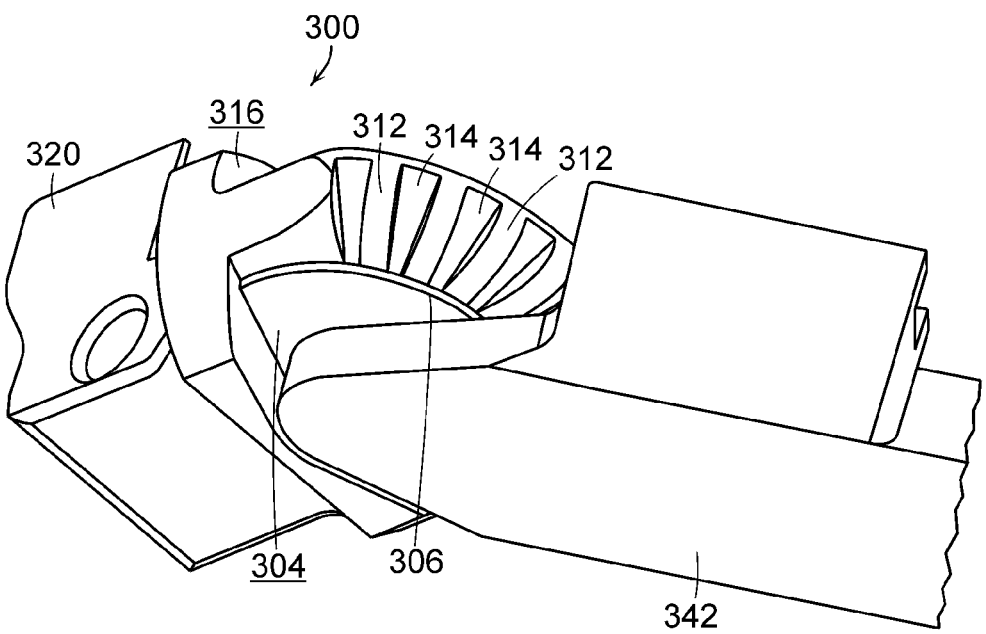
FIG. 58 is a perspective view of the articulation joint of FIG. 5 with some components of the end effector and elongate shaft assembly removed.
Figure 59:
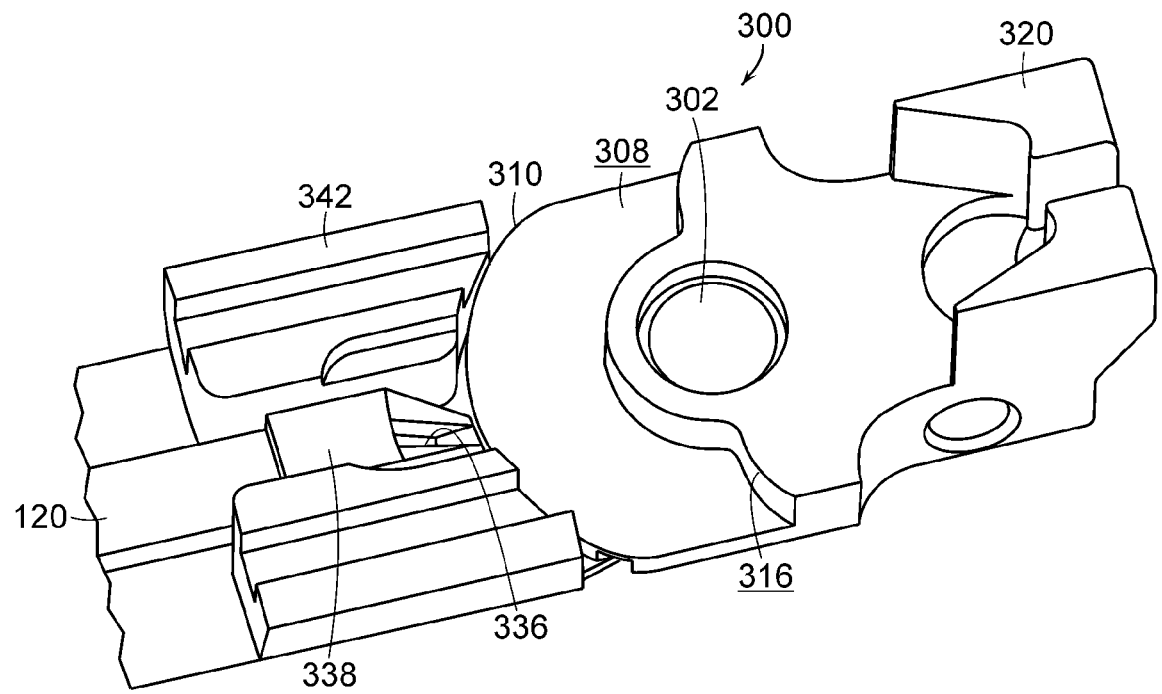
FIG. 59 is another perspective view of the articulation joint of FIG. 5 with some components of the end effector and elongate shaft assembly removed.
Figure 60:
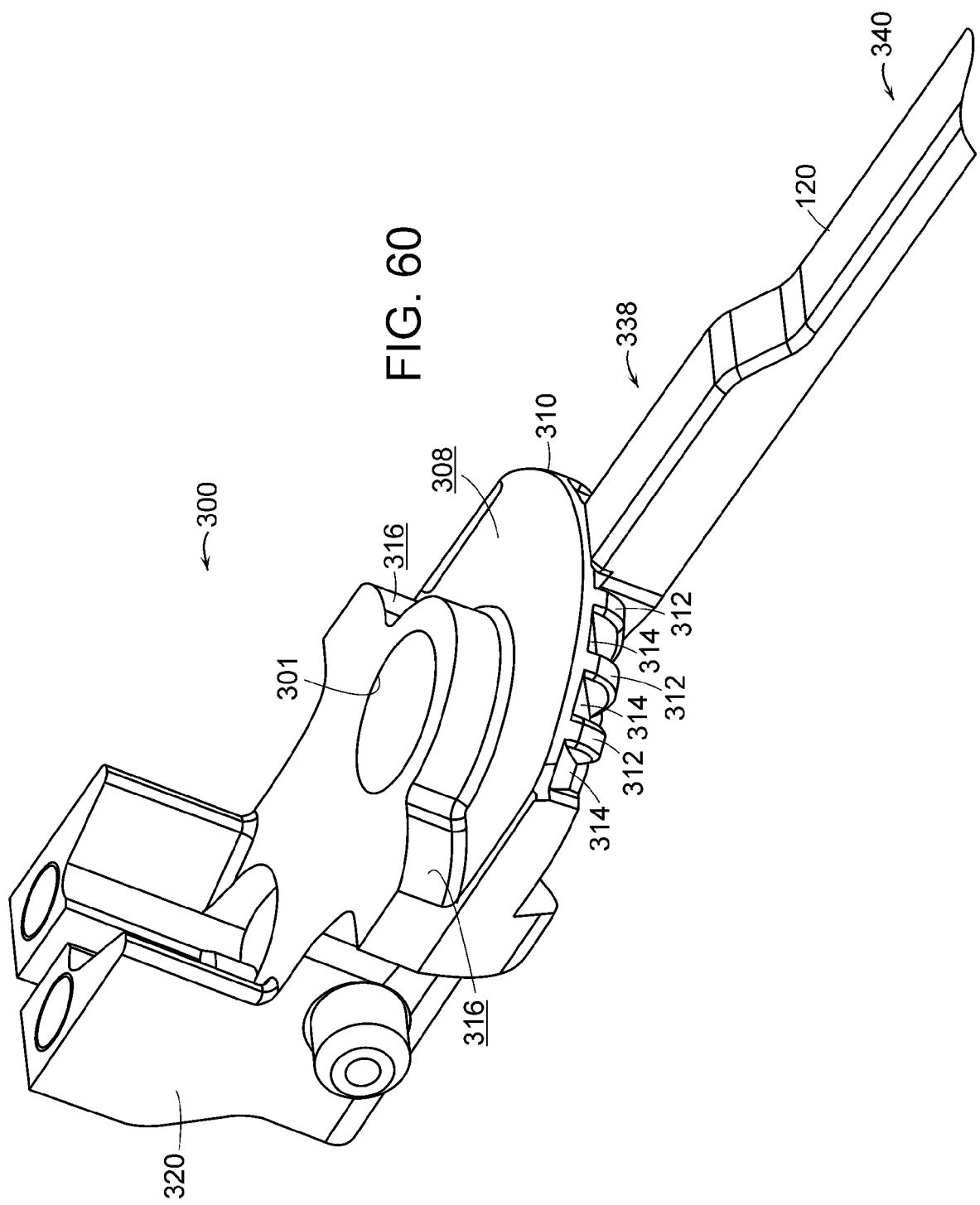
FIG. 60 is a perspective view of the end effector lock member of FIG. 53 operably engaged with a lock member of the elongate shaft assembly.
Figure 61:
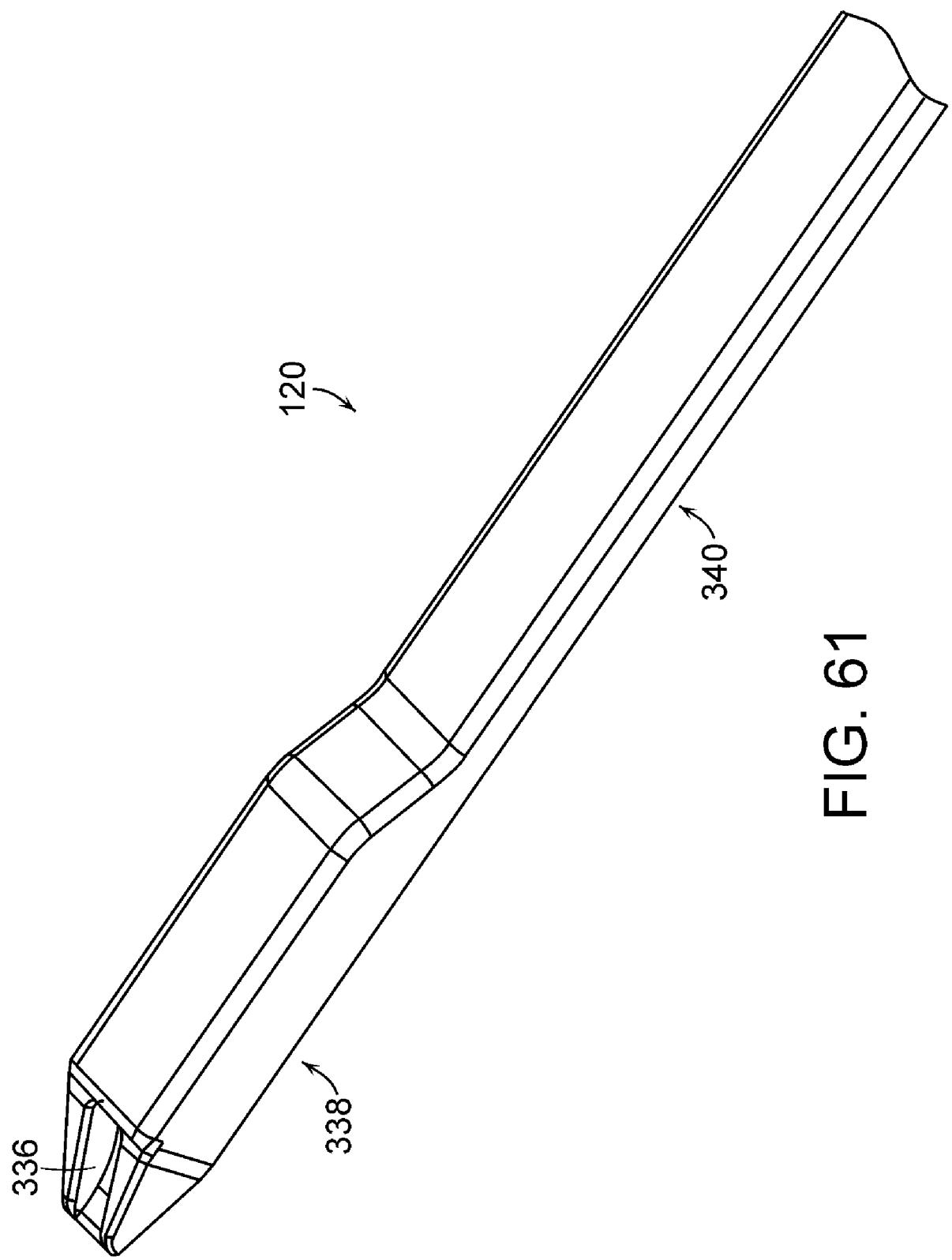
FIG. 61 is a perspective view of the shaft assembly lock member of FIG. 60.
Figure 62:
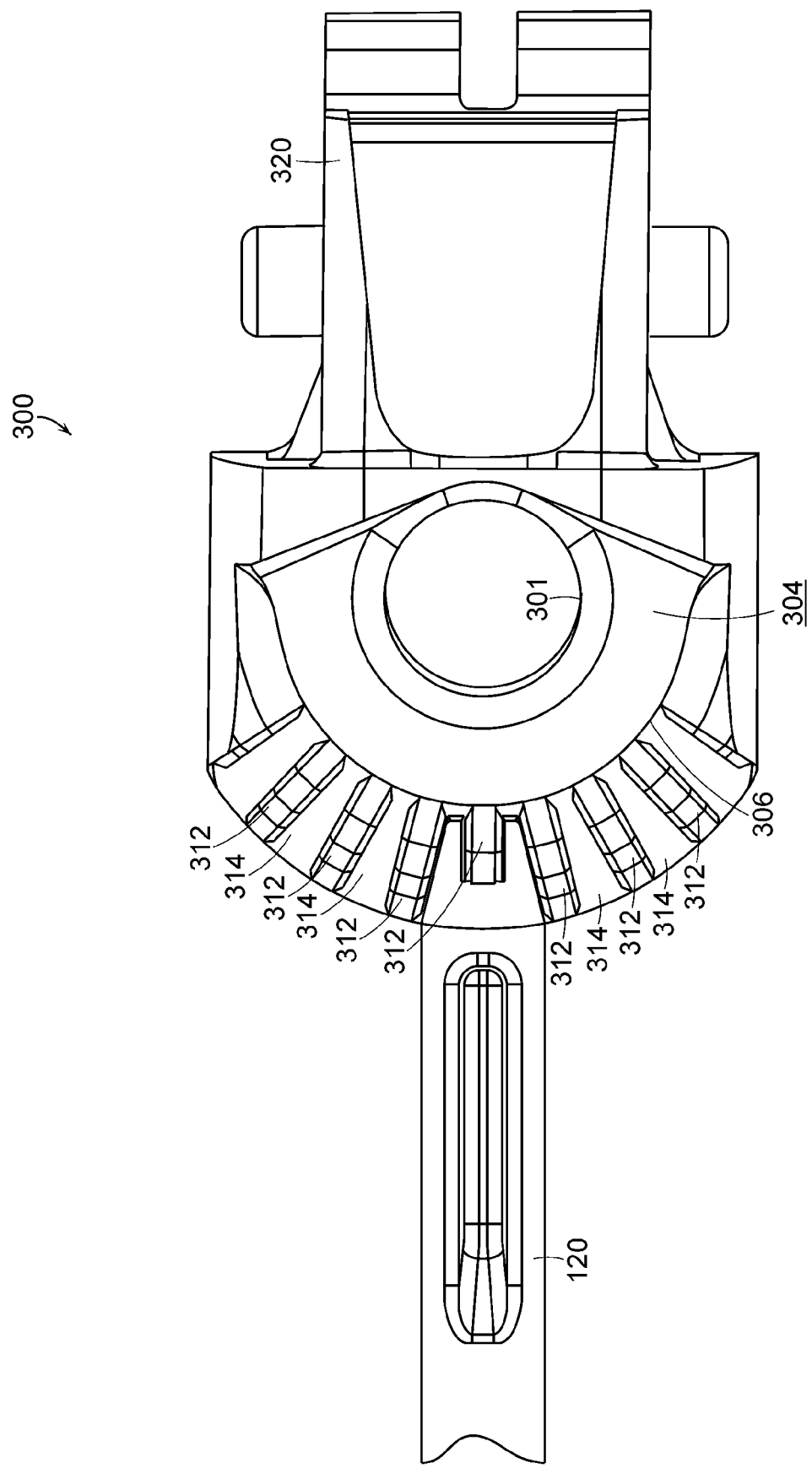
FIG. 62 is a bottom view of end effector lock member of FIG. 53 operably engaged with the shaft assembly lock member of FIG. 60.
Figure 63:
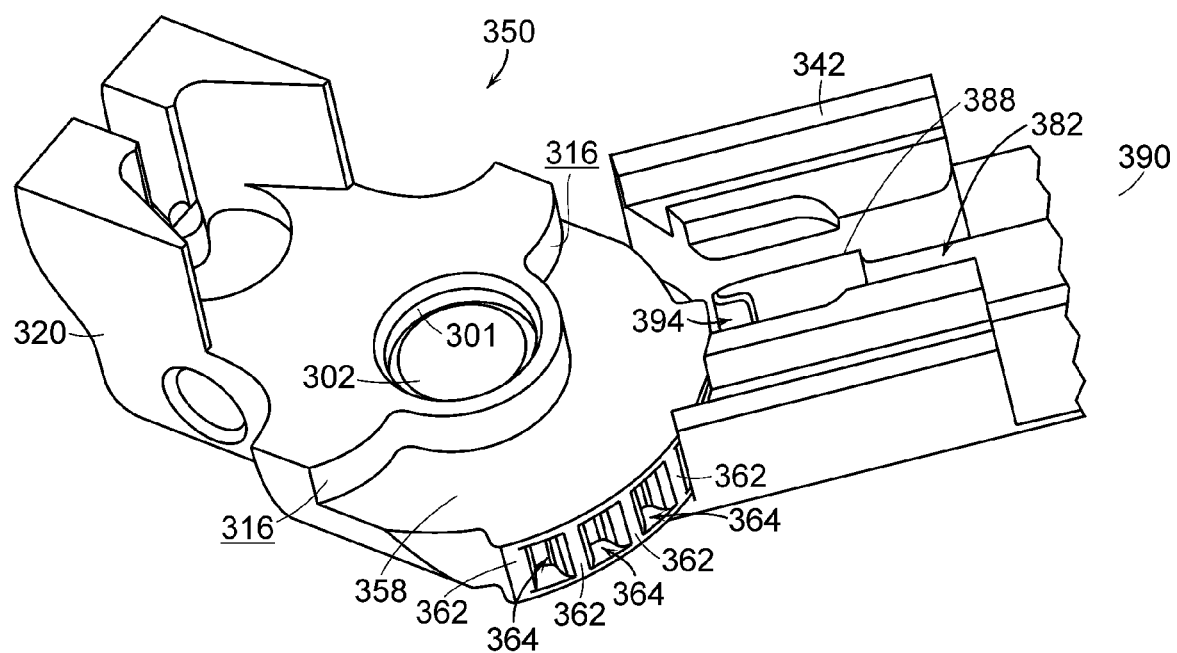
FIG. 63 is a perspective view of an articulation joint of a surgical instrument in accordance with an alternative embodiment of the present invention with some components of the surgical instrument removed.
Figure 64:
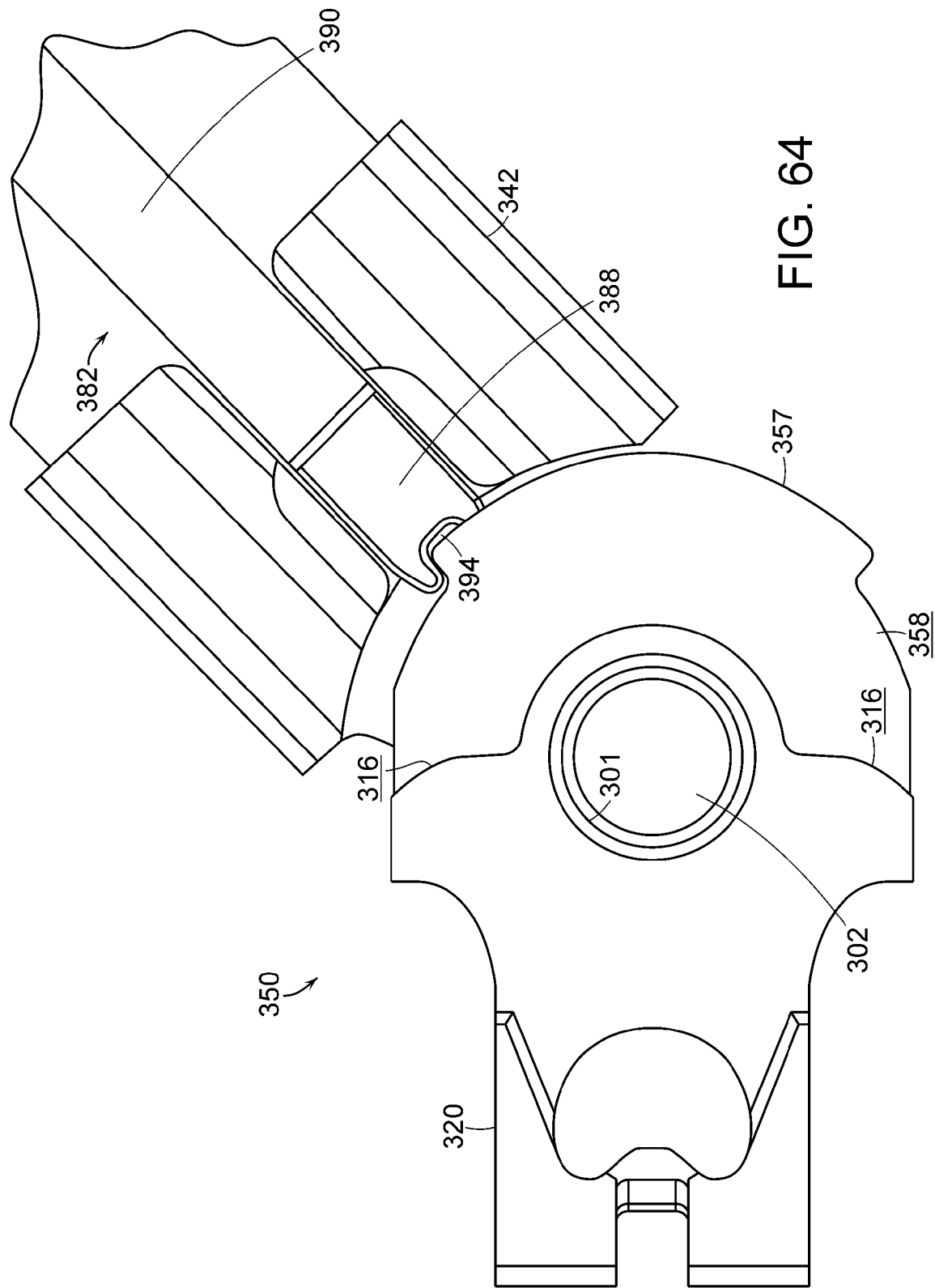
FIG. 64 is a top view of an end effector lock member operably engaged with a shaft assembly lock member of the surgical instrument of FIG. 63.
Figure 65:
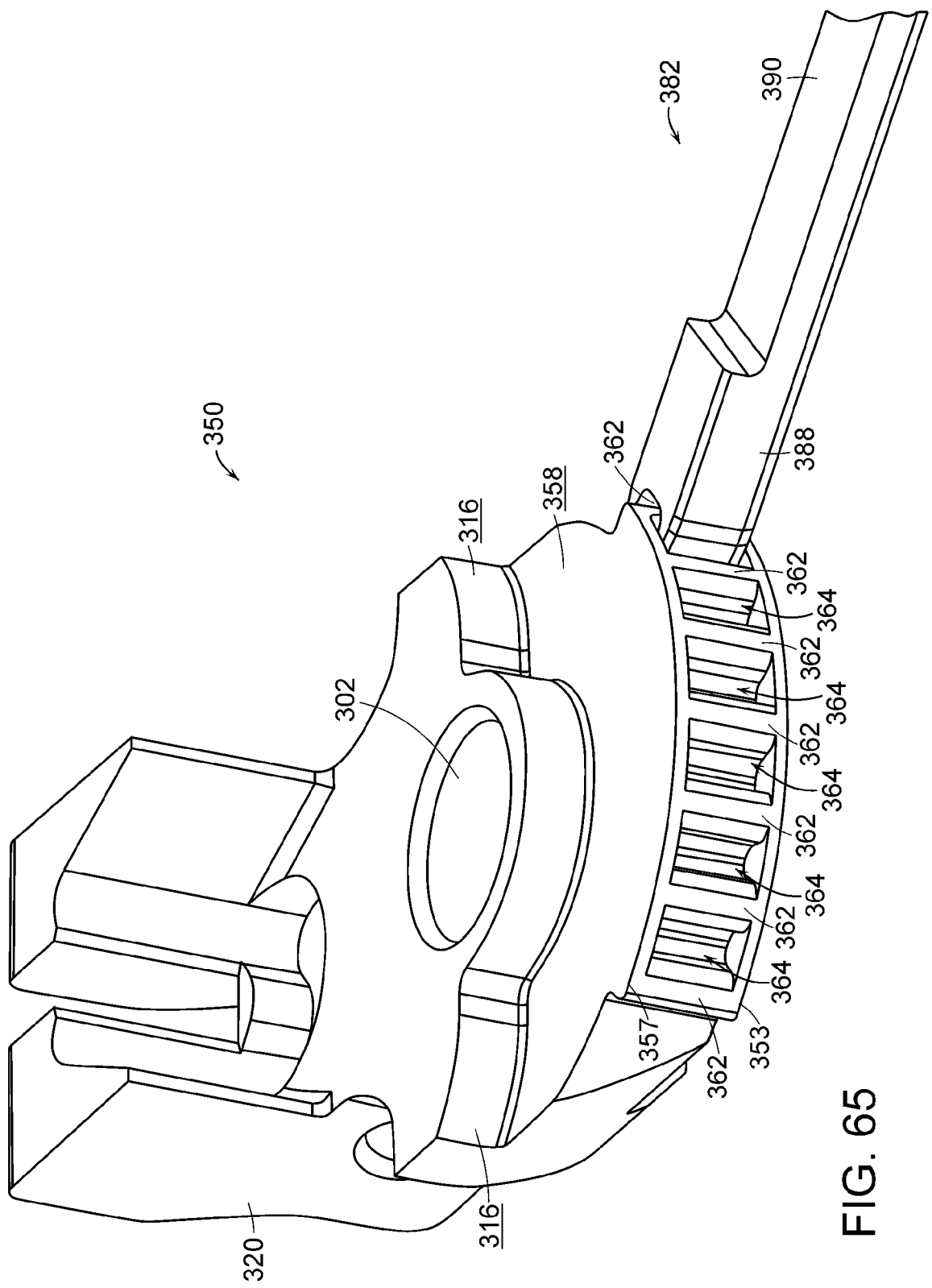
FIG. 65 is a perspective view of the end effector lock member operably engaged with the shaft assembly lock member of FIG. 64.
Figure 66:
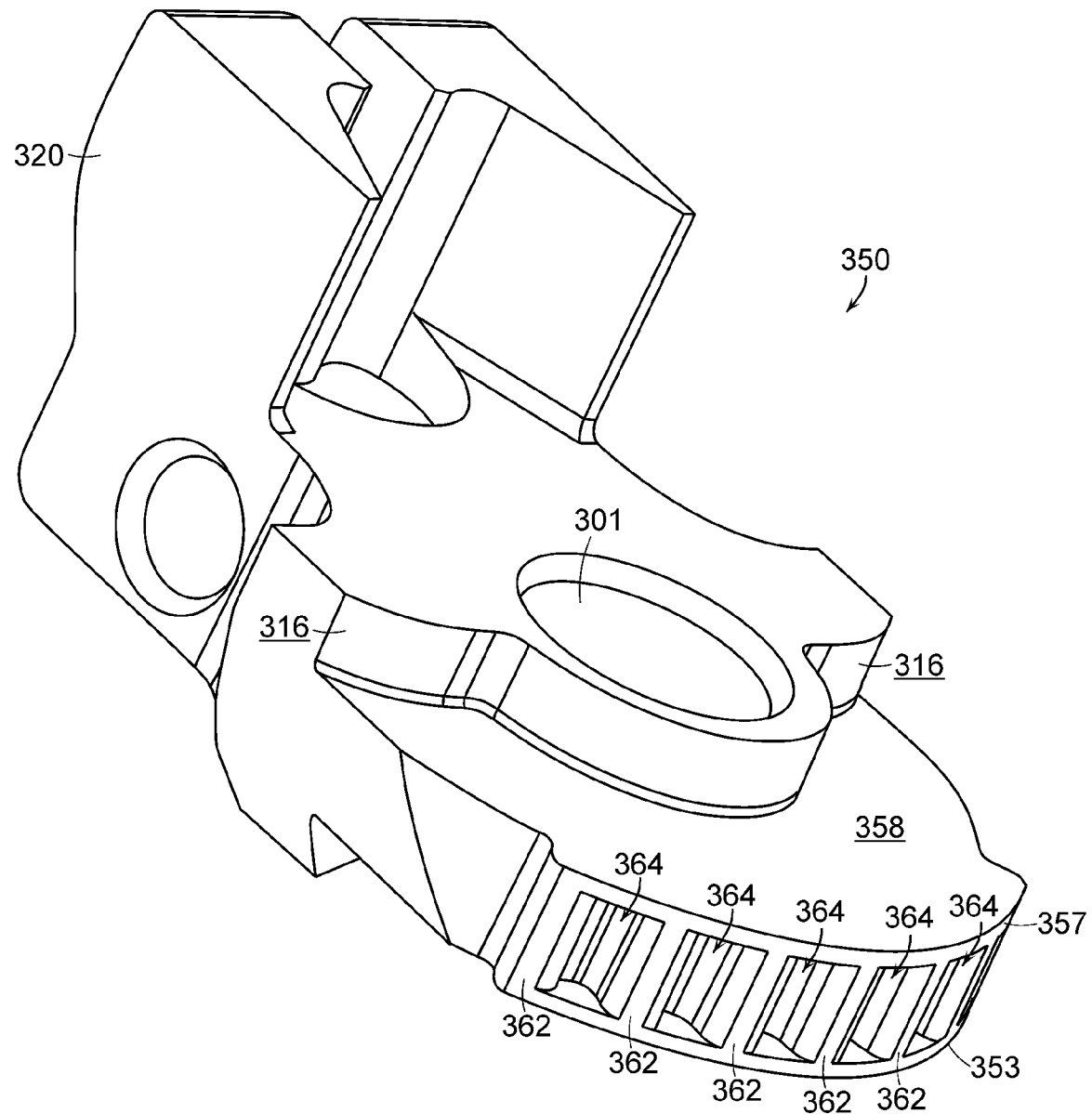
FIG. 66 is a perspective view of the end effector lock member of FIG. 64.
Figure 67:
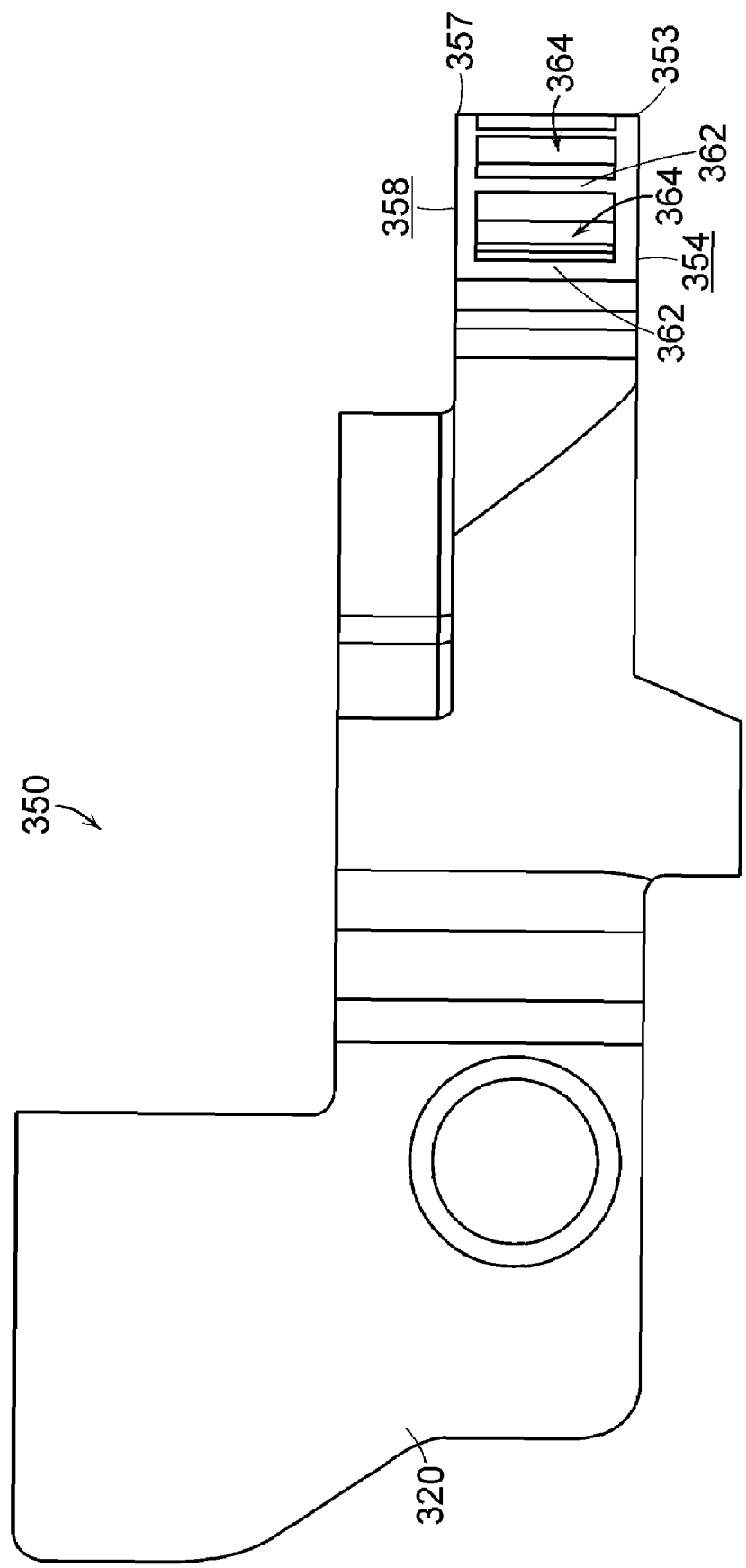
FIG. 67 is an elevational view of the end effector lock member of FIG. 64.

Further to the above, embodiments of the present invention can provide significant advantages over previous surgical instruments. More particularly, referring to FIG. 57, the articulation joints of previous end effectors have included lock members, such as lock member 299, for example, which include teeth 298 that extend outwardly from the perimeter of the lock member. As a result, when the end effector is articulated relative to the shaft assembly of the surgical instrument, teeth 298 can catch on, or impinge upon, the surrounding soft tissue and potentially cause trauma thereto. In various circumstances, tissue can be caught between adjacent teeth 298 such that, when the end effector is articulated, the soft tissue can be pulled into the articulation joint and can be pinched by the relatively moving components of the joint. In embodiments of the present invention in which the teeth of the lock member are angled, or beveled, as outlined above and illustrated in FIG. 58, the soft tissue can more easily flow over the teeth and reduce the possibility that the soft tissue can be pulled into the articulation joint.

As outlined above, referring to FIGS. 59-62, surgical instrument 100 can further include locking member 120 which can be slid relative to end effector 106 and can be operably engaged with end effector 106 to prevent, or at least limit, relative movement between shaft assembly 104 and end effector 106. In at least one embodiment, lock member 120 can be configured to engage at least one of teeth 312 such that end effector 106 is prevented from moving relative to lock member 120. More particularly, lock member 120 can include end portion 338 and shaft portion 340, where end portion 338 can include recess 336 which can be configured to receive a tooth 312 of lock member 300 in a close-fit, or even interference-fit, relationship. In various alternative embodiments, locking portion 338 can be received within at least one of recesses 314 in a close-fit, or interference-fit relationship similar to the above. In either event, surgical instrument 100 can further include spring 126 which can be configured to bias lock member 120 into engagement with end effector lock member 300. In the event that recess 336 is not aligned with a tooth 312, in at least one embodiment, the biasing force applied to lock member 120 by spring 126 can cause lock member 120 to contact and rotate end effector lock member 300 about axis 116 until one of teeth 312 is aligned with recess 336. In various embodiments, spring 126 can comprise any suitable biasing member including a helical spring, leaf spring, or other biasing material.

In various alternative embodiments, referring to FIGS. 63-67, a surgical instrument can include end effector lock member 350 comprising aperture 301, a first portion including first surface 358, a second portion including second surface 354 (FIG. 67), and connector portion 320. End effector lock member 350 can also comprise teeth 362 and recesses 364 defined between teeth 362 where, in at least one embodiment, teeth 362 and recesses 364 can be positioned intermediate first surface 358 and second surface 354. In various embodiments, referring to FIGS. 65-67, teeth 362 may not extend beyond first perimeter 357 of first surface 358 and/or second perimeter 353 of second surface 354. In at least one such embodiment, teeth 362 may be completely positioned, or contained, between first surface 358 and second surface 354. In at least one alternative embodiment, teeth 362 may partially extend from first perimeter 357 and/or second perimeter 353. In various embodiments, first perimeter 357 and second perimeter 353 can define an outer surface therebetween where recesses 364 can be defined in the outer surface. As a result of the above-described features, end effector lock member 350 can slide relative to soft tissue positioned adjacent to the articulation joint without impinging on the soft tissue. In various embodiments, teeth 362 may be blunted or rounded to further facilitate the relative sliding described above. In at least one embodiment, referring to FIGS. 63-65, a locking mechanism can be configured to engage at least one of teeth 362 and recesses 364 and can include lock member 382 comprising end portion 388 and shaft portion 390. In at least one embodiment, similar to the above, end portion 388 can include recess 394 which can be configured to engage at least one of teeth 362, for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical instrument, comprising:
   a firing drive configured to generate a firing motion;
   an end effector, comprising:
      a channel configured to receive a staple cartridge;
      an anvil movably coupled to said channel; and
      a cutting member operably supported within said channel, wherein said cutting member is operably engaged with said firing drive and is responsive to said firing motion;
   a closure drive configured to generate a closing motion, wherein said anvil is operably engaged with said closure drive and is movably responsive to said closing motion, and wherein said closure drive includes:
      a trigger, wherein said anvil is movable between an open position and a partially closed position when said trigger is moved between a first position and a second position, and wherein said anvil is movable between said partially closed position and a closed position when said trigger is moved between said second position and a third position; and
   a lock member configured to selectively engage said closure drive and lock said anvil in said partially closed position and said closed position.

2. The surgical instrument of claim 1, wherein said lock member is configured to selectively prevent said anvil from returning to said open position after being moved into said partially closed position.

3. The surgical instrument of claim 2, further comprising a lock release configured to disengage said lock member from said closure drive such that said anvil can be moved from said partially closed position into said open position.

4. The surgical instrument of claim 2, wherein said lock member is configured to selectively prevent said anvil from returning to said partially closed position after being moved into said closed position.

5. The surgical instrument of claim 1, wherein said lock member is configured to prevent said anvil from returning to said open position after being moved into said partially closed position without first being moved into said closed position.

6. The surgical instrument of claim 1, wherein said trigger includes a first retention feature, wherein said lock member includes a follower portion, wherein said closure drive further includes a lock spring configured to bias said follower portion against said trigger, wherein said trigger is configured to slide relative to said follower portion as said trigger is moved between said first position and said second position, and wherein said follower portion is configured to engage said first retention member when said anvil is moved into said partially closed position and to prevent said trigger from moving from said second position into said first position.

7. The surgical instrument of claim 6, wherein said trigger further includes a second retention feature, wherein said trigger is configured to slide relative to said follower portion as said trigger is moved between said second position and said third position, and wherein said follower portion is configured to engage said second retention feature when said anvil is moved into said closed position and to prevent said trigger from moving from said third position into said second position.

8. A surgical instrument, comprising:
   a firing drive configured to generate a firing motion;
   an end effector, comprising:
      a channel configured to receive a staple cartridge;
      an anvil movably coupled to said channel; and
      a cutting member operably supported within said channel, wherein said cutting member is operably engaged with said firing drive and is responsive to said firing motion;
   a closure drive configured to generate a closing motion, wherein said anvil is operably engaged with said closure drive and is movably responsive to said closing motion, and wherein said closure drive includes:
      a trigger, wherein said anvil is movable between an open position and a partially closed position when said trigger is moved between a first position and a second position, and wherein said anvil is movable between said partially closed position and a closed position when said trigger is moved between said second position and a third position: and
      a lock member configured to selectively engage said closure drive and lock said anvil in at least one of said partially closed position and said closed position,
   wherein said trigger includes a cam portion having a first notch, wherein said lock member includes a follower portion, wherein said closure drive further includes a lock spring configured to bias said follower portion against said cam portion, wherein said cam portion is configured to slide relative to said follower portion as said trigger is moved between said first position and said second position, and wherein said follower portion is configured to engage said first notch when said anvil is moved into said partially closed position and to prevent said trigger from moving from said second position into said first position.

9. The surgical instrument of claim 8, wherein said lock member is pivotably mounted relative to said cam portion, and wherein said lock member is configured to be pivoted away from said cam portion to disengage said follower portion from said first notch and allow said trigger to be moved from said second position into said first position.

10. The surgical instrument of claim 9, further comprising a trigger return spring operably engaged with said trigger, wherein said trigger return spring is configured to move said trigger from said second position into said first position after said follower portion has been disengaged from said first notch.

11. The surgical instrument of claim 8, wherein said cam portion further includes a second notch, wherein said cam portion is configured to slide relative to said follower portion as said trigger is moved between said second position and said third position, and wherein said follower portion is configured to engage said second notch when said anvil is moved into said closed position and to prevent said trigger from moving from said third position into said second position.

12. A method for processing an instrument for surgery, the method comprising:
   obtaining the surgical instrument of claim 1;
   sterilizing the surgical instrument; and
   storing the surgical instrument in a sterile container.

13. A surgical instrument, comprising:
   a firing drive configured to generate a firing motion;
   an end effector operably engaged with said firing drive, said end effector comprising:
      a channel configured to receive a staple cartridge; and
      an anvil movably coupled to said channel; and
   a closure drive configured to generate a closing motion, wherein said anvil is operably engaged with said closure drive and is movably responsive to said closing motion, and wherein said closure drive includes:
      a trigger, wherein said trigger is movable between a first position and a second position, and wherein said trigger is movable between said second position and a third position; and
      a lock member, wherein said lock member is configured to engage said trigger and selectively lock said trigger in said second position and said third position.

14. The surgical instrument of claim 13, wherein said trigger includes a first retention feature, wherein said lock member includes a follower portion, wherein said closure drive further includes a lock spring configured to bias said follower portion against said trigger, wherein said trigger is configured to slide relative to said follower portion as said trigger is moved between said first position and said second position, and wherein said follower portion is configured to engage said first retention feature and prevent said trigger from moving from said second position into said first position.

15. The surgical instrument of claim 14, wherein said trigger further includes a second retention feature, wherein said trigger is configured to slide relative to said follower portion as said trigger is moved between said second position and said third position, and wherein said follower portion is configured to engage said second retention feature and prevent said trigger from moving from said third position into said second position.

16. A surgical instrument, comprising:
   a firing drive configured to generate a firing motion;
   an end effector operably engaged with said firing drive, said end effector comprising:
      a channel configured to receive a staple cartridge; and
      an anvil movably coupled to said channel; and
   a closure drive configured to generate a closing motion, wherein said anvil is operably engaged with said closure drive and is movably responsive to said closing motion, and wherein said closure drive includes:
      a trigger, wherein said trigger is movable between a first position and a second position, and wherein said trigger is movable between said second position and a third position; and
      a lock member, wherein said lock member is configured to engage said trigger and selectively lock said trigger in at least one of said second position and said third position,
   wherein said trigger includes a cam portion having a first notch, wherein said lock member includes a follower portion, wherein said closure drive further includes a lock spring configured to bias said follower portion against said cam portion, wherein said cam portion is configured to slide relative to said follower portion as said trigger is moved between said first position and said second position, and wherein said follower portion is configured to engage said first notch and prevent said trigger from moving from said second position into said first position.

17. The surgical instrument of claim 16, wherein said lock member is pivotably mounted relative to said cam portion, and wherein said lock member is configured to be pivoted away from said cam portion to disengage said follower portion from said first notch and allow said trigger to be moved from said second position into said first position.

18. The surgical instrument of claim 17, further comprising a trigger return spring operably engaged with said trigger, wherein said trigger return spring is configured to move said trigger from said second position into said first position after said follower portion has been disengaged from said first notch.

19. The surgical instrument of claim 16, wherein said cam portion further includes a second notch, wherein said cam portion is configured to slide relative to said follower portion as said trigger is moved between said second position and said third position, and wherein said follower portion is configured to engage said second notch and prevent said trigger from moving from said third position into said second position.

20. A method for processing an instrument for surgery, the method comprising:
obtaining the surgical instrument of claim 13;
sterilizing the surgical instrument; and
storing the surgical instrument in a sterile container.

21. A surgical instrument, comprising:
a firing drive configured to generate a firing motion;
an end effector operably engaged with said firing drive, said end effector comprising:
a channel configured to receive a staple cartridge; and
an anvil movably coupled to said channel;
a closure drive configured to generate a closing motion, wherein said anvil is operably engaged with said closure drive and is movably responsive to said closing motion, and wherein said closure drive includes:
a trigger, wherein said trigger is movable between an open position and a partially closed position to move said anvil between an open position and a partially closed position, and wherein said trigger is movable between its partially closed position and a closed position to move said anvil between its partially closed position and a closed position; and
a lock member, wherein said lock member is configured to selectively prevent said trigger from returning to its open position after being moved into its partially closed position.

22. The surgical instrument of claim 21, wherein said trigger includes a first retention feature, wherein said lock member includes a follower portion, wherein said closure drive further includes a lock spring configured to bias said follower portion against said trigger, wherein said trigger is configured to slide relative to said follower portion as said trigger is moved between said first position and said second position, and wherein said follower portion is configured to engage said first retention feature and prevent said trigger from moving from said second position into said first position.

23. The surgical instrument of claim 22, wherein said trigger further includes a second retention feature, wherein said trigger is configured to slide relative to said follower portion as said trigger is moved between said second position and said third position, and wherein said follower portion is configured to engage said second retention feature and prevent said trigger from moving from said third position into said second position.

24. A surgical instrument, comprising:
a firing drive configured to generate a firing motion;
an end effector operably engaged with said firing drive, said end effector comprising:
a channel configured to receive a staple cartridge; and
an anvil movably coupled to said channel;
a closure drive configured to generate a closing motion, wherein said anvil is operably engaged with said closure drive and is movably responsive to said closing motion, and wherein said closure drive includes:
a trigger, wherein said trigger is movable between a first position and a second position, and wherein said trigger is movable between said second position and a third position; and
a lock member, wherein said lock member is configured to selectively prevent said trigger from returning to said first position after being moved into said second position,
wherein said trigger includes a cam portion having a first notch, wherein said lock member includes a follower portion, wherein said closure drive further includes a lock spring configured to bias said follower portion against said cam portion, wherein said cam portion is configured to slide relative to said follower portion as said trigger is moved between said first position and said second position, and wherein said follower portion is configured to engage said first notch and prevent said trigger from moving from said second position into said first position.

25. The surgical instrument of claim 24, wherein said lock member is pivotably mounted relative to said cam portion, and wherein said lock member is configured to be pivoted away from said cam portion to disengage said follower portion from said first notch and allow said trigger to be moved from said second position into said first position.

26. The surgical instrument of claim 25, further comprising a trigger return spring operably engaged with said trigger, wherein said trigger return spring is configured to move said trigger from said second position into said first position after said follower portion has been disengaged from said first notch.

27. The surgical instrument of claim 25, wherein said cam portion further includes a second notch, wherein said cam portion is configured to slide relative to said follower portion as said trigger is moved between said second position and said third position, and wherein said follower portion is configured to engage said second notch and prevent said trigger from moving from said third position into said second position.

28. A method for processing an instrument for surgery, the method comprising:
obtaining the surgical instrument of claim 21;
sterilizing the surgical instrument; and
storing the surgical instrument in a sterile container.

* * * * *